United States Patent
Liu et al.

(10) Patent No.: US 8,455,398 B2
(45) Date of Patent: Jun. 4, 2013

(54) AMIDE COMPOUNDS, PREPARATION METHODS AND USES THEREOF

(75) Inventors: Changling Liu, Shenyang (CN); Baoshan Chai, Shenyang (CN); Hong Zhang, Shenyang (CN); Jichun Yang, Shenyang (CN); Zhinian Li, Shenyang (CN); Yongwu Peng, Shenyang (CN); Junfeng Wang, Shenyang (CN); Jiao Wu, Shenyang (CN); Shicun Ma, Shenyang (CN); Miao Li, Shenyang (CN)

(73) Assignees: Sinochem Corporation, Beijing (CN); Shenyang Research Institute of Chemical Industry Co., Ltd., Shenyang, Liaoning (CN)

(*) Notice: Subject to any disclaimer, the term of this patent is extended or adjusted under 35 U.S.C. 154(b) by 204 days.

(21) Appl. No.: 12/990,194

(22) PCT Filed: Jun. 3, 2009

(86) PCT No.: PCT/CN2009/072101
§ 371 (c)(1),
(2), (4) Date: Oct. 28, 2010

(87) PCT Pub. No.: WO2009/146648
PCT Pub. Date: Dec. 10, 2009

(65) Prior Publication Data
US 2011/0046152 A1 Feb. 24, 2011

(30) Foreign Application Priority Data
Jun. 4, 2008 (CN) .......................... 2008 1 0114565

(51) Int. Cl.
A01N 43/40 (2006.01)
A01N 43/50 (2006.01)
C07D 213/72 (2006.01)
C07D 401/14 (2006.01)
C07D 401/02 (2006.01)

(52) U.S. Cl.
USPC ........... 504/250; 504/253; 504/260; 546/256; 546/274.7; 546/304

(58) Field of Classification Search
USPC ............... 504/250, 253, 260; 546/256, 274.7, 546/304
See application file for complete search history.

(56) References Cited

U.S. PATENT DOCUMENTS
3,394,137 A 7/1968 Morris
5,286,728 A * 2/1994 Ferrini .................... 514/255.01

FOREIGN PATENT DOCUMENTS
CN 101061103 A 10/2007
JP 2001354657 A 12/2001
WO 2008003745 A1 1/2008
WO 2008003746 A1 1/2008

OTHER PUBLICATIONS

Kumar, Shiv. Syntheses and Anthelmintic Activity of Alkyl 5(6)-(Substituted-carbamoyl) and 5(6)-(Disubstituted-carbamoyl)benzimidazole-2-carbamates and Related Compounds. J. Med. Chem. 27, (1984), 1083-1089.*

* cited by examiner

Primary Examiner — Samantha Shterengarts
(74) Attorney, Agent, or Firm — Smith, Gambrell & Russell, LLP

(57) ABSTRACT

Amide compounds, preparation methods and uses thereof. The structure of the compounds is represented as the general formula (I), in which the definitions of substituents are illuminated as description.

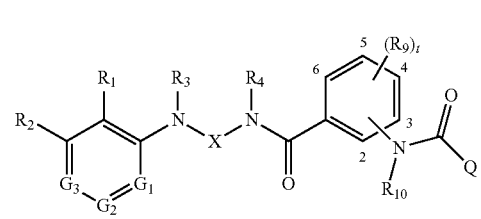

The present amide compounds have broad spectrum activity of killing pests and are effective on lepidopteran pests including *ostrinia nubilalis*, sugarcane borer, *adoxophyes orana* fischer von reslerstamm, apple fruit borer, *grapholitha inopinata*, *lymantri dispar* l., *cnaphalocrocis medinalis*, *ostrinia furnacalis*, *helicoverpa assulta*, *grapholitha inopinata*, *plutella xylostella*, *spodoptera exigua*, *prodenia litura* etc., especially for *plutella xylostella*, *spodoptera exigua*. The present amide compounds can obtain good effect at very low dosage. At the same time, some compounds have good fungicidal activity which can be used to prevent rice blast, *phytophthora infestans*, cucumber downy mildew or grey mold of vegetables.

9 Claims, No Drawings

AMIDE COMPOUNDS, PREPARATION METHODS AND USES THEREOF

FIELD OF THE INVENTION

The present invention relates to insecticide, fungicide. Specifically to amide compounds, preparation methods and uses thereof.

BACKGROUND OF THE INVENTION

The following piperazine compounds with insecticidal and fungicidal activity were known in early U.S. Pat. No. 3,394,137:

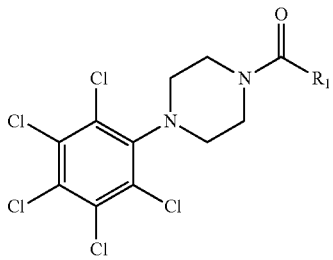

$R_1$ is selected from alkyl or haloalkyl

The following piperazine compounds with insecticidal and fungicidal activity were known in patent JP2001354657:

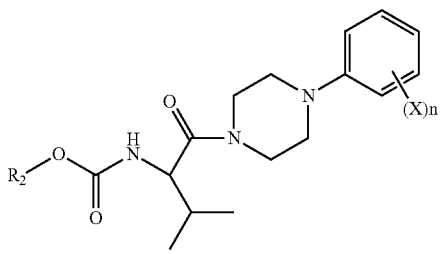

Some piperazine compounds with insecticidal and fungicidal activity as agrochemicals were also known in patents, such as JP 2006188462, US 20080076777, CN101128445, US20050032810 and US20030207894.

Some piperazine compounds with pharmaceutical activity were disclosed in patents, such as CN1040029, CN1969853, JP2003335681, U.S. Pat. No. 2,993,062, U.S. Pat. No. 5,872,115, U.S. Pat. No. 6,313,127, US2005119251, US20070027118, US2007004750, US20070190079, US2007219198, WO9728128, WO02102778, WO2004002965, WO2004078732, WO2005023260, WO2006014168, WO2006094843, WO2007009635, WO2007066784, WO2007141039 etc. and references, such as Khimiyai Khimicheskaya Tekhnologiya (2004), 47(8), 91-96; Archiv der Pharmazie (Weinheim, Germany) (2000), 333(10), 323-328.

In addition, the following compounds with fungicidal activity were known in Bayer's patents WO2008003745 and WO2008003746, separately.

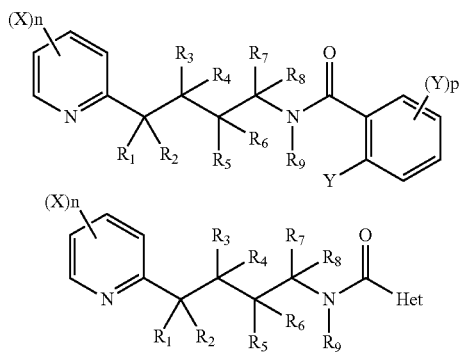

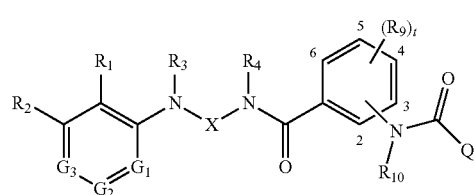

Although many piperazine and amide compounds were reported, it's still need to be researched and developed.

SUMMARY OF THE INVENTION

The aim of the present invention is to provide a novel amide compounds, which can be applied to control diseases and insects.

Detailed description of the invention is as follows:

The present invention offered an amide compounds having general formula I:

I

Wherein:
$R_1$ and $R_2$ are selected from H, OH, halogen, CN, $NO_2$, $C_1$-$C_4$alkyl, $C_1$-$C_4$haloalkyl, $C_1$-$C_4$alkoxyalkyl, $COR_{11}$, $CO_2R_{11}$, $CONR_{12}R_{11}$, $C_1$-$C_4$alkoxy, $C_1$-$C_4$haloalkoxy, $NR_{12}R_{11}$, $NR_{12}COR_{11}$, $NR_{12}CO_2R_{11}$, $SO_mR_{12}$, $SO_2NR_{12}R_{11}$, unsubstituted phenyl or substituted phenyl with substituent group(s) being from 1 to 3 in which the substituent group(s) is(are) selected from Cl, Br, F, CN, $NO_2$, $C_1$-$C_6$alkyl, $C_1$-$C_3$haloalkyl, $C_1$-$C_3$haloalkoxy or $C_1$-$C_3$alkoxycarbonyl;

m is selected from 0, 1 or 2;

$R_3$ and $R_4$ are selected from H, $C_1$-$C_6$alkyl, $C_2$-$C_6$alkenyl, $C_2$-$C_6$alkynyl, $C_3$-$C_6$cycloalkyl or $C_1$-$C_4$haloalkyl; or $R_3$ joined together with $R_4$ to form 6-8 membered ring;

X is selected from $(CHR_5)_n$; n is integers from 2 to 10; $R_5$ may be the same or different, selected from H, $C_1$-$C_6$alkyl, $C_2$-$C_6$alkenyl, $C_2$-$C_6$alkynyl, $C_3$-$C_6$cycloalkyl or $C_1$-$C_6$haloalkyl;

$G_1$ is selected from $CR_6$ or N; $G_2$ is selected from $CR_7$ or N; $G_3$ is selected from $CR_8$ or N; but $G_1$, $G_2$ and $G_3$ can not be N at the same time;

$R_6$, $R_7$ and $R_8$ are selected from H, OH, halogen, CN, $NO_2$, $C_1$-$C_4$alkyl, $C_3$-$C_6$cycloalkyl, $CONH_2$, $CONHCH_2CN$, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, $C_1$-$C_3$alkoxycarbonyl, $C_1$-$C_3$alkylcarbonyl, $C_1$-$C_3$alkylamino, $C_2$-$C_6$dialkylamino, $C_3$-$C_6$cycloalkylamino, unsubstituted phenyl or substituted phenyl with substituent group(s) being from 1 to 4, unsubstituted phenylamino or substituted phenylamino with substituent group(s) being from 1 to 4, in which the substituent group(s) is(are) selected from Cl, Br, F, CN, $NO_2$, $C_1$-$C_4$alkyl, $C_1$-$C_3$haloalkyl, $C_1$-$C_3$alkoxy, $C_1$-$C_3$haloalkoxy or $C_1$-$C_3$alkoxycarbonyl;

$R_9$ is selected from H, OH, halogen, CN, $NO_2$, $C_1$-$C_4$alkyl, $C_3$-$C_6$cycloalkyl, $C_1$-$C_3$haloalkyl, $C_1$-$C_3$alkoxyalkyl, $C_1$-$C_3$alkoxy, $C_1$-$C_3$haloalkoxy, $COR_{11}$, $CO_2R_{11}$, $CONR_{11}R_{12}$, $NR_{12}R_{11}$, $NR_{12}COR_{11}$, $NR_{12}CO_2R_{11}$, $SO_mR_{12}$, $SO_2NR_{12}R_{11}$, unsubstituted phenyl or substituted phenyl, unsubstituted pyrazolyl or substituted pyrazolyl, unsubstituted pyridyl or substituted pyridyl, in which the substituent group(s) being from 1 to 3 is(are) selected from halogen, CN, $NO_2$, $C_1$-$C_4$alkyl, $C_3$-$C_6$cycloalkyl, $C_1$-$C_3$haloalkyl, $C_1$-$C_3$alkoxyalkyl, $C_1$-$C_3$alkoxy, $C_1$-$C_3$haloalkoxy, $COR_{11}$, $CO_2R_{11}$, $CONR_{11}R_{12}$, $NR_{11}R_{12}$, $NR_{12}COR_{11}$, $NR_{12}CO_2R_{11}$, $SO_mR_{12}$ or $SO_2NR_{11}R_{12}$;

t is selected from 1, 2, 3 or 4;

$R_{10}$ and $R_{11}$ are selected from H or $C_1$-$C_4$alkyl;

$R_{12}$ is selected from H, $C_1$-$C_4$alkyl, $C_1$-$C_3$haloalkyl, unsubstituted phenyl or substituted phenyl, in which the substituent group is selected from Cl, Br, F, CN, $NO_2$, $C_1$-$C_4$alkyl, $CF_3$, $OCH_3$, $OCF_3$ or $CO_2CH_3$;

Q is selected from unsubstituted $C_1$-$C_4$alkyl or substituted $C_1$-$C_4$alkyl, unsubstituted cyclopropyl or substituted cyclopropyl, wherein the substituent group(s) being from 1 to 4 is(are) selected from Cl, Br, F or $C_1$-$C_4$alkyl; unsubstituted phenylamino or substituted phenylamino, unsubstituted $C_2$-$C_4$alkenyl or substituted $C_2$-$C_4$alkenyl, in which substituent group(s) being from 1 to 3 is(are) selected from Cl, Br, F, $C_1$-$C_4$alkyl, $C_3$-$C_6$cycloalkyl, $C_1$-$C_4$haloalkyl, $C_1$-$C_4$alkoxy, $C_1$-$C_4$haloalkoxy or $C_1$-$C_4$alkoxycarbonyl; unsubstituted phenyl or substituted phenyl, unsubstituted pyrazolyl or substituted pyrazolyl, unsubstituted pyridyl or substituted pyridyl, in which substituent group(s) being from 1 to 4 is(are) halogen, CN, $NO_2$, $C_1$-$C_4$alkyl, $C_3$-$C_6$cycloalkyl, $C_1$-$C_3$haloalkyl, $C_1$-$C_3$alkoxyalkyl, $C_1$-$C_3$alkoxy, $C_1$-$C_3$haloalkoxy, $COR_{11}$, $CO_2R_{11}$, $CONR_{11}R_{12}$, $NR_{11}R_{12}$, $NR_{12}COR_{11}$, $NR_{12}CO_2R_{11}$, $SO_mR_{12}$ or $SO_2NR_{11}R_{19}$.

The preferred compounds of general formula I of the invention are:

$R_1$ is selected from H, OH, Cl, Br, F, $NO_2$, CN, $CH_3$, $CH_2CH_3$, tert-butyl, $CF_3$, $CH_2CF_3$, $OCH_3$, $OCF_3$, $CONH_2$, $CONHCH_2CN$, $CO_2CH_3$ or $CO_2C_2H_5$;

$R_2$ is selected from H, OH, Cl, Br, F, $NO_2$, CN, $CH_3$, $CH_2CH_3$, tert-butyl, cyclopropyl, $CF_3$, $CH_2CF_3$, $OCF_3$, $OCH_2CF_3$, $CO_2CH_3$, $CO_2C_2H_5$, unsubstituted phenyl or substituted phenyl, in which substituent group(s) being from 1 to 3 is(are) Cl, Br, F, CN, $NO_2$, $CH_3$, $CH_2CH_3$, tert-butyl, $CF_3$, $CH_2CF_3$, $OCH_3$, $OCF_3$, $CO_2CH_3$ or $CO_2C_2H_5$;

$R_3$ and $R_4$ are selected from H or $C_1$-$C_3$alkyl; or $R_3$ joined together with $R_4$ to form six-membered ring;

X is selected from $(CHR_5)_n$; n is integers selected from 2 to 10; $R_5$ may be the same or different, selected from H, $C_1$-$C_3$alkyl or $C_1$-$C_3$haloalkyl;

$G_1$ is selected from $CR_6$ or N; $G_2$ is selected from $CR_7$ or N; $G_3$ is selected from $CR_8$ or N; but $G_1$, $G_2$ and $G_3$ can not be N at the same time;

$R_6$, $R_7$ and $R_8$ are selected from H, OH, Cl, Br, F, CN, $NO_2$, $CH_3$, $CH_2CH_3$, tert-butyl, cyclopropyl, $CF_3$, $CH_2CF_3$, $OCF_3$, $OCH_2CF_3$, $CO_2CH_3$, $CONH_2$, $CONHCH_2CN$, $C_1$-$C_3$alkylamino, $C_2$-$C_4$dialkylamino, $C_3$-$C_6$cycloalkylamino, unsubstituted phenyl or substituted phenyl with substituent group(s) being from 1 to 3, unsubstituted phenylamino or substituted phenylamino with substituent group(s) being from 1 to 3, wherein the substituent group(s) is(are) selected from Cl, Br, I, CN, $NO_2$, $CH_3$, $CR_2CH_3$, tert-butyl, CHF), $CF_3$, $CH_2CF_3$, $OCH_3$, $OCHF_2$, $OCF_3$, $CO_2CH_3$ or $CO_2C_2H_5$;

$R_9$ is selected from H, Cl, Br, F, CN, $NO_2$, $CH_3$, tert-butyl, $CHF_2$, $CF_3$, $OCH_3$, $OCHF_2$, $OCF_3$, $OCH_2CF_3$, $SO_2CH_3$, $C_1$-$C_3$alkylamino or $C_2$-$C_4$dialkylamino;

t is selected from 1, 2, 3 or 4;

$R_{10}$ is selected from H, $CH_3$ or $C_2H_5$;

$NR_{10}$—CO-Q is at the 2, 3 or 4-position of benzene ring;

Q is selected from one of the following groups:

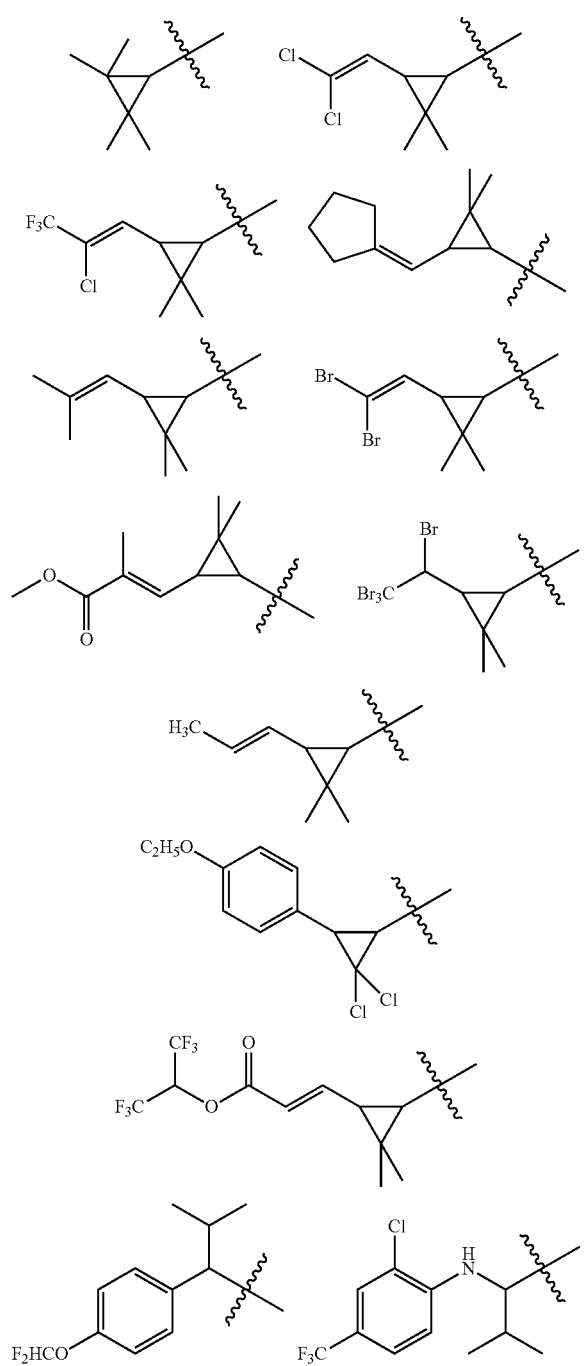

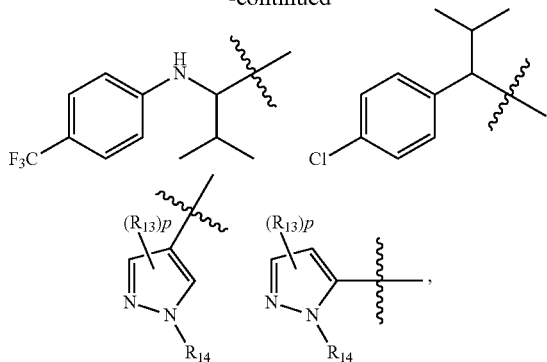

Wherein:
$R_{13}$ is selected from H, Cl, Br, F, CN, $NO_2$, $NH_2$, $CH_3$, $CH_2CH_3$, tert-butyl, cyclopropyl, $CF_3$, $CH_2CF_3$, $OCH_3$, $OCF_3$, $OCH_2CF_3$, $SO_2CH_3$, $CO_2CH_3$, $C_1$-$C_3$alkylaminocarbonyl, $C_2$-$C_4$dialkylaminocarbonyl, unsubstituted phenyl or substituted phenyl with substituent group(s) being from 1 to 3, unsubstituted pyridyl or substituted pyridyl with substituent group(s) being from 1 to 3, the substituent group(s) is(are) selected from H, Cl, Br, F, CN, $NO_2$, $CH_3$, $CH_2CH_3$, tert-butyl, cyclopropyl, $CHF_2$, $CF_3$, $CH_2CF_3$, $OCH_3$, $OCHF_2$, $OCF_3$, $OCH_2CF_3$ or $SO_2CH_3$;

$R_{14}$ is selected from H, $CH_3$, $CH_2CH_3$, tert-butyl, $CF_3$, $CH_2CF_3$, unsubstituted phenyl or substituted phenyl with substituent group(s) being from 1 to 3, unsubstituted pyridyl or substituted pyridyl with substituent group(s) being from 1 to 3, the substituent group(s) is(are) selected from Cl, Br, F, CN, $NO_2$, $CH_3$, $CH_2CH_3$, tert-butyl, cyclopropyl, $CHF_2$, $CF_3$, $CH_2CF_3$, $OCH_3$, $OCHF_2$, $OCF_3$, $OCH_2CF_3$ or $SO_2CH_3$;

p is selected from 1 or 2.

Furthermore, the preferred compounds of general formula I of the invention are:

$R_1$ is selected from H, Cl, Br, F, $NO_2$, CN, $CH_3$, $CH_2CH_3$, tert-butyl, $CF_3$, $CH_2CF_3$, $OCH_3$, $OCF_3$, $CO_2CH_3$ or $CO_2C_2H_5$;

$R_2$ is selected from H, Cl, Br, F, $NO_2$, CN, $CH_2CH_3$, tert-butyl, cyclopropyl, $CF_3$, $CH_2CF_3$, $OCF_3$, $OCH_2CF_3$, $CO_2CH_3$, $CO_2C_2H_5$, unsubstituted phenyl or substituted phenyl with the substituent group(s) being from 1 to 3 is(are) selected from Cl, Br, F, CN, $NO_2$, $CH_3$, $CH_2CH_3$, tert-butyl, $CF_3$, $CH_2CF_3$, $OCH_3$, $OCF_3$, $CO_2CH_3$ or $CO_2C_2H_5$;

$R_3$ and $R_4$ are selected from H or $C_1$-$C_3$alkyl; or $R_3$ joined together with $R_4$ to form 6 membered ring;

X is selected from $(CHR_5)_n$; n is integers selected from 2 to 10; $R_5$ may be the same or different, selected from H, $C_1$-$C_3$alkyl or $C_1$-$C_3$haloalkyl;

$G_1$ is selected from $CR_6$ or N; $G_2$ is selected from $CR_7$ or N; $G_3$ is selected from $CR_8$ or N; but $G_1$, $G_2$ and $G_3$ can not be N at the same time;

$R_6$, $R_7$ and $R_8$ are selected from H, Cl, Br, F, CN, $NO_2$, $CH_3$, $CH_2CH_3$, tert-butyl, cyclopropyl, $CF_3$, $CH_2CF_3$, $OCF_3$, $OCH_2CF_3$, $CO_2CH_3$, $C_1$-$C_3$alkylamino, $C_2$-$C_4$dialkylamino, cyclopropylamino, unsubstituted phenyl or substituted phenyl with substituent group(s) being from 1 to 3, unsubstituted phenylamino or substituted phenylamino with substituent group(s) being from 1 to 3, the substituent group(s) is(are) selected from Cl, Br, I, CN, $NO_2$, $CH_3$, $CH_2CH_3$, tert-butyl, $CHF_2$, $CF_3$, $CH_2CF_3$, $OCH_3$, $OCHF_2$, $OCF_3$, $CO_2CH_3$ or $CO_2C_2H_5$;

$R_9$ is selected from H, Cl, Br, F, CN, $NO_2$, $CHF_2$, $CF_3$, $OCH_3$, $OCHF_2$, $OCF_3$, $OCH_2CF_3$ or $SO_2CH_3$;

t is selected from 1, 2, 3 or 4;
$R_{10}$ is selected from H, $CH_3$ or $C_2H_5$;
$NR_{10}$—CO-Q is at the 2, 3 or 4-position of benzene ring;
Q is selected from one of the following groups:

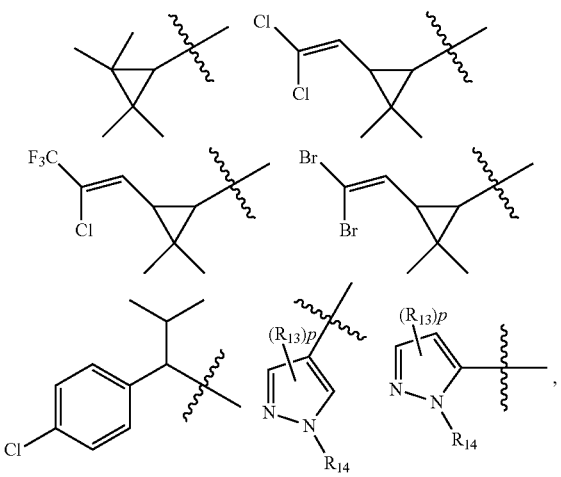

Wherein:
$R_{13}$ is selected from H, Cl, Br, F, CN, $NO_2$, $CH_3$, $CH_2CH_3$, tert-butyl, cyclopropyl, $CF_3$, $CH_2CF_3$, $OCH_3$, $OCF_3$, $OCH_2CF_3$, $SO_2CH_3$, $CO_2CH_3$, unsubstituted phenyl or substituted phenyl with substituent group(s) being from 1 to 3, unsubstituted pyridyl or substituted pyridyl with substituent group(s) being from 1 to 3, the substituent group(s) is(are) selected from H, Cl, Br, F, CN, $NO_2$, $CH_3$, $CH_2CH_3$, tert-butyl, cyclopropyl, $CHF_2$, $CF_3$, $CH_2CF_3$, $OCH_3$, $OCHF_2$, $OCF_3$, $OCH_2CF_3$ or $SO_2CH_3$;

$R_{14}$ is selected from H, $CH_3$, $CH_2CH_3$, tert-butyl, $CF_3$, $CH_2CF_3$, unsubstituted phenyl or substituted phenyl with substituent group(s) being from 1 to 3, unsubstituted pyridyl or substituted pyridyl with substituent group(s) being from 1 to 3-T, the substituent group(s) is(are) selected from Cl, Br, F, CN, $NO_2$, $CH_3$, $CH_2CH_3$, tert-butyl, cyclopropyl, $CHF_2$, $CF_3$, $CH_2CF_3$, $OCH_3$, $OCHF_2$, $OCF_3$, $OCH_2CF_3$ or $SO_2CH_3$;

p is selected from 1 or 2.

Even more preferred compounds of general formula I of the invention are:

$R_1$ is selected from 1-1, Cl, Br, F, $NO_2$, CN, $CH_3$, tert-butyl, $CF_3$, $OCH_3$ or $OCF_3$;

$R_2$ is selected from H, Cl, Br, F, $NO_2$, CN, $CH_3$, tert-butyl, cyclopropyl, $CF_3$, $OCF_3$, $CO_2CH_3$ or $CO_2C_2H_5$;

$R_3$ and $R_4$ are selected from H or $C_1$-$C_3$alkyl; or $R_3$ joined together with $R_4$ to form 6 membered ring;

X is selected from —$CH_2CH_2$—, —$CH_2CH_2CH_2$—, —$CH(CH_3)CH_2$—, —$CH(CH_2)_5CH_2$—, —$CH_2(CH_2)_2CH_2$—, —$CH_2(CH_2)_3CH_2$—, —$CH_2(CH_2)_4CH_2$—, —$CH_2(CH_2)_5CH_2$—, —$CH_2(CH_2)_6CH_2$—, —$CH_2(CH_2)_7CH_2$— or —$CH_2(CH_2)_8CH_2$—;

$G_1$ is selected from $CR_6$ or N; $G_2$ is selected from $CR_7$ or N; $G_3$ is selected from $CR_8$ or N; but $G_1$, $G_2$ and $G_3$ can not be N at the same time;

$R_6$, $R_7$ and $R_8$ are selected from H, Cl, Br, F, CN, $NO_2$, $CH_3$, $CH_2CH_3$, tert-butyl, cyclopropyl, $CF_3$, $CH_2CF_3$, $OCF_3$, $OCH_2CF_3$ or $CO_2CH_3$;

$R_9$ is selected from H, Cl, Br, F, CN, $NO_2$, $CH_3$, $CHF_2$, $CF_3$, $OCH_3$, $OCHF_2$, $OCF_3$, $OCH_2CF_3$ or $SO_2CH_3$;

t is selected from 1, 2, 3 or 4;

$R_{10}$ is selected from H;

$NR_{10}$—CO-Q is at the 2, 3 or 4-position of benzene ring;

Q is selected from one of the following groups:

[Chemical structures shown: substituted cyclopropyl groups with Cl, F₃C/Cl, Br substituents; chlorophenyl isopropyl group; two pyrazolyl groups with $(R_{13})p$ and $R_{14}$ substituents]

Wherein:

$R_{14}$ is selected from H, $CH_3$, unsubstituted phenyl or substituted phenyl with substituent group(s) being from 1 to 3, unsubstituted pyridyl or substituted pyridyl with substituent group(s) being from 1 to 3, in which the substituent group(s) is(are) selected from Cl, Br, F, CN, $NO_2$, $CH_3$, $CH_2CH_3$, tert-butyl, $CF_3$, $OCH_3$ or $OCF_3$;

When $R_{14}$ is selected from H or $CH_3$, $R_{43}$ is selected from H, Cl, Br, F, CN, $CH_3$, $CH_2CH_3$, tert-butyl, cyclopropyl, $CF_3$, $OCH_3$, $OCF_3$, $OCH_2CF_3$, $SO_2CH_3$, unsubstituted phenyl or substituted phenyl, the substituent group is selected from H, Cl, Br, F, CN, $NO_2$, $CH_3$, $CH_2CH_3$, tert-butyl, $CHF_2$, $CF_3$, $OCH_3$, $OCHF_2$, $OCF_3$, $OCH_2CF_3$ or $SO_2CH_3$;

When $R_{14}$ is selected from (un)substituted phenyl or pyridyl, $R_{13}$ is selected from H, Cl, Br, F, CN, $CH_3$, $CH_2CH_3$, tert-butyl, cyclopropyl, $CF_3$, $OCF_3$, $OCH_2CF_3$ or $SO_2CH_3$;

p is selected from 1 or 2.

Most preferred compounds of general formula I of the invention are:

$R_1$ is selected from H, Cl, Br, F, $NO_2$, CN, $CH_3$ or $CF_3$;

$R_2$ is selected from 1-1., Cl, Br, F, $NO_2$, CN, $CH_3$, tert-butyl, cyclopropyl, $CF_3$, $OCF_3$, $CO_2CH_3$ or $CO_2C_2H_5$;

$R_3$ and $R_4$ are selected from H, or $R_3$ and $R_4$ in $(R_3)N$—X—$N(R_4)$ can join together to form piperazine ring;

X is selected from —$CH_2CH_2$—, —$CH_2CH_2CH_2$—, —$CH(CH_3)CH_2$—, —$CH(C_2H_5)CH_2$—, —$CH_2(CH_2)_2CH_2$—, —$CH_2(CH_2)_3CH_2$—, —$CH_2(CH_2)_4CH_2$—, —$CH_2(CH_2)_5CH_2$—, —$CH_2(CH_2)_6CH_2$—, —$CH_2(CH_2)_7CH_2$— or —$CH_2(CH_2)_8CH_2$—;

$G_1$ is selected from $CR_6$ or N; $G_2$ is selected from $CR_7$ or N; $G_3$ is selected from $CR_8$ or N; but $G_1$, $G_2$ and $G_3$ can not be N at the same time;

$R_6$, $R_7$ and $R_8$ are selected from H, Cl, Br, F, CN, $NO_2$, $CH_3$, $CH_2CH_3$, tert-butyl, cyclopropyl, $CF_3$, $OCH_3$ or $CO_2CH_3$;

$R_9$ is selected from H, Cl, Br, F, CN, $NO_2$, $CH_3$, $CHF_2$, $CF_3$, $OCH_3$, $OCHF_2$, $OCF_3$, $OCH_2CF_3$ or $SO_2CH_3$;

t is selected from 1 or 2;

$R_{10}$ is selected from H;

$NR_{10}$—CO-Q is at the 2 or 4-position of benzene ring;

Q is selected from the following pyrazolyl groups:

[Pyrazole structure with $(R_{13})p$ and $R_{14}$ substituents]

Wherein:

$R_{14}$ is selected from H, $CH_3$, unsubstituted phenyl or substituted phenyl with substituent group(s) being from 1 to 3, unsubstituted pyridyl or substituted pyridyl both with substituent group(s) being from 1 to 3, the substituent group(s) is(are) selected from Cl, Br, F, CN, $NO_2$, $CH_3$, $CH_2CH_3$, tert-butyl, $CF_3$, $OCH_3$ or $OCF_3$;

When $R_{14}$ is selected from H or $CH_3$, $R_{43}$ is selected from H, Cl, Br, F, CN, $CH_3$, $CH_2CH_3$, tert-butyl, $CF_3$, $OCH_3$, $OCF_3$, $SO_2CH_3$, unsubstituted phenyl or substituted phenyl with substituent group, the substituent group is selected from H, Cl, Br, F, CN, $NO_2$, $CH_3$, $CH_2CH_3$, tert-butyl, $CHF_2$, $CF_3$, $OCH_3$, $OCHF_2$, $OCF_3$ or $SO_2CH_3$;

When $R_{14}$ is selected from (un)substituted phenyl or pyridyl, $R_{13}$ is selected from H, Cl, Br, F, CN, $CH_3$, $CH_2CH_3$, tert-butyl, $CF_3$, $OCH_3$, $OCF_3$ or $SO_2CH_3$;

p is selected from 1 or 2.

The Q groups of the general formula I in present invention are listed in Table 1:

TABLE 1

| | |
|---|---|
| $Q_1$ | [pyrazole with methyl groups, N-methyl] |
| $Q_2$ | [pyrazole with Cl, methyl groups, N-methyl] |
| $Q_3$ | [pyrazole with methyl group, N-CH₂CF₃] |
| $Q_4$ | [pyrazole with methyl group, N-tert-butyl] |

TABLE 1-continued
| | |
|---|---|
| Q5 | 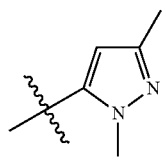 [SMILES: *c1cc(C)nn1C] |
| Q6 | 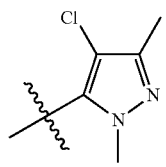 [SMILES: *c1c(Cl)c(C)nn1C] |
| Q7 | 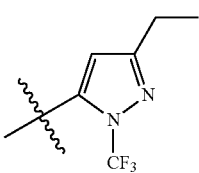 [SMILES: *c1cc(CC)nn1C(F)(F)F] |
| Q8 | 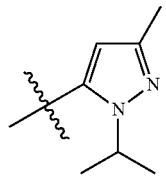 [SMILES: *c1cc(C)nn1C(C)C] |
| Q9 | 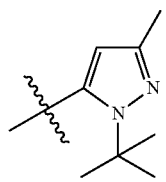 [SMILES: *c1cc(C)nn1C(C)(C)C] |
| Q10 | 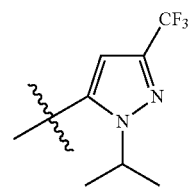 [SMILES: *c1cc(C(F)(F)F)nn1C(C)C] |
| Q11 | 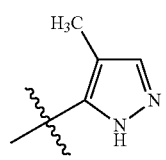 |
| Q12 | 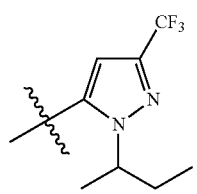 [SMILES: *c1cc(C(F)(F)F)nn1C(C)CC] |
| Q13 | 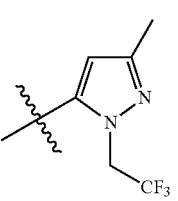 [SMILES: *c1cc(C)nn1CC(F)(F)F] |
| Q14 | 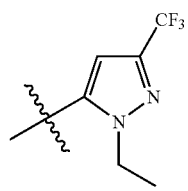 [SMILES: *c1cc(C(F)(F)F)nn1CC] |
| Q15 | 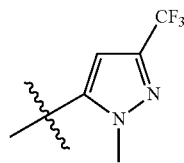 [SMILES: *c1cc(C(F)(F)F)nn1C] |
| Q16 | 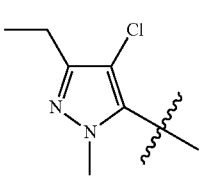 [SMILES: *c1c(Cl)c(CC)nn1C] |
| Q17 | 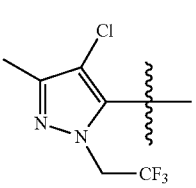 [SMILES: *c1c(Cl)c(C)nn1CC(F)(F)F] |
| Q18 | 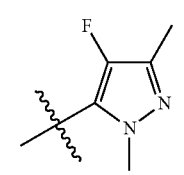 [SMILES: *c1c(F)c(C)nn1C] |
| Q19 | 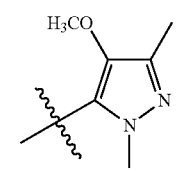 [SMILES: *c1c(OC)c(C)nn1C] |
| Q20 | 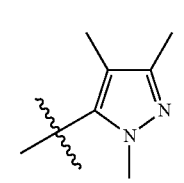 [SMILES: *c1c(C)c(C)nn1C] |
| Q21 | 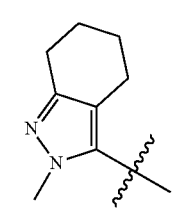 [SMILES: *c1c2c(nn1C)CCCC2] |

TABLE 1-continued
| | |
|---|---|
| Q22 | 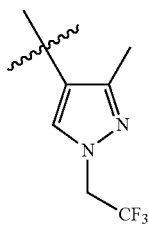 [SMILES: *c1cn(CC(F)(F)F)nc1C] |
| Q23 | 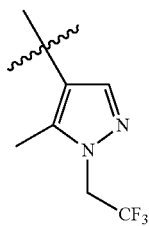 [SMILES: *c1cnn(CC(F)(F)F)c1C] |
| Q24 | 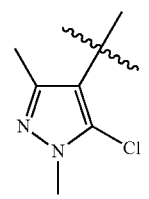 [SMILES: *c1c(C)nn(C)c1Cl] |
| Q25 | 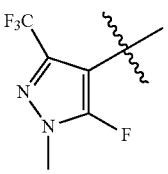 |
| Q26 | 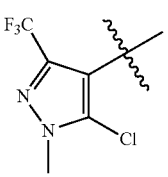 |
| Q27 | 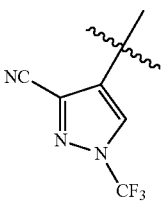 |
| Q28 | 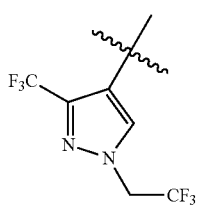 |
| Q29 | 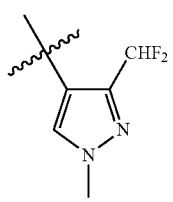 [SMILES: *c1cn(C)nc1C(F)F] |
| Q30 | 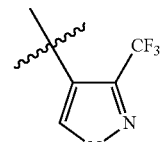 |
| Q31 | 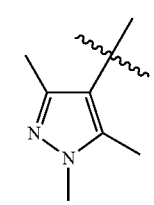 |
| Q32 | 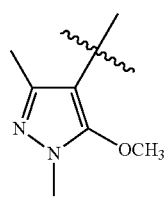 [SMILES: *c1c(C)nn(C)c1OC] |
| Q33 | 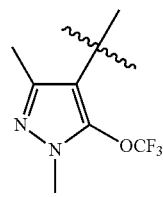 [SMILES: *c1c(C)nn(C)c1OC(F)(F)F] |
| Q34 | 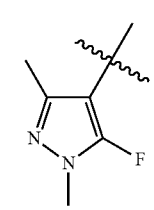 [SMILES: *c1c(C)nn(C)c1F] |
| Q35 | 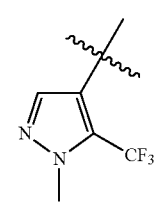 |
| Q36 | 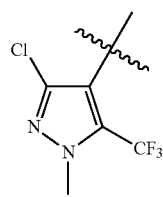 [SMILES: *c1c(Cl)nn(C)c1C(F)(F)F] |
| Q37 | 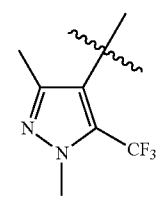 [SMILES: *c1c(C)nn(C)c1C(F)(F)F] |

TABLE 1-continued
Q38 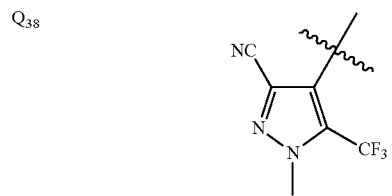
Q39 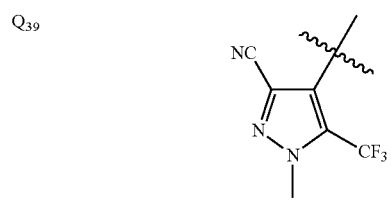
Q40 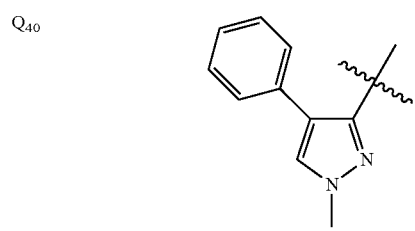
Q41 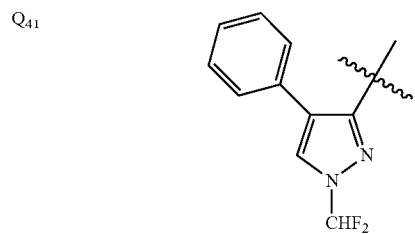
Q42 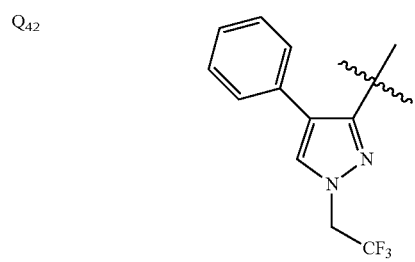
Q43 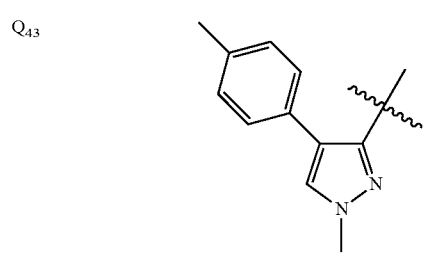
TABLE 1-continued
Q44 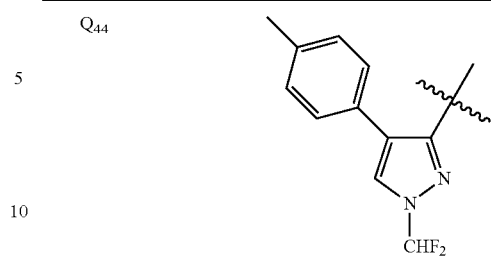
Q45 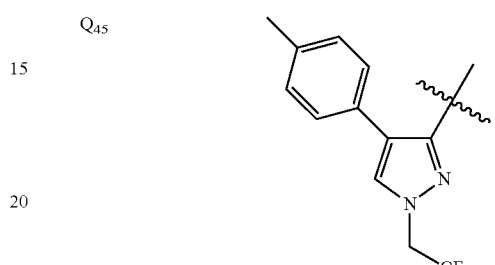
Q46 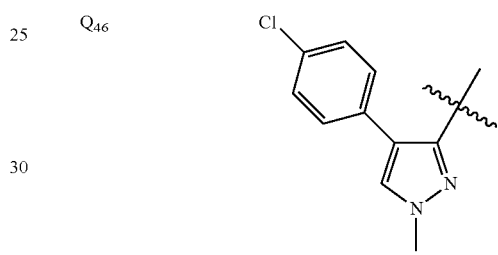
Q47 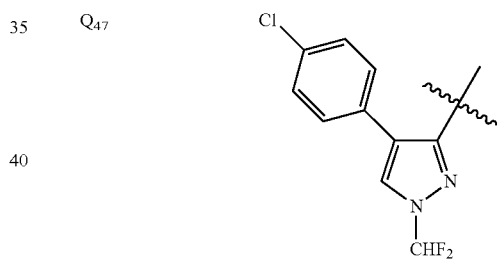
Q48 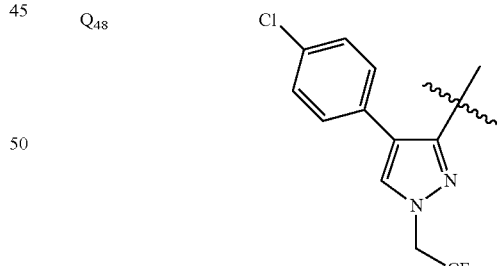
Q49 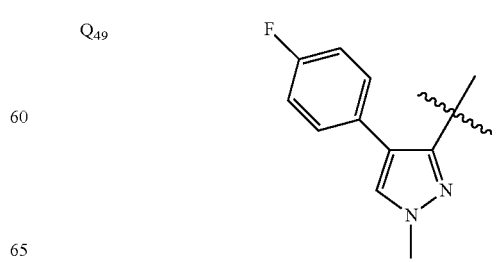

TABLE 1-continued
| Q50 | 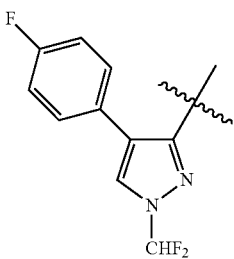 [SMILES: *c1nn(C(F)F)cc1-c1ccc(F)cc1] |
| Q51 | 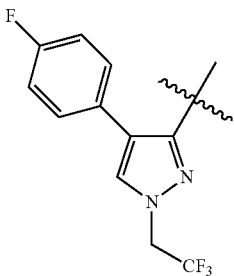 [SMILES: *c1nn(CC(F)(F)F)cc1-c1ccc(F)cc1] |
| Q52 | 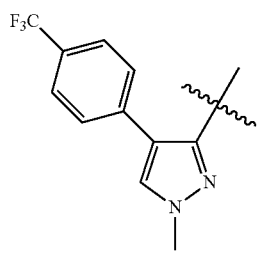 [SMILES: *c1nn(C)cc1-c1ccc(C(F)(F)F)cc1] |
| Q53 | 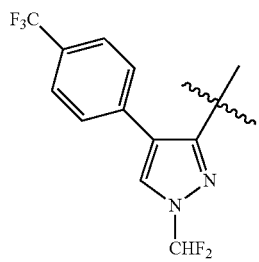 [SMILES: *c1nn(C(F)F)cc1-c1ccc(C(F)(F)F)cc1] |
| Q54 | 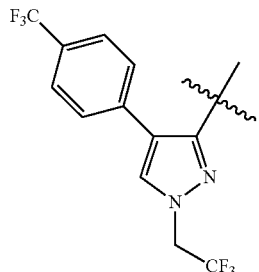 |
| Q55 | 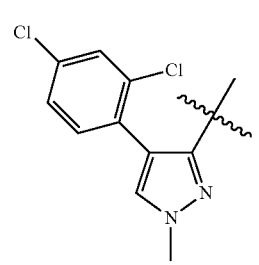 [SMILES: *c1nn(C)cc1-c1ccc(Cl)cc1Cl] |
TABLE 1-continued
| Q56 | 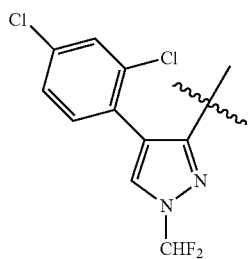 [SMILES: *c1nn(C(F)F)cc1-c1ccc(Cl)cc1Cl] |
| Q57 | 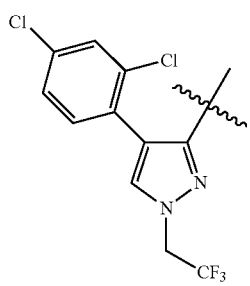 [SMILES: *c1nn(CC(F)(F)F)cc1-c1ccc(Cl)cc1Cl] |
| Q58 | 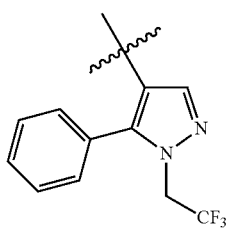 [SMILES: *c1cnn(CC(F)(F)F)c1-c1ccccc1] |
| Q59 | 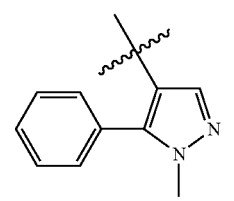 [SMILES: *c1cnn(C)c1-c1ccccc1] |
| Q60 | 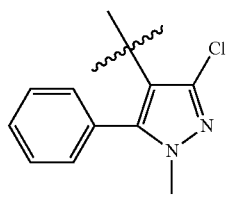 [SMILES: *c1c(Cl)nn(C)c1-c1ccccc1] |
| Q61 | 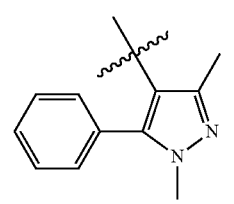 [SMILES: *c1c(C)nn(C)c1-c1ccccc1] |
| Q62 | 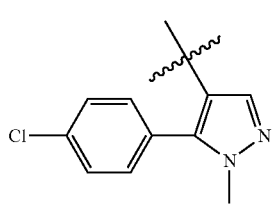 [SMILES: *c1cnn(C)c1-c1ccc(Cl)cc1] |

TABLE 1-continued
| | |
|---|---|
| Q63 | 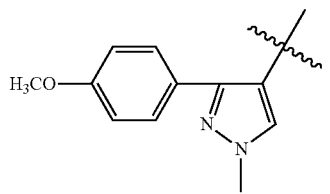 [SMILES: *c1cn(C)nc1-c1ccc(OC)cc1] |
| Q64 | 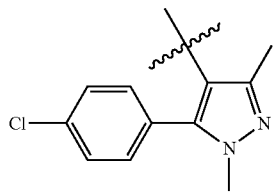 [SMILES: *c1c(C)nn(C)c1-c1ccc(Cl)cc1] |
| Q65 | 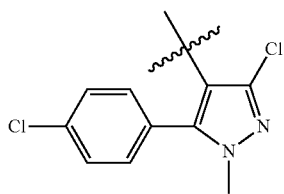 [SMILES: *c1c(Cl)nn(C)c1-c1ccc(Cl)cc1] |
| Q66 | 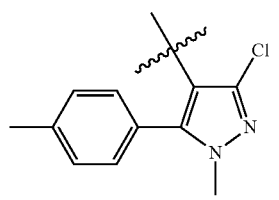 [SMILES: *c1c(Cl)nn(C)c1-c1ccc(C)cc1] |
| Q67 | 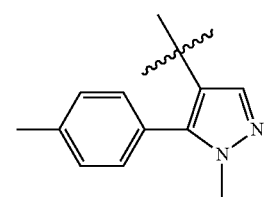 [SMILES: *c1cnn(C)c1-c1ccc(C)cc1] |
| Q68 | 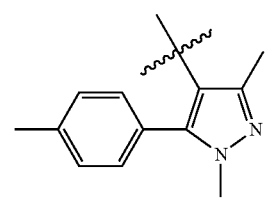 |
| Q69 | 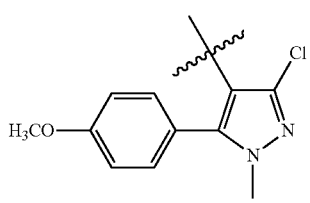 [SMILES: *c1c(Cl)nn(C)c1-c1ccc(OC)cc1] |
| Q70 | 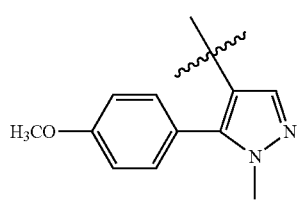 [SMILES: *c1cnn(C)c1-c1ccc(OC)cc1] |
| Q71 | 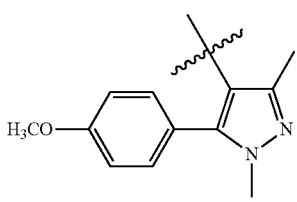 [SMILES: *c1c(C)nn(C)c1-c1ccc(OC)cc1] |
| Q72 | 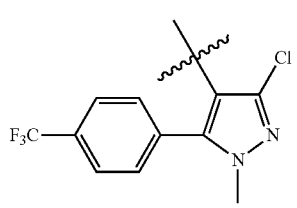 [SMILES: *c1c(Cl)nn(C)c1-c1ccc(C(F)(F)F)cc1] |
| Q73 | 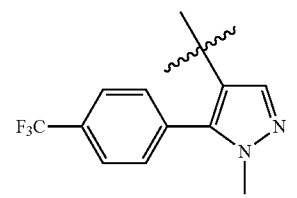 [SMILES: *c1cnn(C)c1-c1ccc(C(F)(F)F)cc1] |
| Q74 | 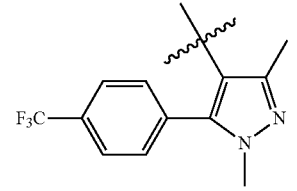 [SMILES: *c1c(C)nn(C)c1-c1ccc(C(F)(F)F)cc1] |
| Q75 | 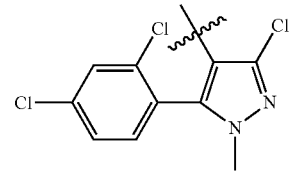 [SMILES: *c1c(Cl)nn(C)c1-c1ccc(Cl)cc1Cl] |
| Q76 | 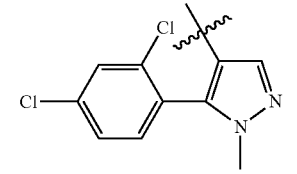 [SMILES: *c1cnn(C)c1-c1ccc(Cl)cc1Cl] |
| Q77 | 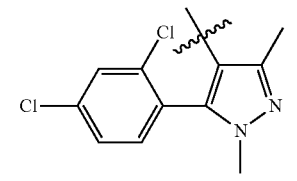 [SMILES: *c1c(C)nn(C)c1-c1ccc(Cl)cc1Cl] |
| Q78 | 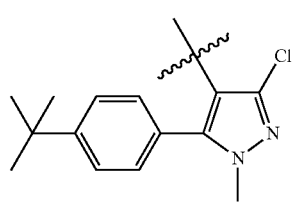 [SMILES: *c1c(Cl)nn(C)c1-c1ccc(C(C)(C)C)cc1] |

TABLE 1-continued
Q79 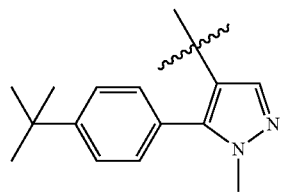 [SMILES: *c1cnn(C)c1-c1ccc(C(C)(C)C)cc1]
Q80 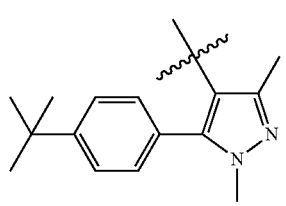 [SMILES: *c1c(C)nn(C)c1-c1ccc(C(C)(C)C)cc1]
Q81 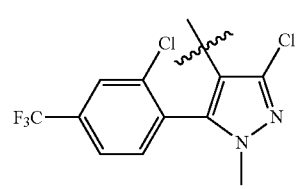 [SMILES: *c1c(Cl)nn(C)c1-c1ccc(C(F)(F)F)cc1Cl]
Q82 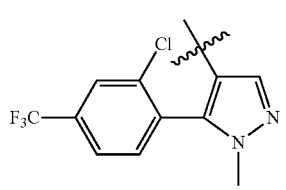 [SMILES: *c1cnn(C)c1-c1ccc(C(F)(F)F)cc1Cl]
Q83 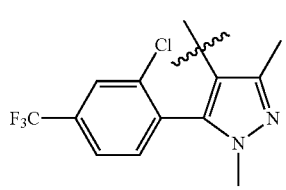 [SMILES: *c1c(C)nn(C)c1-c1ccc(C(F)(F)F)cc1Cl]
Q84 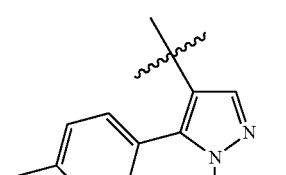
Q85 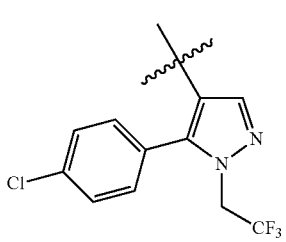 [SMILES: *c1cnn(CC(F)(F)F)c1-c1ccc(Cl)cc1]
Q86 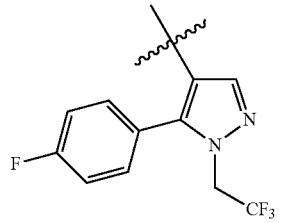 [SMILES: *c1cnn(CC(F)(F)F)c1-c1ccc(F)cc1]
Q87 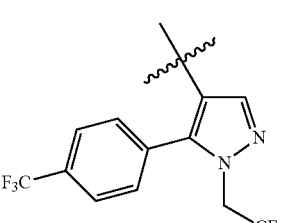
Q88 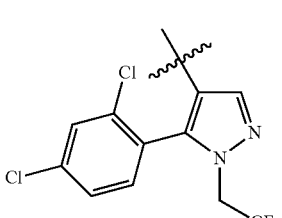
Q89 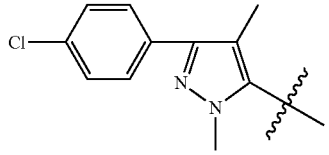 [SMILES: *c1c(C)c(-c2ccc(Cl)cc2)nn1C]
Q90 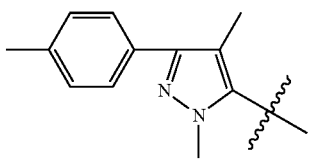 [SMILES: *c1c(C)c(-c2ccc(C)cc2)nn1C]
Q91 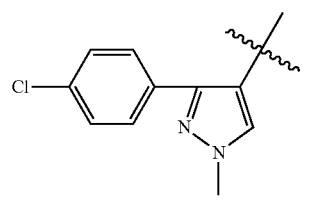
Q92 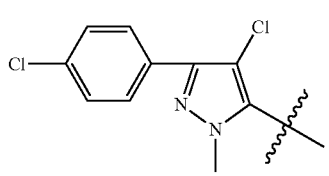 [SMILES: *c1c(Cl)c(-c2ccc(Cl)cc2)nn1C]
Q93 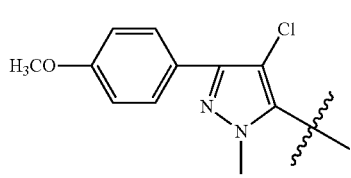 [SMILES: *c1c(Cl)c(-c2ccc(OC)cc2)nn1C]

TABLE 1-continued
Q94 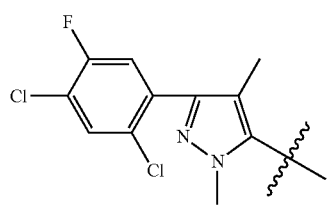 [SMILES: *c1c(C)c(-c2cc(F)c(Cl)cc2Cl)nn1C]
Q95 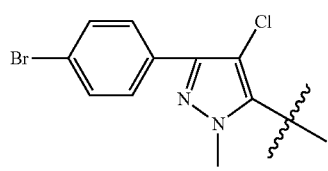
Q96 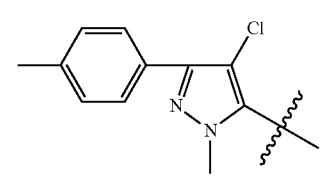 [SMILES: *c1c(Cl)c(-c2ccc(C)cc2)nn1C]
Q97 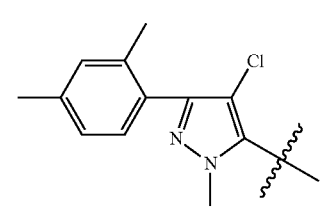
Q98 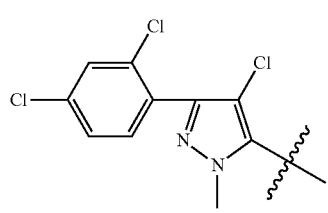 [SMILES: *c1c(Cl)c(-c2ccc(Cl)cc2Cl)nn1C]
Q99 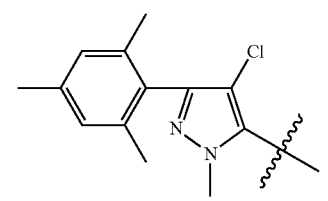 [SMILES: *c1c(Cl)c(-c2c(C)cc(C)cc2C)nn1C]
Q100 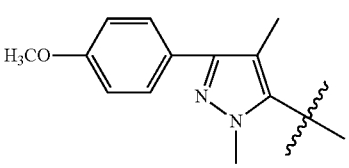 [SMILES: *c1c(C)c(-c2ccc(OC)cc2)nn1C]
Q101 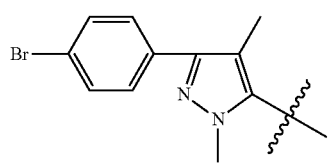
TABLE 1-continued
Q102 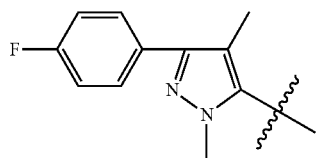 [SMILES: *c1c(C)c(-c2ccc(F)cc2)nn1C]
Q103 
Q104 
Q105 
Q106 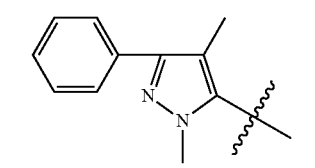 [SMILES: *c1c(C)c(-c2ccccc2)nn1C]
Q107 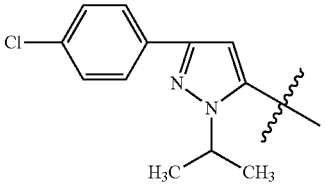 [SMILES: *c1cc(-c2ccc(Cl)cc2)nn1C(C)C]
Q108 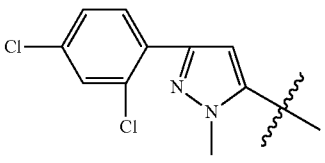 [SMILES: *c1cc(-c2ccc(Cl)cc2Cl)nn1C]
Q109 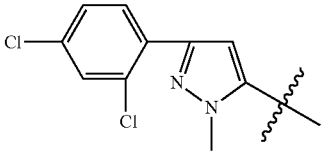 [SMILES: *c1cc(-c2ccc(Cl)cc2Cl)nn1C]
Q110 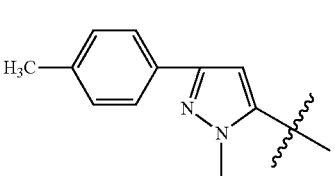 [SMILES: *c1cc(-c2ccc(C)cc2)nn1C]

TABLE 1-continued
| | |
|---|---|
| Q111 | 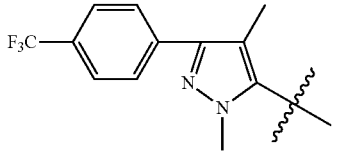 [SMILES: *c1c(C)c(-c2ccc(C(F)(F)F)cc2)nn1C] |
| Q112 | 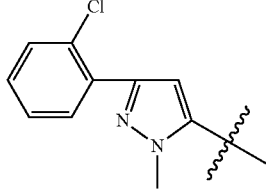 [SMILES: *c1cc(-c2ccccc2Cl)nn1C] |
| Q113 | 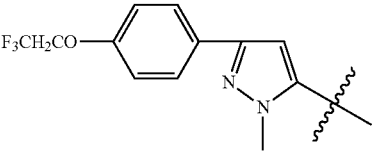 |
| Q114 | 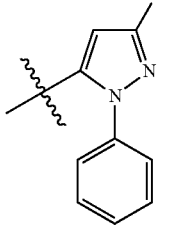 |
| Q115 | 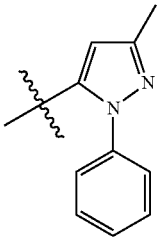 [SMILES: *c1cc(C)nn1-c1ccccc1] |
| Q116 | 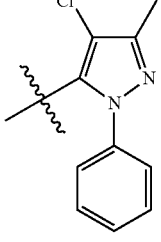 |
| Q117 | 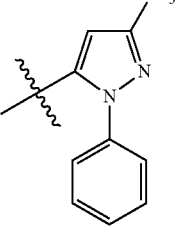 |
| Q118 | 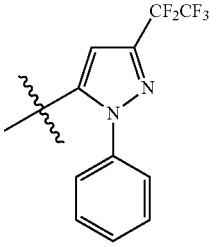 |
| Q119 | 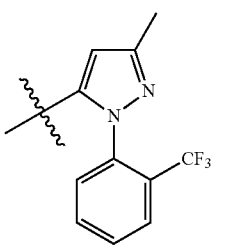 [SMILES: *c1cc(C)nn1-c1ccccc1C(F)(F)F] |
| Q120 | 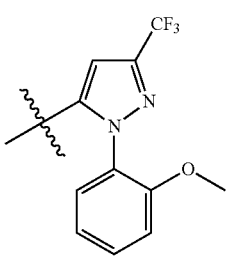 [SMILES: *c1cc(C(F)(F)F)nn1-c1ccccc1OC] |
| Q121 | 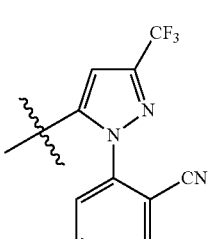 |
| Q122 | 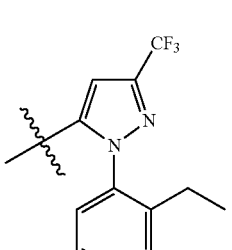 |
| Q123 | 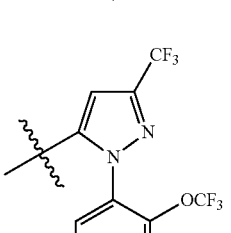 |

TABLE 1-continued
Q124 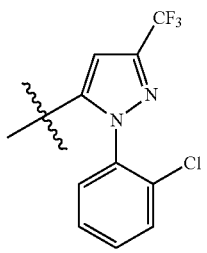 [SMILES: *c1cc(C(F)(F)F)nn1-c1ccccc1Cl]
Q125 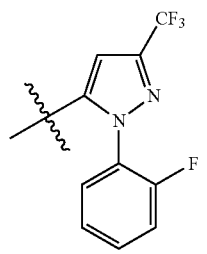 [SMILES: *c1cc(C(F)(F)F)nn1-c1ccccc1F]
Q126 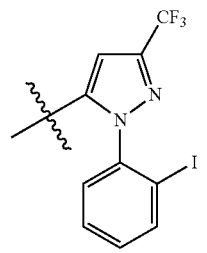 [SMILES: *c1cc(C(F)(F)F)nn1-c1ccccc1I]
Q127 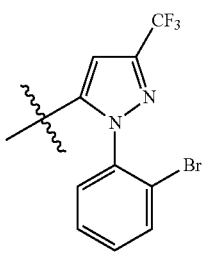 [SMILES: *c1cc(C(F)(F)F)nn1-c1ccccc1Br]
Q128 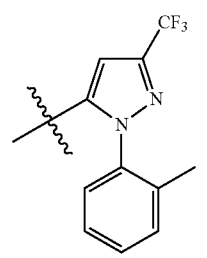 [SMILES: *c1cc(C(F)(F)F)nn1-c1ccccc1C]
Q129 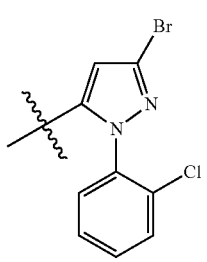 [SMILES: *c1cc(Br)nn1-c1ccccc1Cl]
Q130 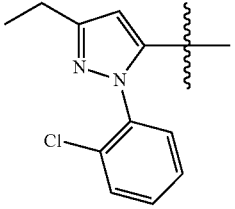 [SMILES: *c1cc(CC)nn1-c1ccccc1Cl]
Q131 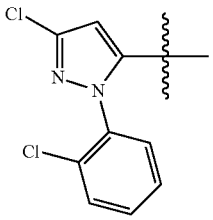 [SMILES: *c1cc(Cl)nn1-c1ccccc1Cl]
Q132 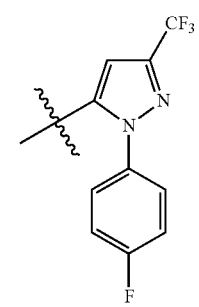 [SMILES: *c1cc(C(F)(F)F)nn1-c1ccc(F)cc1]
Q133 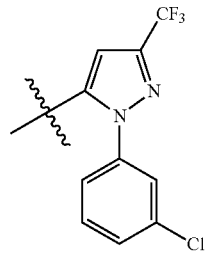 [SMILES: *c1cc(C(F)(F)F)nn1-c1cccc(Cl)c1]
Q134 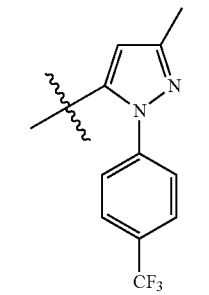 [SMILES: *c1cc(C)nn1-c1ccc(C(F)(F)F)cc1]
Q135 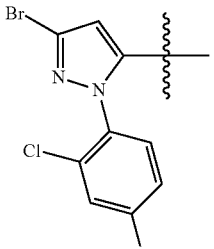

TABLE 1-continued
| | | | | |
|---|---|---|---|---|
| Q136 | 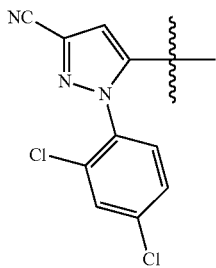 [SMILES: *c1cc(C#N)nn1-c1ccc(Cl)cc1Cl] | | Q142 | 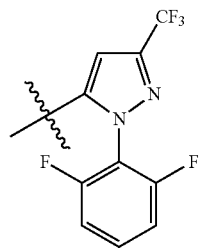 |
| Q137 | 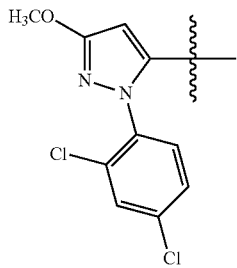 [SMILES: *c1cc(OC)nn1-c1ccc(Cl)cc1Cl] | | Q143 | 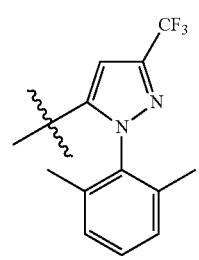 |
| Q138 | 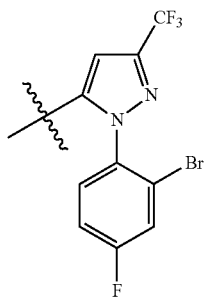 [SMILES: *c1cc(C(F)(F)F)nn1-c1ccc(F)cc1Br] | | Q144 | 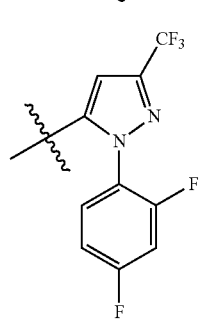 |
| Q139 | 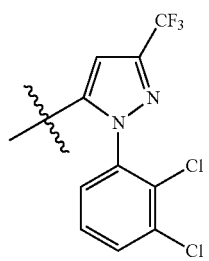 [SMILES: *c1cc(C(F)(F)F)nn1-c1cccc(Cl)c1Cl] | | Q145 | 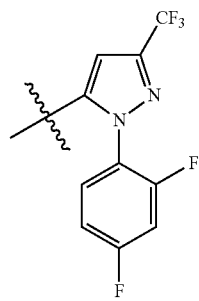 |
| Q140 | 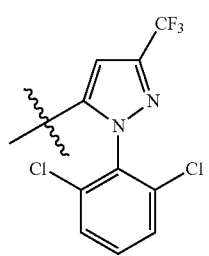 [SMILES: *c1cc(C(F)(F)F)nn1-c1c(Cl)cccc1Cl] | | Q146 | 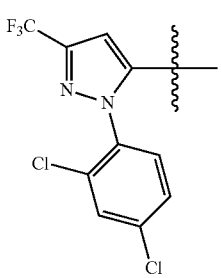 |
| Q141 | 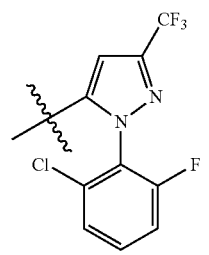 [SMILES: *c1cc(C(F)(F)F)nn1-c1c(F)cccc1Cl] | | Q147 | 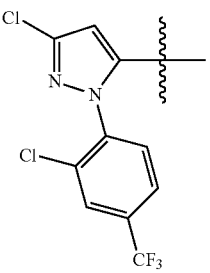 [SMILES: *c1cc(Cl)nn1-c1ccc(C(F)(F)F)cc1Cl] |

TABLE 1-continued
| Q148 | 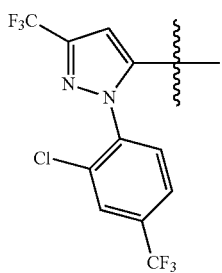 [SMILES: *c1cc(C(F)(F)F)nn1-c1ccc(C(F)(F)F)cc1Cl] |
| Q149 | 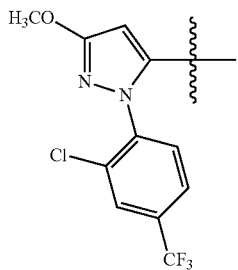 [SMILES: *c1cc(OC)nn1-c1ccc(C(F)(F)F)cc1Cl] |
| Q150 | 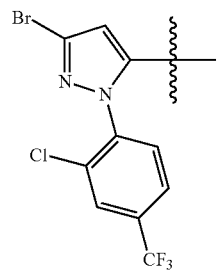 [SMILES: *c1cc(Br)nn1-c1ccc(C(F)(F)F)cc1Cl] |
| Q151 | 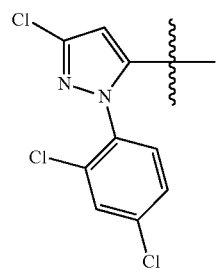 [SMILES: *c1cc(Cl)nn1-c1ccc(Cl)cc1Cl] |
| Q152 | 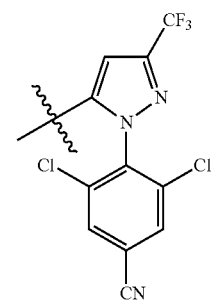 [SMILES: *c1cc(C(F)(F)F)nn1-c1c(Cl)cc(C#N)cc1Cl] |
TABLE 1-continued
| Q153 | 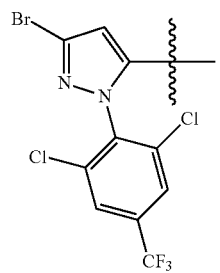 [SMILES: *c1cc(Cl)nn1-c1c(Cl)cc(C(F)(F)F)cc1Cl] |
| Q154 | 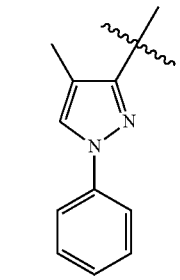 [SMILES: *c1nn(-c2ccccc2)cc1C] |
| Q155 | 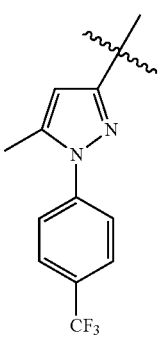 [SMILES: *c1cc(C)n(-c2ccc(C(F)(F)F)cc2)n1] |
| Q156 | 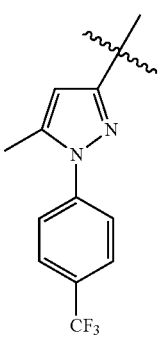 [SMILES: *c1cc(C)n(-c2ccc(C(F)(F)F)cc2)n1] |
| Q157 | 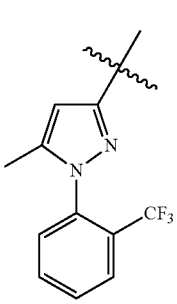 [SMILES: *c1cc(C)n(-c2ccccc2C(F)(F)F)n1] |

TABLE 1-continued
| Q158 | 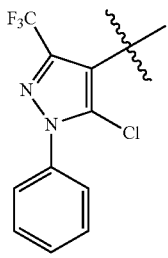 | Q164 | 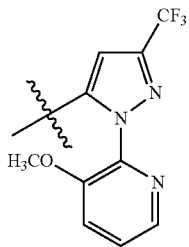 |
| Q159 | 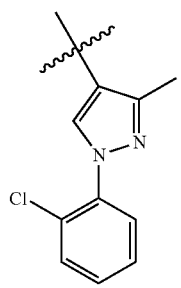 [SMILES: *c1cn(-c2ccccc2Cl)nc1C] | Q165 | 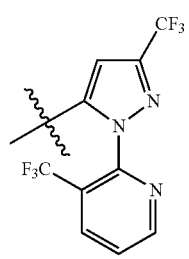 |
| Q160 | 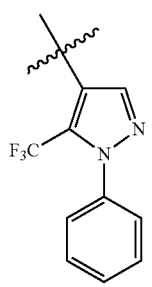 [SMILES: *c1cnn(-c2ccccc2)c1C(F)(F)F] | Q166 | 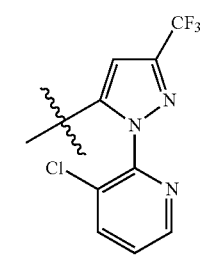 |
| Q161 | 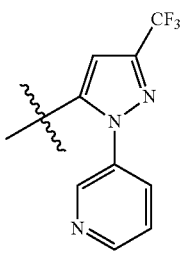 [SMILES: *c1cc(C(F)(F)F)nn1-c1cccnc1] | Q167 | 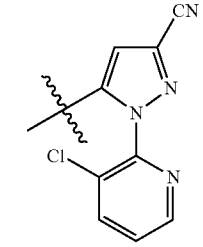 |
| Q162 | 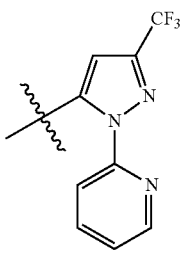 [SMILES: *c1cc(C(F)(F)F)nn1-c1ccccn1] | Q168 | 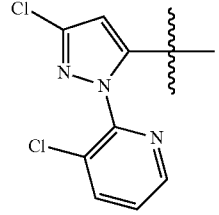 |
| Q163 | 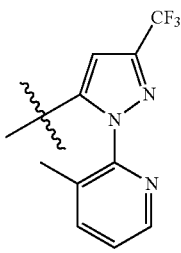 [SMILES: *c1cc(C(F)(F)F)nn1-c1ncccc1C] | Q169 | 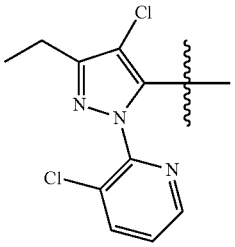 |

TABLE 1-continued
Q170 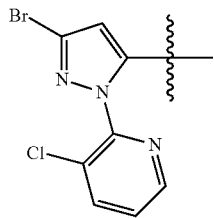 [SMILES: *c1cc(Cl)nn1-c1ncccc1Cl]
Q171 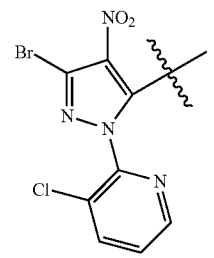 [SMILES: *c1c([N+](=O)[O-])c(Br)nn1-c1ncccc1Cl]
Q172 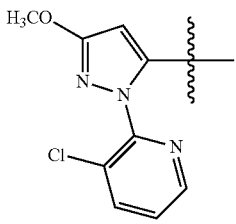 [SMILES: *c1cc(OC)nn1-c1ncccc1Cl]
Q173 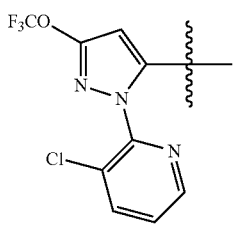 [SMILES: *c1cc(OC(F)(F)F)nn1-c1ncccc1Cl]
Q174 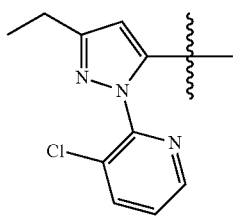 [SMILES: *c1cc(CC)nn1-c1ncccc1Cl]
Q175 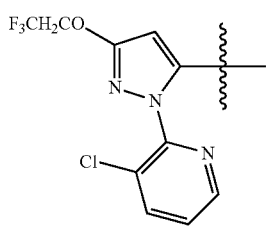
Q176 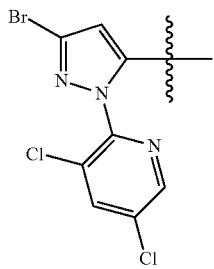
Q177 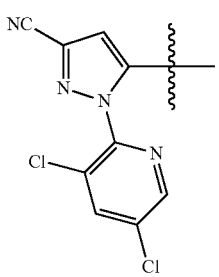 [SMILES: *c1cc(C#N)nn1-c1ncc(Cl)cc1Cl]
Q178 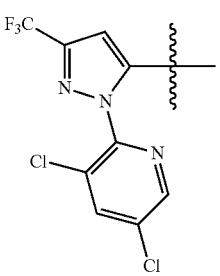
Q179 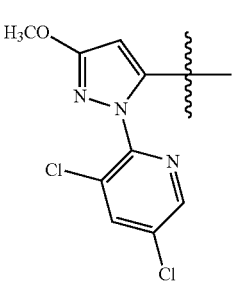
Q180 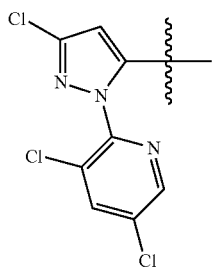 [SMILES: *c1cc(Cl)nn1-c1ncc(Cl)cc1Cl]
Q181 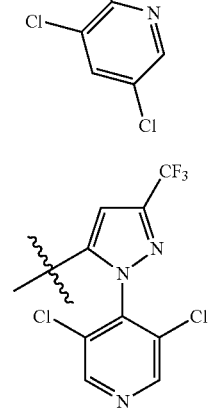

TABLE 1-continued
| | |
|---|---|
| Q182 | 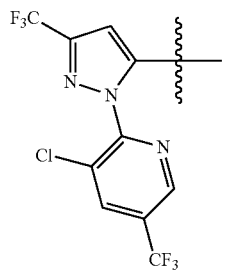 |
| Q183 | 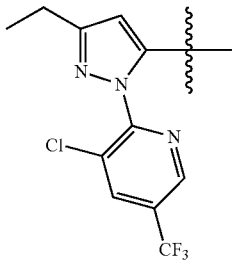 |
| Q184 | 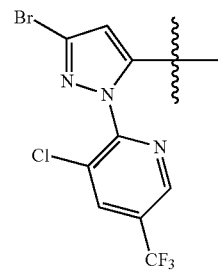 |
| Q185 | 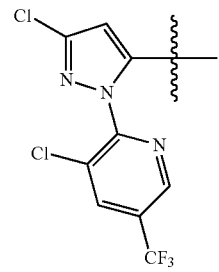 [SMILES: *c1cc(Cl)nn1-c1ncc(C(F)(F)F)cc1Cl] |
| Q186 | 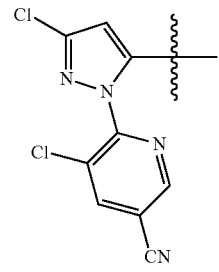 [SMILES: *c1cc(Cl)nn1-c1ncc(C#N)cc1Cl] |
| Q187 | 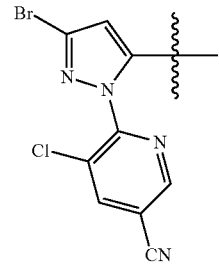 [SMILES: *c1cc(Br)nn1-c1ncc(C#N)cc1Cl] |
| Q188 | 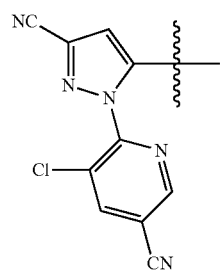 [SMILES: *c1cc(C#N)nn1-c1ncc(C#N)cc1Cl] |
| Q189 | 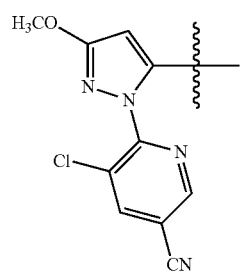 |
| Q190 | 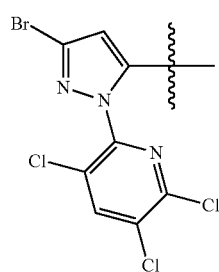 [SMILES: *c1cc(Br)nn1-c1nc(Cl)c(Cl)cc1Cl] |
| Q191 | 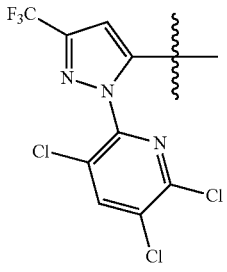 [SMILES: *c1cc(C(F)(F)F)nn1-c1nc(Cl)c(Cl)cc1Cl] |
| Q192 | 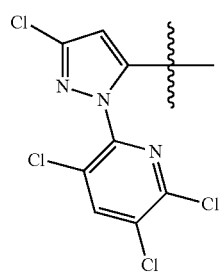 [SMILES: *c1cc(Cl)nn1-c1nc(Cl)c(Cl)cc1Cl] |

TABLE 1-continued
| | |
|---|---|
| Q193 | 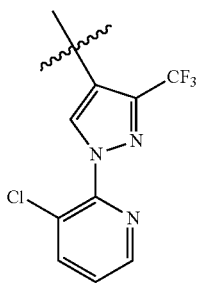 [SMILES: *c1cn(-c2ncccc2Cl)nc1C(F)(F)F] |
| Q194 | 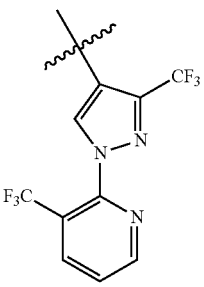 [SMILES: *c1cn(-c2ncccc2C#N)nc1C(F)(F)F] |
| Q195 | 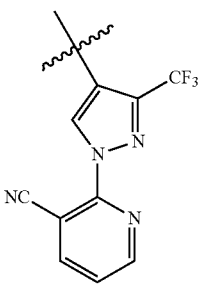 |
| Q196 | 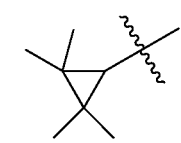 [SMILES: *C1C(C)(C)C1(C)C] |
| Q197 | 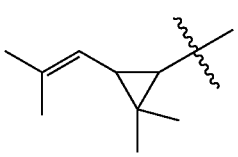 [SMILES: *C1C(C=C(C)C)C1(C)C] |
| Q198 | 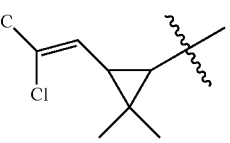 |
| Q199 | 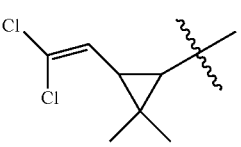 |
| Q200 | 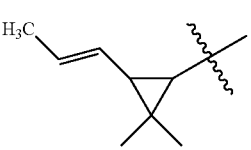 [SMILES: *C1C(/C=C/C)C1(C)C] |
TABLE 1-continued
| | |
|---|---|
| Q201 | 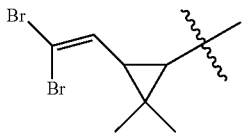 [SMILES: *C1C(C=C(Br)Br)C1(C)C] |
| Q202 | 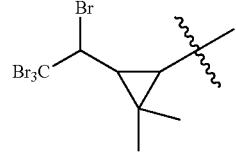 |
| Q203 | 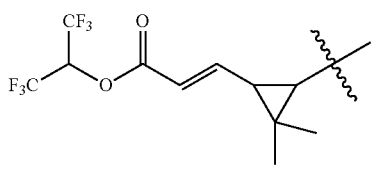 [SMILES: *C1C(/C=C/C(=O)OC(C(F)(F)F)C(F)(F)F)C1(C)C] |
| Q204 | 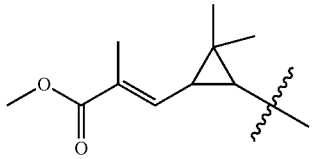 [SMILES: *C1C(/C=C(\C)C(=O)OC)C1(C)C] |
| Q205 | 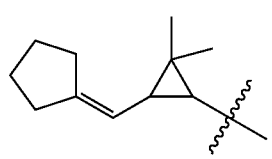 [SMILES: *C1C(C=C2CCCC2)C1(C)C] |
| Q206 | 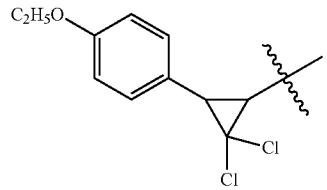 |
| Q207 | 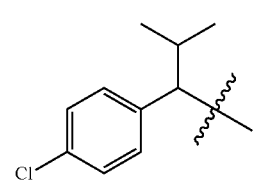 [SMILES: *C(c1ccc(Cl)cc1)C(C)C] |
| Q208 | 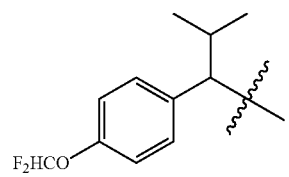 [SMILES: *C(c1ccc(OC(F)F)cc1)C(C)C] |
| Q209 | 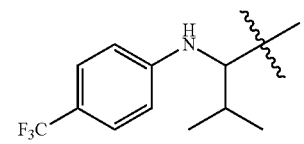 |

TABLE 1-continued
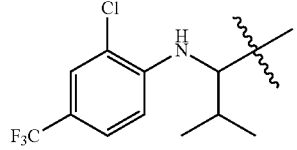 [SMILES: *C(Nc1ccc(C(F)(F)F)cc1Cl)C(C)C]
Q210
When R9 is selected from H, halogen, CN, CH3, CF3, OCH; or OCHF2, the amide compounds of the general formula I can be defined as formula I-1 to 1-29.
I-1
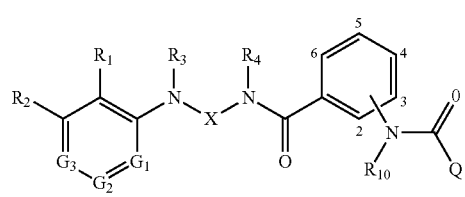
I-2
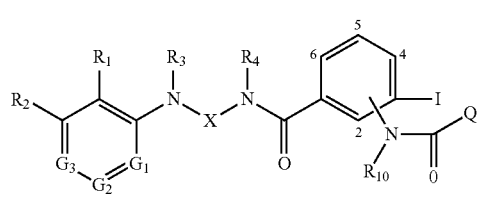
I-3
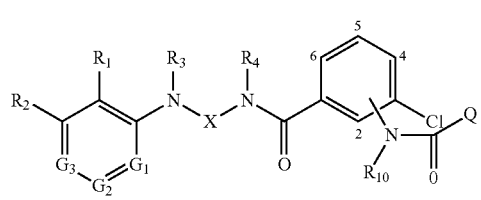
I-4
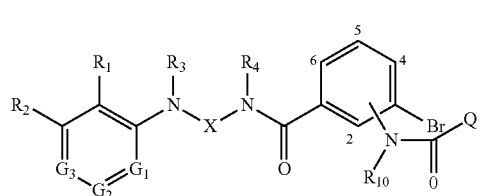
I-5
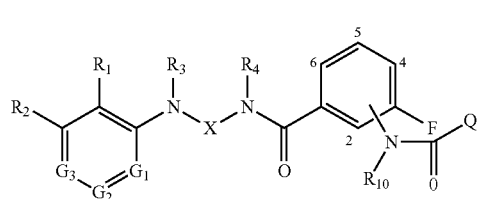
I-6
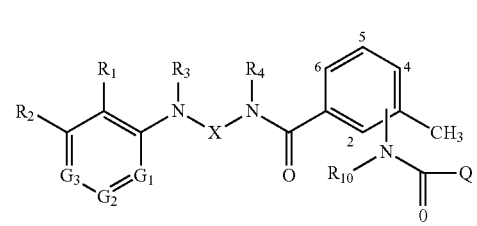
I-7
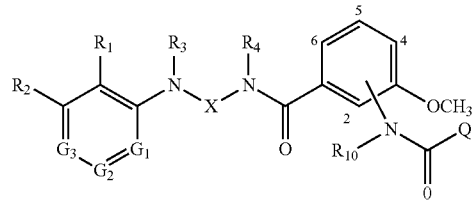
I-8
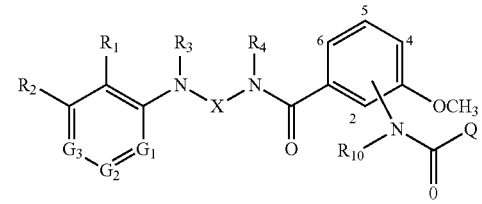
I-9
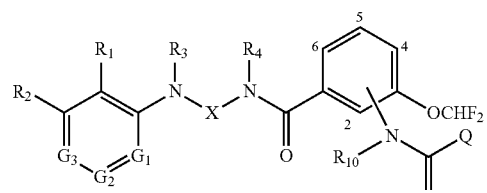
I-10
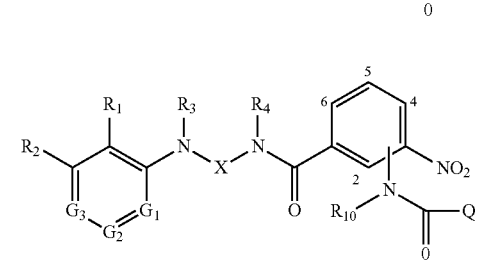
I-11
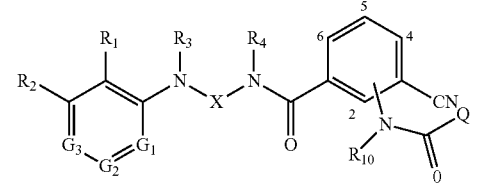
I-12
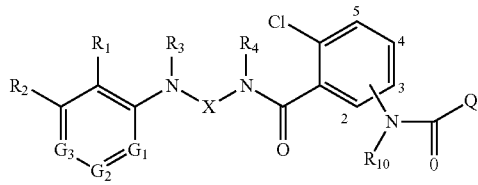
I-13
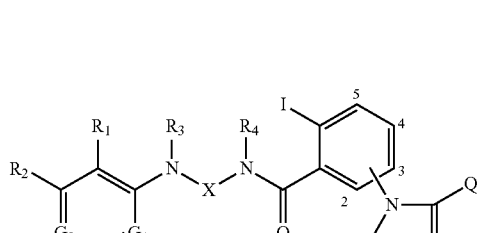
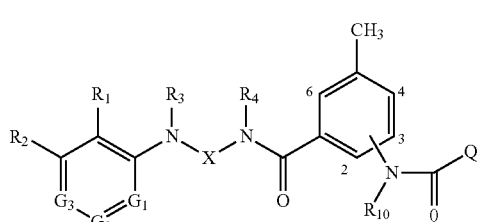

I-14
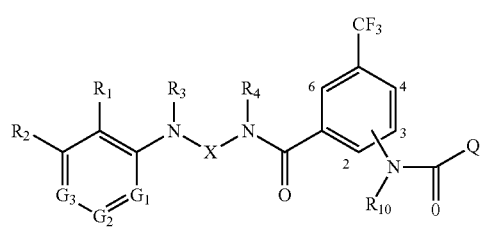
I-15
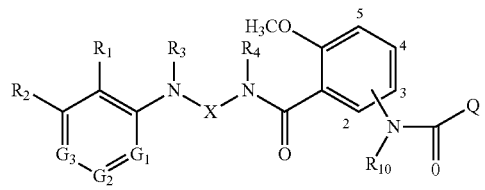
I-16
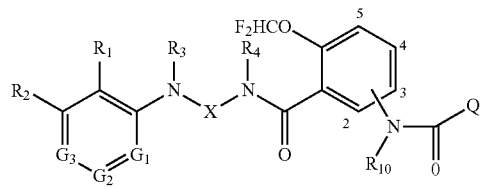
I-17
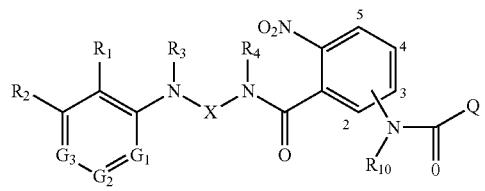
I-18
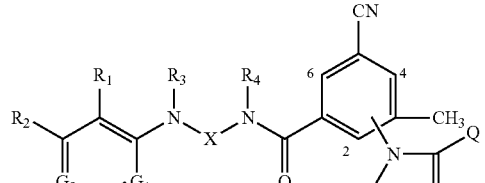
I-19
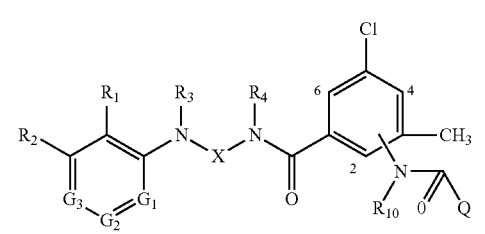
I-20
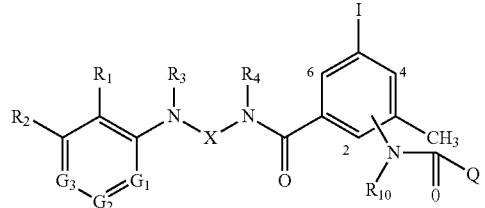
I-21
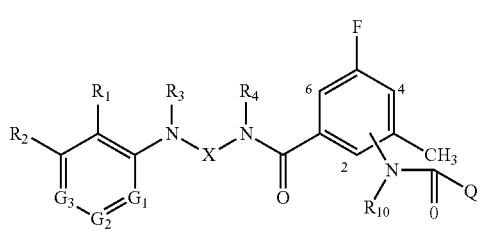
I-22
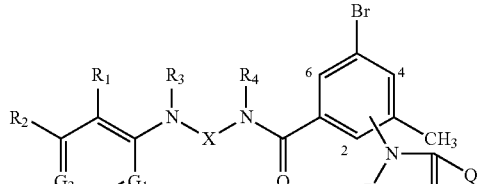
I-23
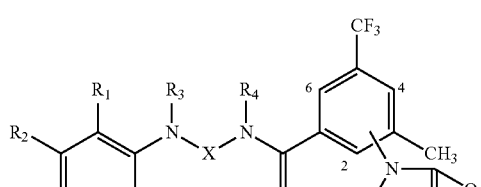
I-24
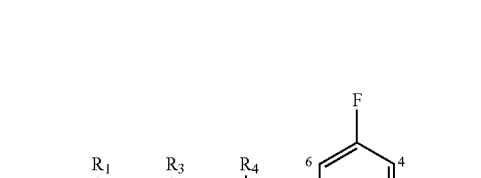
I-25
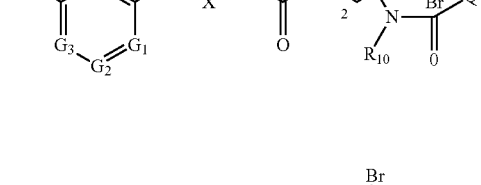
I-26
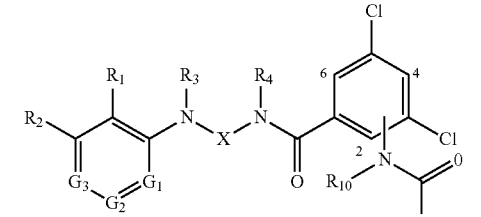

-continued

I-27
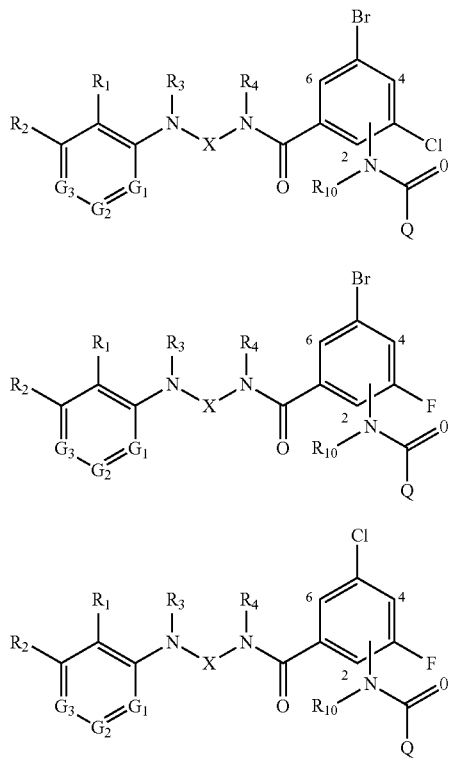

I-28
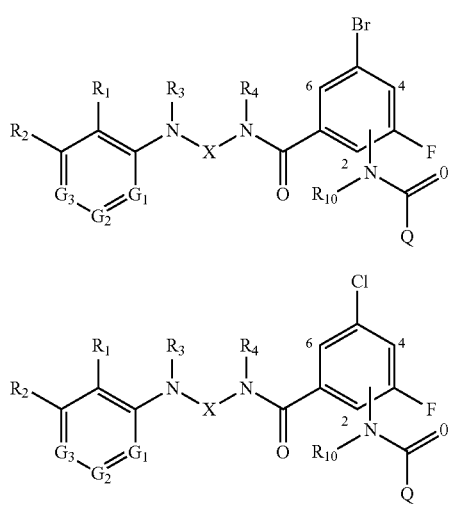

I-29
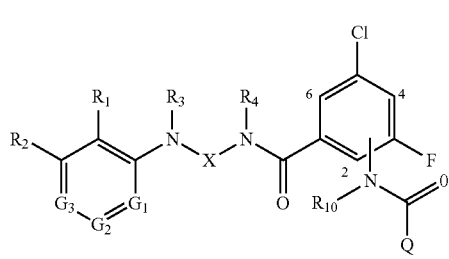

The present invention is also explained by the following compounds in Table 2 to Table 295, but without being restricted thereby.

Table 2: In formula I-1, $NR_{10}$—CO-Q is at the 2-position, $G_1$ is $CR_6$, $G_2$ is $CR_7$, $G_3$ is $CR_8$, $X=(CHR_5)_n$, $R_1$, $R_2$, $R_6$ and $R_7$ are H, $R_8$ is Cl; $R_3$, $R_4$, $R_5$, $R_{10}$, n and Q are listed in following Table 2.

TABLE 2

| No. | $R_3$ | $R_4$ | $R_5$ | $R_{10}$ | n | Q |
|---|---|---|---|---|---|---|
| 1 | H | H | H | H | 2 | $Q_6$ |
| 2 | H | H | H | H | 3 | $Q_{175}$ |
| 3 | H | H | H | H | 2 | $Q_{16}$ |
| 4 | H | H | H | H | 3 | $Q_{176}$ |
| 5 | H | H | H | H | 2 | $Q_{20}$ |
| 6 | H | H | H | H | 3 | $Q_{184}$ |
| 7 | H | H | H | H | 2 | $Q_{21}$ |
| 8 | H | H | H | H | 3 | $Q_{185}$ |
| 9 | H | H | H | H | 2 | $Q_{24}$ |
| 10 | H | H | H | H | 3 | $Q_{186}$ |
| 11 | H | H | H | H | 2 | $Q_{25}$ |
| 12 | H | H | H | H | 3 | $Q_{187}$ |
| 13 | H | H | H | H | 2 | $Q_{26}$ |
| 14 | H | H | H | H | 3 | $Q_{196}$ |
| 15 | H | H | H | H | 2 | $Q_{30}$ |
| 16 | H | H | H | H | 3 | $Q_{197}$ |
| 17 | H | H | H | H | 2 | $Q_{31}$ |
| 18 | H | H | H | H | 3 | $Q_{198}$ |
| 19 | H | H | H | H | 2 | $Q_{32}$ |
| 20 | H | H | H | H | 3 | $Q_{199}$ |
| 21 | H | H | H | H | 2 | $Q_{34}$ |
| 22 | H | H | H | H | 3 | $Q_{200}$ |
| 23 | H | H | H | H | 2 | $Q_{35}$ |
| 24 | H | H | H | H | 3 | $Q_{201}$ |
| 25 | H | H | H | H | 2 | $Q_{40}$ |
| 26 | H | H | H | H | 3 | $Q_{206}$ |
| 27 | H | H | H | H | 2 | $Q_{46}$ |
| 28 | H | H | H | H | 3 | $Q_{207}$ |

TABLE 2-continued

| No. | $R_3$ | $R_4$ | $R_5$ | $R_{10}$ | n | Q |
|---|---|---|---|---|---|---|
| 29 | H | H | H | H | 2 | $Q_{59}$ |
| 30 | H | H | H | H | 4 | $Q_6$ |
| 31 | H | H | H | H | 2 | $Q_{60}$ |
| 32 | H | H | H | H | 4 | $Q_{89}$ |
| 33 | H | H | H | H | 2 | $Q_{61}$ |
| 34 | H | H | H | H | 4 | $Q_{91}$ |
| 35 | H | H | H | H | 2 | $Q_{62}$ |
| 36 | H | H | H | H | 4 | $Q_{117}$ |
| 37 | H | H | H | H | 2 | $Q_{89}$ |
| 38 | H | H | H | H | 4 | $Q_{168}$ |
| 39 | H | H | H | H | 2 | $Q_{90}$ |
| 40 | H | H | H | H | 4 | $Q_{169}$ |
| 41 | H | H | H | H | 2 | $Q_{91}$ |
| 42 | H | H | H | H | 4 | $Q_{170}$ |
| 43 | H | H | H | H | 2 | $Q_{90}$ |
| 44 | H | H | H | H | 4 | $Q_{184}$ |
| 45 | H | H | H | H | 2 | $Q_{92}$ |
| 46 | H | H | H | H | 4 | $Q_{185}$ |
| 47 | H | H | H | H | 2 | $Q_{114}$ |
| 48 | H | H | H | H | 4 | $Q_{186}$ |
| 49 | H | H | H | H | 2 | $Q_{115}$ |
| 50 | H | H | H | H | 4 | $Q_{187}$ |
| 51 | H | H | H | H | 2 | $Q_{116}$ |
| 52 | H | H | H | H | 5 | $Q_6$ |
| 53 | H | H | H | H | 2 | $Q_{117}$ |
| 54 | H | H | H | H | 5 | $Q_{89}$ |
| 55 | H | H | H | H | 2 | $Q_{124}$ |
| 56 | H | H | H | H | 5 | $Q_{91}$ |
| 57 | H | H | H | H | 2 | $Q_{129}$ |
| 58 | H | H | H | H | 5 | $Q_{117}$ |
| 59 | H | H | H | H | 2 | $Q_{130}$ |
| 60 | H | H | H | H | 5 | $Q_{168}$ |
| 61 | H | H | H | H | 2 | $Q_{131}$ |
| 62 | H | H | H | H | 5 | $Q_{169}$ |
| 63 | H | H | H | H | 2 | $Q_{145}$ |
| 64 | H | H | H | H | 5 | $Q_{170}$ |
| 65 | H | H | H | H | 2 | $Q_{146}$ |
| 66 | H | H | H | H | 5 | $Q_{184}$ |
| 67 | H | H | H | H | 2 | $Q_{147}$ |
| 68 | H | H | H | H | 5 | $Q_{185}$ |
| 69 | H | H | H | H | 2 | $Q_{148}$ |
| 70 | H | H | H | H | 5 | $Q_{186}$ |
| 71 | H | H | H | H | 2 | $Q_{149}$ |
| 72 | H | H | H | H | 5 | $Q_{187}$ |
| 73 | H | H | H | H | 2 | $Q_{150}$ |
| 74 | H | H | H | H | 6 | $Q_6$ |
| 75 | H | H | H | H | 2 | $Q_{153}$ |
| 76 | H | H | H | H | 6 | $Q_{89}$ |
| 77 | H | H | H | H | 2 | $Q_{158}$ |
| 78 | H | H | H | H | 6 | $Q_{91}$ |
| 79 | H | H | H | H | 2 | $Q_{168}$ |
| 80 | H | H | H | H | 6 | $Q_{117}$ |
| 81 | H | H | H | H | 2 | $Q_{169}$ |
| 82 | H | H | H | H | 6 | $Q_{168}$ |
| 83 | H | H | H | H | 2 | $Q_{170}$ |
| 84 | H | H | H | H | 6 | $Q_{169}$ |
| 85 | H | H | H | H | 2 | $Q_{171}$ |
| 86 | H | H | H | H | 6 | $Q_{170}$ |
| 87 | H | H | H | H | 2 | $Q_{174}$ |
| 88 | H | H | H | H | 6 | $Q_{184}$ |
| 89 | H | H | H | H | 2 | $Q_{175}$ |
| 90 | H | H | H | H | 6 | $Q_{185}$ |
| 91 | H | H | H | H | 2 | $Q_{176}$ |
| 92 | H | H | H | H | 6 | $Q_{186}$ |
| 93 | H | H | H | H | 2 | $Q_{184}$ |
| 94 | H | H | H | H | 6 | $Q_{187}$ |
| 95 | H | H | H | H | 2 | $Q_{185}$ |
| 96 | H | H | H | H | 7 | $Q_6$ |
| 97 | H | H | H | H | 2 | $Q_{186}$ |
| 98 | H | H | H | H | 7 | $Q_{89}$ |
| 99 | H | H | H | H | 2 | $Q_{187}$ |
| 100 | H | H | H | H | 7 | $Q_{91}$ |
| 101 | H | H | H | H | 2 | $Q_{196}$ |
| 102 | H | H | H | H | 7 | $Q_{117}$ |
| 103 | H | H | H | H | 2 | $Q_{197}$ |
| 104 | H | H | H | H | 7 | $Q_{168}$ |
| 105 | H | H | H | H | 2 | $Q_{198}$ |
| 106 | H | H | H | H | 7 | $Q_{169}$ |
| 107 | H | H | H | H | 2 | $Q_{199}$ |
| 108 | H | H | H | H | 7 | $Q_{170}$ |

TABLE 2-continued

| No. | | | | | | Q |
|---|---|---|---|---|---|---|
| 109 | H | H | H | H | 2 | $Q_{200}$ |
| 110 | H | H | H | H | 7 | $Q_{184}$ |
| 111 | H | H | H | H | 2 | $Q_{201}$ |
| 112 | H | H | H | H | 7 | $Q_{185}$ |
| 113 | H | H | H | H | 2 | $Q_{206}$ |
| 114 | H | H | H | H | 7 | $Q_{186}$ |
| 115 | H | H | H | H | 2 | $Q_{207}$ |
| 116 | H | H | H | H | 7 | $Q_{187}$ |
| 117 | H | H | H | H | 3 | $Q_6$ |
| 118 | H | H | H | H | 8 | $Q_6$ |
| 119 | H | H | H | H | 3 | $Q_{16}$ |
| 120 | H | H | H | H | 8 | $Q_{89}$ |
| 121 | H | H | H | H | 3 | $Q_{20}$ |
| 122 | H | H | H | H | 8 | $Q_{91}$ |
| 123 | H | H | H | H | 3 | $Q_{21}$ |
| 124 | H | H | H | H | 8 | $Q_{117}$ |
| 125 | H | H | H | H | 3 | $Q_{24}$ |
| 126 | H | H | H | H | 8 | $Q_{168}$ |
| 127 | H | H | H | H | 3 | $Q_{25}$ |
| 128 | H | H | H | H | 8 | $Q_{169}$ |
| 129 | H | H | H | H | 3 | $Q_{26}$ |
| 130 | H | H | H | H | 8 | $Q_{170}$ |
| 131 | H | H | H | H | 3 | $Q_{30}$ |
| 132 | H | H | H | H | 8 | $Q_{184}$ |
| 133 | H | H | H | H | 3 | $Q_{31}$ |
| 134 | H | H | H | H | 8 | $Q_{185}$ |
| 135 | H | H | H | H | 3 | $Q_{32}$ |
| 136 | H | H | H | H | 8 | $Q_{186}$ |
| 137 | H | H | H | H | 3 | $Q_{34}$ |
| 138 | H | H | H | H | 8 | $Q_{187}$ |
| 139 | H | H | H | H | 3 | $Q_{35}$ |
| 140 | H | H | H | H | 9 | $Q_6$ |
| 141 | H | H | H | H | 3 | $Q_{40}$ |
| 142 | H | H | H | H | 9 | $Q_{89}$ |
| 143 | H | H | H | H | 3 | $Q_{46}$ |
| 144 | H | H | H | H | 9 | $Q_{91}$ |
| 145 | H | H | H | H | 3 | $Q_{59}$ |
| 146 | H | H | H | H | 9 | $Q_{117}$ |
| 147 | H | H | H | H | 3 | $Q_{60}$ |
| 148 | H | H | H | H | 9 | $Q_{168}$ |
| 149 | H | H | H | H | 3 | $Q_{61}$ |
| 150 | H | H | H | H | 9 | $Q_{169}$ |
| 151 | H | H | H | H | 3 | $Q_{62}$ |
| 152 | H | H | H | H | 9 | $Q_{170}$ |
| 153 | H | H | H | H | 3 | $Q_{89}$ |
| 154 | H | H | H | H | 9 | $Q_{184}$ |
| 155 | H | H | H | H | 3 | $Q_{90}$ |
| 156 | H | H | H | H | 9 | $Q_{185}$ |
| 157 | H | H | H | H | 3 | $Q_{91}$ |
| 158 | H | H | H | H | 9 | $Q_{186}$ |
| 159 | H | H | H | H | 3 | $Q_{90}$ |
| 160 | H | H | H | H | 9 | $Q_{187}$ |
| 161 | H | H | H | H | 3 | $Q_{92}$ |
| 162 | H | H | H | $CH_3$ | 2 | $Q_6$ |
| 163 | H | H | H | H | 3 | $Q_{114}$ |
| 164 | H | H | H | $CH_3$ | 2 | $Q_{89}$ |
| 165 | H | H | H | H | 3 | $Q_{115}$ |
| 166 | H | H | H | $CH_3$ | 2 | $Q_{91}$ |
| 167 | H | H | H | H | 3 | $Q_{116}$ |
| 168 | H | H | H | $CH_3$ | 2 | $Q_{117}$ |
| 169 | H | H | H | H | 3 | $Q_{117}$ |
| 170 | H | H | H | $CH_3$ | 2 | $Q_{168}$ |
| 171 | H | H | H | H | 3 | $Q_{124}$ |
| 172 | H | H | H | $CH_3$ | 2 | $Q_{169}$ |
| 173 | H | H | H | H | 3 | $Q_{129}$ |
| 174 | H | H | H | $CH_3$ | 2 | $Q_{170}$ |
| 175 | H | H | H | H | 3 | $Q_{130}$ |
| 176 | H | H | H | $CH_3$ | 2 | $Q_{184}$ |
| 177 | H | H | H | H | 3 | $Q_{131}$ |
| 178 | H | H | H | $CH_3$ | 2 | $Q_{185}$ |
| 179 | H | H | H | H | 3 | $Q_{145}$ |
| 180 | H | H | H | $CH_3$ | 2 | $Q_{186}$ |
| 181 | H | H | H | H | 3 | $Q_{146}$ |
| 182 | H | H | H | $CH_3$ | 2 | $Q_{187}$ |
| 183 | H | H | H | H | 3 | $Q_{147}$ |
| 184 | H | H | H | $CH_3$ | 3 | $Q_6$ |
| 185 | H | H | H | H | 3 | $Q_{148}$ |
| 186 | H | H | H | $CH_3$ | 3 | $Q_{89}$ |
| 187 | H | H | H | H | 3 | $Q_{149}$ |
| 188 | H | H | H | $CH_3$ | 3 | $Q_{91}$ |
| 189 | H | H | H | H | 3 | $Q_{150}$ |
| 190 | H | H | H | $CH_3$ | 3 | $Q_{117}$ |
| 191 | H | H | H | H | 3 | $Q_{153}$ |
| 192 | H | H | H | $CH_3$ | 3 | $Q_{168}$ |
| 193 | H | H | H | H | 3 | $Q_{158}$ |
| 194 | H | H | H | $CH_3$ | 3 | $Q_{169}$ |
| 195 | H | H | H | H | 3 | $Q_{168}$ |
| 196 | H | H | H | $CH_3$ | 3 | $Q_{170}$ |
| 197 | H | H | H | H | 3 | $Q_{169}$ |
| 198 | H | H | H | $CH_3$ | 3 | $Q_{184}$ |
| 199 | H | H | H | H | 3 | $Q_{170}$ |
| 200 | H | H | H | $CH_3$ | 3 | $Q_{185}$ |
| 201 | H | H | H | H | 3 | $Q_{171}$ |
| 202 | H | H | H | $CH_3$ | 3 | $Q_{186}$ |
| 203 | H | H | H | H | 3 | $Q_{174}$ |
| 204 | H | H | H | $CH_3$ | 3 | $Q_{187}$ |
| 205 | H | H | H | H | 2 | $Q_{166}$ |
| 206 | H | H | H | H | 3 | $Q_{166}$ |
| 207 | H | H | H | H | 2 | $Q_{173}$ |
| 208 | H | H | H | H | 3 | $Q_{173}$ |
| 209 | H | H | H | H | 2 | $Q_{177}$ |
| 210 | H | H | H | H | 3 | $Q_{177}$ |
| 211 | H | H | H | H | 2 | $Q_{178}$ |
| 212 | H | H | H | H | 3 | $Q_{178}$ |
| 213 | H | H | H | H | 2 | $Q_{179}$ |
| 214 | H | H | H | H | 3 | $Q_{179}$ |
| 215 | H | H | H | H | 2 | $Q_{180}$ |
| 216 | H | H | H | H | 3 | $Q_{180}$ |
| 217 | H | H | H | H | 2 | $Q_{181}$ |
| 218 | H | H | H | H | 3 | $Q_{181}$ |
| 219 | H | H | H | H | 2 | $Q_{182}$ |
| 220 | H | H | H | H | 3 | $Q_{182}$ |

| No. | N—X—N / $R_3$ $R_4$ | $R_{10}$ | Q |
|---|---|---|---|
| 221 | piperazine | H | $Q_6$ |
| 222 | HN-CH2-CH(Et)-NH | H | $Q_6$ |
| 223 | piperazine | H | $Q_{16}$ |
| 224 | HN-CH2-CH(Et)-NH | H | $Q_{16}$ |
| 225 | piperazine | H | $Q_{20}$ |
| 226 | HN-CH2-CH(Et)-NH | H | $Q_{20}$ |
| 227 | piperazine | H | $Q_{21}$ |
| 228 | HN-CH2-CH(Et)-NH | H | $Q_{21}$ |
| 229 | piperazine | H | $Q_{24}$ |

TABLE 2-continued

| # | Structure | | Q |
|---|---|---|---|
| 230 | HN-CH(Et)-CH2-NH (diamine) | H | $Q_{24}$ |
| 231 | piperazine | H | $Q_{25}$ |
| 232 | HN-CH(Et)-CH2-NH | H | $Q_{25}$ |
| 233 | piperazine | H | $Q_{26}$ |
| 234 | HN-CH(Et)-CH2-NH | H | $Q_{26}$ |
| 235 | piperazine | H | $Q_{30}$ |
| 236 | HN-CH(Et)-CH2-NH | H | $Q_{30}$ |
| 237 | piperazine | H | $Q_{31}$ |
| 238 | HN-CH(Et)-CH2-NH | H | $Q_{31}$ |
| 239 | piperazine | H | $Q_{32}$ |
| 240 | HN-CH(Et)-CH2-NH | H | $Q_{32}$ |
| 241 | piperazine | H | $Q_{34}$ |
| 242 | HN-CH(Et)-CH2-NH | H | $Q_{34}$ |
| 243 | piperazine | H | $Q_{35}$ |
| 244 | HN-CH(Et)-CH2-NH | H | $Q_{35}$ |
| 245 | piperazine | H | $Q_{40}$ |
| 246 | HN-CH(Et)-CH2-NH | H | $Q_{40}$ |
| 247 | piperazine | H | $Q_{46}$ |
| 248 | HN-CH(Et)-CH2-NH | H | $Q_{46}$ |
| 249 | piperazine | H | $Q_{59}$ |
| 250 | HN-CH(Et)-CH2-NH | H | $Q_{59}$ |
| 251 | piperazine | H | $Q_{60}$ |
| 252 | HN-CH(Et)-CH2-NH | H | $Q_{60}$ |
| 253 | piperazine | H | $Q_{61}$ |
| 254 | HN-CH(Et)-CH2-NH | H | $Q_{61}$ |
| 255 | piperazine | H | $Q_{62}$ |
| 256 | HN-CH(Et)-CH2-NH | H | $Q_{62}$ |
| 257 | piperazine | H | $Q_{89}$ |
| 258 | HN-CH(Et)-CH2-NH | H | $Q_{89}$ |
| 259 | piperazine | H | $Q_{90}$ |
| 260 | HN-CH(Et)-CH2-NH | H | $Q_{90}$ |
| 261 | piperazine | H | $Q_{91}$ |

TABLE 2-continued

| # | Structure | | Q |
|---|---|---|---|
| 262 | HN-CH2-CH(NH)-CH2CH3 | H | $Q_{91}$ |
| 263 | piperazine | H | $Q_{90}$ |
| 264 | HN-CH2-CH(NH)-CH2CH3 | H | $Q_{90}$ |
| 265 | piperazine | H | $Q_{92}$ |
| 266 | HN-CH2-CH(NH)-CH2CH3 | H | $Q_{92}$ |
| 267 | piperazine | H | $Q_{114}$ |
| 268 | HN-CH2-CH(NH)-CH2CH3 | H | $Q_{114}$ |
| 269 | piperazine | H | $Q_{115}$ |
| 270 | HN-CH2-CH(NH)-CH2CH3 | H | $Q_{115}$ |
| 271 | piperazine | H | $Q_{116}$ |
| 272 | HN-CH2-CH(NH)-CH2CH3 | H | $Q_{116}$ |
| 273 | piperazine | H | $Q_{117}$ |
| 274 | HN-CH2-CH(NH)-CH2CH3 | H | $Q_{117}$ |
| 275 | piperazine | H | $Q_{124}$ |
| 276 | HN-CH2-CH(NH)-CH3 | H | $Q_{124}$ |
| 277 | piperazine | H | $Q_{129}$ |
| 278 | HN-CH2-CH(NH)-CH3 | H | $Q_{129}$ |
| 279 | piperazine | H | $Q_{130}$ |
| 280 | HN-CH2-CH(NH)-CH3 | H | $Q_{130}$ |
| 281 | piperazine | H | $Q_{131}$ |
| 282 | HN-CH2-CH(NH)-CH3 | H | $Q_{131}$ |
| 283 | piperazine | H | $Q_{145}$ |
| 284 | HN-CH2-CH(NH)-CH3 | H | $Q_{145}$ |
| 285 | piperazine | H | $Q_{146}$ |
| 286 | HN-CH2-CH(NH)-CH3 | H | $Q_{146}$ |
| 287 | piperazine | H | $Q_{147}$ |
| 288 | HN-CH2-CH(NH)-CH3 | H | $Q_{147}$ |
| 289 | piperazine | H | $Q_{148}$ |
| 290 | HN-CH2-CH(NH)-CH3 | H | $Q_{148}$ |
| 291 | piperazine | H | $Q_{149}$ |
| 292 | HN-CH2-CH(NH)-CH3 | H | $Q_{149}$ |
| 293 | piperazine | H | $Q_{150}$ |

TABLE 2-continued

| # | Structure | | |
|---|---|---|---|
| 294 | HN-CH2-CH(CH3)-NH | H | $Q_{150}$ |
| 295 | piperazine | H | $Q_{153}$ |
| 296 | HN-CH2-CH(CH3)-NH | H | $Q_{153}$ |
| 297 | piperazine | H | $Q_{158}$ |
| 298 | HN-CH2-CH(CH3)-NH | H | $Q_{158}$ |
| 299 | piperazine | H | $Q_{168}$ |
| 300 | HN-CH2-CH(CH3)-NH | H | $Q_{168}$ |
| 301 | piperazine | H | $Q_{169}$ |
| 302 | HN-CH2-CH(CH3)-NH | H | $Q_{169}$ |
| 303 | piperazine | H | $Q_{170}$ |
| 304 | HN-CH2-CH(CH3)-NH | H | $Q_{170}$ |
| 305 | piperazine | H | $Q_{171}$ |
| 306 | HN-CH2-CH(CH3)-NH | H | $Q_{171}$ |
| 307 | piperazine | H | $Q_{174}$ |
| 308 | HN-CH2-CH(CH3)-NH | H | $Q_{174}$ |
| 309 | piperazine | H | $Q_{175}$ |

TABLE 2-continued

| # | Structure | | |
|---|---|---|---|
| 310 | HN-CH2-CH(CH3)-NH | H | $Q_{175}$ |
| 311 | piperazine | H | $Q_{176}$ |
| 312 | HN-CH2-CH(CH3)-NH | H | $Q_{176}$ |
| 313 | piperazine | H | $Q_{184}$ |
| 314 | HN-CH2-CH(CH3)-NH | H | $Q_{184}$ |
| 315 | piperazine | H | $Q_{185}$ |
| 316 | HN-CH2-CH(CH3)-NH | H | $Q_{185}$ |
| 317 | piperazine | H | $Q_{186}$ |
| 318 | HN-CH2-CH(CH3)-NH | H | $Q_{186}$ |
| 319 | piperazine | H | $Q_{187}$ |
| 320 | HN-CH2-CH(CH3)-NH | H | $Q_{187}$ |
| 321 | piperazine | H | $Q_{196}$ |
| 322 | HN-CH2-CH(CH3)-NH | H | $Q_{196}$ |
| 323 | piperazine | H | $Q_{197}$ |
| 324 | HN-CH2-CH(CH3)-NH | H | $Q_{197}$ |
| 325 | piperazine | H | $Q_{198}$ |

TABLE 2-continued

| | | | |
|---|---|---|---|
| 326 | 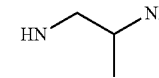 | H | $Q_{198}$ |
| 327 | 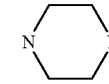 | H | $Q_{199}$ |
| 328 | 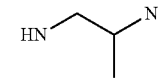 | H | $Q_{199}$ |
| 329 | 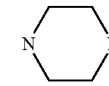 | H | $Q_{200}$ |
| 330 | 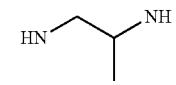 | H | $Q_{200}$ |
| 331 | 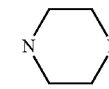 | H | $Q_{201}$ |
| 332 | 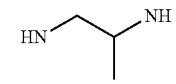 | H | $Q_{201}$ |
| 333 | 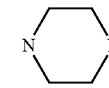 | H | $Q_{206}$ |
| 334 | 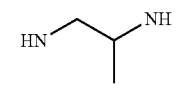 | H | $Q_{206}$ |
| 335 | 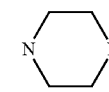 | H | $Q_{207}$ |
| 336 | 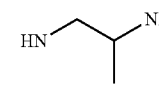 | H | $Q_{207}$ |

Table 3: Wherein for formula I-1, $NR_{10}$—CO-Q is at the 4-position of benzene ring, $G_1$ is $CR_6$, $G_2$ is $CR_7$, $G_3$ is $CR_8$, X=$(CHR_5)_n$, $R_1$, $R_2$, $R_6$ and $R_7$ are H, $R_8$ is Cl; $R_3$, $R_4$, $R_5$, $R_{10}$, n and Q in Table 3 are the same as that of Table 2.

Table 4: Wherein for formula I-1, $NR_{10}$—CO-Q is at the 2-position of benzene ring, $G_1$ is $CR_6$, $G_2$ is $CR_7$, $G_3$ is $CR_8$, X=$(CHR_5)_n$, $R_1$, $R_2$, $R_6$ and $R_7$ are I-1, $R_8$ is CN; $R_3$, $R_4$, $R_5$, $R_{10}$, n and Q in Table 4 are the same as that of Table 2.

Table 5: Wherein for formula I-1, $NR_{10}$—CO-Q is at the 4-position of benzene ring, $G_1$ is $CR_6$, $G_2$ is $CR_7$, $G_3$ is $CR_8$, X=$(CHR_5)_n$, $R_1$, $R_2$, $R_6$ and $R_7$ are H, $R_8$ is CN; $R_3$, $R_4$, $R_5$, $R_{10}$, n and Q in Table 5 are the same as that of Table 2.

Table 6: Wherein for formula I-1, $NR_{10}$—CO-Q is at the 2-position of benzene ring, $G_1$ is $CR_6$, $G_2$ is $CR_7$, $G_3$ is $CR_8$, X=$(CHR_5)_n$, $R_2$, $R_6$ and $R_7$ are H, $R_1$ is Cl, $R_8$ is $CF_3$; $R_3$, $R_4$, $R_5$, $R_{10}$, n and Q in Table 6 are the same as that of Table 2.

Table 7: Wherein for formula I-1, $NR_{10}$—CO-Q is at the 4-position of benzene ring, $G_1$ is $CR_6$, $G_2$ is $CR_7$, $G_3$ is $CR_8$, X=$(CHR_5)_n$, $R_2$, $R_6$ and $R_7$ are I-1, $R_1$ is Cl, $R_8$ is $CF_3$; $R_3$, $R_4$, $R_5$, $R_{10}$, n and Q in Table 3 are the same as that of Table 2.

Table 8: Wherein for formula I-1, $NR_{10}$—CO-Q is at the 2-position of benzene ring, $G_1$ is $CR_6$, $G_2$ is $CR_7$, $G_3$ is $CR_8$, X=$(CHR_5)_n$, $R_2$, $R_6$ and $R_7$ are H, $R_1$ is $NO_2$, $R_8$ is $CF_3$; $R_3$, $R_4$; $R_5$, $R_{10}$, n and Q in Table 8 are the same as that of Table 2.

Table 9: Wherein for formula I-1, $NR_{10}$—CO-Q is at the 4-position of benzene ring, $G_1$ is $CR_6$, $G_2$ is $CR_7$, $G_3$ is $CR_8$, X=$(CHR_5)_n$, $R_2$, $R_6$ and $R_7$ are H, $R_1$ is $NO_2$, $R_8$ is $CF_3$; $R_3$, $R_4$, $R_5$, $R_{10}$, n and Q in Table 9 are the same as that of Table 2.

Table 10: Wherein for formula I-1, $NR_{10}$—CO-Q is at the 2-position of benzene ring, $G_1$ is $CR_6$, $G_2$ is $CR_7$, $G_3$ is $CR_8$, X=$(CHR_5)_n$, $R_2$ and $R_7$ are H, $R_1$ and $R_6$ are Cl, $R_8$ is $CF_3$; $R_3$, $R_4$, $R_5$, $R_{10}$, n and Q in Table 3 are the same as that of Table 2.

Table 11: Wherein for formula I-1, $NR_{10}$—CO-Q is at the 4-position of benzene ring, $G_1$ is $CR_6$, $G_2$ is $CR_7$, $G_3$ is $CR_8$, X=$(CHR_5)_n$, $R_2$ and $R_7$ are H, $R_1$ and $R_6$ are Cl, $R_8$ is $CF_3$; $R_3$, $R_4$, $R_5$, $R_{10}$, n and Q in Table 11 are the same as that of Table 2.

Table 12: Wherein for formula I-1, $NR_{10}$—CO-Q is at the 2-position of benzene ring, $G_1$ is $CR_6$, $G_2$ is $CR_7$, $G_3$ is $CR_8$, X=$(CHR_5)_n$, $R_2$ and $R_7$ are H, $R_1$ and $R_6$ are $NO_2$, $R_8$ is $CF_3$; $R_3$, $R_4$, $R_5$, $R_{10}$, n and Q in Table 12 are the same as that of Table 2.

Table 13: Wherein for formula I-1, $NR_{10}$—CO-Q is at the 4-position of benzene ring, $G_1$ is $CR_6$, $G_2$ is $CR_7$, $G_3$ is $CR_8$, X=$(CHR_5)_n$, $R_2$ and $R_7$ are H, $R_1$ and $R_6$ are $NO_2$, $R_8$ is $CF_3$; $R_3$, $R_4$, $R_5$, $R_{10}$, n and Q in Table 13 are the same as that of Table 2.

Table 14: Wherein for formula I-1, $NR_{10}$—CO-Q is at the 2-position of benzene ring, $G_1$ is $CR_6$, $G_2$ is $CR_7$, $G_3$ is $CR_8$, X=$(CHR_5)_n$, $R_2$ and $R_7$ are H, $R_1$ and $R_6$ are Cl, $R_8$ is CN; $R_3$, $R_4$, $R_5$, $R_{10}$, n and Q in Table 14 are the same as that of Table 2.

Table 15: Wherein for formula I-1, $NR_{10}$—CO-Q is at the 4-position of benzene ring, $G_1$ is $CR_6$, $G_2$ is $CR_7$, $G_3$ is $CR_8$, X=$(CHR_5)_n$, $R_2$ and $R_7$ are H, $R_1$ and $R_6$ are Cl, $R_8$ is CN; $R_3$, $R_4$, $R_5$, $R_{10}$, n and Q in Table 15 are the same as that of Table 2.

Table 16: Wherein for formula I-1, $NR_{10}$—CO-Q is at the 2-position of benzene ring, $G_1$ is $CR_6$, $G_2$ is $CR_7$, $G_3$ is $CR_8$, X=$(CHR_5)_n$, $R_1$ and $R_6$ are $NO_2$, $R_2$ is $C_1$, $R_7$ is H, $R_8$ is $CF_3$; $R_3$, $R_4$, $R_5$, $R_{10}$, n and Q in Table 16 are the same as that of Table 2.

Table 17: Wherein for formula I-1, $NR_{10}$—CO-Q is at the 4-position of benzene ring, $G_1$ is $CR_6$, $G_2$ is $CR_7$, $G_3$ is $CR_8$, X=$(CHR_5)_n$, $R_1$ and $R_6$ are $NO_2$, $R_2$ is $C_1$, $R_7$ is H, $R_8$ is $CF_3$; $R_3$, $R_4$, $R_5$, $R_{10}$, n and Q in Table 17 are the same as that of Table 2.

Table 18: Wherein for formula I-1, $NR_{10}$—CO-Q is at the 2-position of benzene ring, $G_1$ is N, $G_2$ $G_2$ is $CR_7$, $G_3$ is $CR_8$, X=$(CHR_5)_n$, $R_1$ is $C_1$, $R_2$, $R_7$ and $R_8$ are H; $R_3$, $R_4$, $R_5$, $R_{10}$, n and Q in Table 18 are the same as that of Table 2.

Table 19: Wherein for formula I-1, $NR_{10}$—CO-Q is at the 4-position of benzene ring, $G_1$ is N, $G_2$ is $CR_7$, $G_3$ is $CR_8$, X=$(CHR_5)_n$, $R_1$ is $C_1$, $R_2$, $R_7$ and $R_8$ are H; $R_3$, $R_4$, $R_5$, $R_{10}$, n and Q in Table 19 are the same as that of Table 2.

Table 20: Wherein for formula I-1, $NR_{10}$—CO-Q is at the 2-position of benzene ring, $G_1$ is N, $G_2$ is $CR_7$, $G_3$ is $CR_8$, X=$(CHR_5)_n$, $R_8$ is $CF_3$, $R_4$, $R_2$ and $R_7$ are H; $R_3$, $R_4$, $R_5$, $R_{10}$, n and Q in Table 20 are the same as that of Table 2.

Table 21: Wherein for formula I-1, $NR_{10}$—CO-Q is at the 4-position of benzene ring, $G_1$ is N, $G_2$ is $CR_7$, $G_3$ is $CR_8$, X=$(CHR_5)_n$, $R_8$ is $CF_3$, $R_4$, $R_2$ and $R_7$ are H; $R_3$, $R_4$, $R_5$, $R_{10}$, n and Q in Table 21 are the same as that of Table 2.

Table 22: Wherein for formula I-1, $NR_{10}$—CO-Q is at the 2-position of benzene ring, $G_1$ is N, $G_2$ is $CR_7$, $G_3$ is $CR_8$, X=(CHR$_5$)$_n$, R$_1$ is Cl, R$_8$ is CF$_3$, R$_2$ and R$_7$ are H; R$_3$, R$_4$, R$_5$, R$_{10}$, n and Q in Table 22 are the same as that of Table 2.

Table 23: Wherein for formula I-1, NR$_{10}$—CO-Q is at the 4-position of benzene ring, G$_1$ is N, G$_2$ is CR$_7$, G$_3$ is CR$_8$, X=(CHR$_5$)$_n$, R$_1$ is Cl, R$_8$ is CF$_3$, R$_2$ and R$_7$ are H; R$_3$, R$_4$, R$_5$, R$_{10}$, n and Q in Table 23 are the same as that of Table 2.

Table 24: Wherein for formula I-1, NR$_{10}$—CO-Q is at the 2-position of benzene ring, G$_1$ is N, G$_2$ is CR$_7$, G$_3$ is CR$_8$, X=(CHR$_5$)$_n$, R$_1$ is Cl, R$_8$ is CN, R$_2$ and R$_7$ are H; R$_3$, R$_4$, R$_5$, R$_{10}$, n and Q in Table 24 are the same as that of Table 2.

Table 25: Wherein for formula I-1, NR$_{10}$—CO-Q is at the 4-position of benzene ring, G$_1$ is N, G$_2$ is CR$_7$, G$_3$ is CR$_8$, X=(CHR$_5$)$_{11}$, R$_1$ is Cl, R$_8$ is CN, R$_2$ and R$_7$ are H; R$_3$, R$_4$, R$_5$, R$_{10}$, n and Q in Table 25 are the same as that of Table 2.

Table 26: Wherein for formula I-1, NR$_{10}$—CO-Q is at the 2-position of benzene ring, G$_1$ is N, G$_2$ is CR$_7$, G$_3$ is CR$_8$, X=(CHR$_5$)$_n$, R$_1$ is H, R$_2$ is CF$_3$, R$_7$ is Cl, R$_8$ is CN; R$_3$, R$_4$, R$_5$, R$_{10}$, n and Q in Table 26 are the same as that of Table 2.

Table 27: Wherein for formula I-1, NR$_{10}$—CO-Q is at the 4-position of benzene ring, G$_1$ is N, C) is CR$_7$, G$_3$ is CR$_8$, X=(CHR$_5$)$_n$, R$_1$ is H, R$_2$ is CF$_3$, R$_7$ is Cl, R$_8$ is CN; R$_3$, R$_4$, R$_5$, R$_{10}$, n and Q in Table 27 are the same as that of Table 2.

Table 28: Wherein for formula I-1, NR$_{10}$—CO-Q is at the 2-position of benzene ring, G$_1$ is N, G$_2$ is CR$_7$, G$_3$ is CR$_8$, X=(CHR$_5$)$_n$, R$_1$ is H, R$_2$ is CH$_3$, R$_7$ is Cl, R$_8$ is CN; R$_3$, R$_4$, R$_5$, R$_{10}$, n and Q in Table 28 are the same as that of Table 2.

Table 29: Wherein for formula I-1, NR$_{10}$—CO-Q is at the 4-position of benzene ring, G$_1$ is N, G$_2$ is CR$_7$, G$_3$ is CR$_8$, X=(CHR$_5$)$_n$, R$_1$ is H, R$_2$ is CH$_3$, R$_7$ is Cl, R$_8$ is CN; R$_3$, R$_4$, R$_5$, R$_{10}$, n and Q in Table 29 are the same as that of Table 2.

Table 30: Wherein for formula I-1, NR$_{10}$—CO-Q is at the 2-position of benzene ring, G$_1$ is N, G$_2$ is CR$_7$, G$_3$ is CR$_8$, X=(CHR$_5$)$_n$, R$_1$ is CN, R$_2$ is CH$_3$, R$_7$ is CH$_3$, R$_8$ is H; R$_3$, R$_4$, R$_5$, R$_{10}$, n and Q in Table 30 are the same as that of Table 2.

Table 31: Wherein for formula I-1, NR$_{10}$—CO-Q is at the 4-position of benzene ring, G$_1$ is N, G$_2$ is CR$_7$, G$_3$ is CR$_8$, X=(CHR$_5$)$_n$, R$_1$ is CN, R$_2$ is CH$_3$, R$_7$ is CH$_3$, R$_8$ is H; R$_3$, R$_4$, R$_5$, R$_{10}$, n and Q in Table 31 are the same as that of Table 2.

Table 32: Wherein for formula I-1, NR$_{10}$—CO-Q is at the 2-position of benzene ring, G$_1$ is N, G$_2$ is CR$_7$, G$_3$ is CR$_8$, X=(CHR$_5$)$_n$, R$_1$ is C$_1$, R$_2$ is CH$_3$, R$_7$ is CH$_3$, R$_8$ is H; R$_3$, R$_4$, R$_5$, R$_{10}$, n and Q in Table 32 are the same as that of Table 2.

Table 33: Wherein for formula I-1, NR$_{10}$—CO-Q is at the 4-position of benzene ring, G$_1$ is N, G$_2$ is CR$_7$, G$_3$ is CR$_8$, X=(CHR$_5$)$_n$, R$_1$ is C$_1$, R$_2$ is H, R$_7$ and R$_8$ are Cl; R$_3$, R$_4$, R$_5$, R$_{10}$, n and Q in Table 33 are the same as that of Table 2.

Table 34: Wherein for formula I-1, NR$_{10}$—CO-Q is at the 2-position of benzene ring, G$_1$ and G$_3$ are N, G$_2$ is CR$_7$, X=(CHR$_5$)$_n$, R$_1$ is Cl, R$_1$ is CH$_3$, R$_7$ is H; R$_3$, R$_4$, R$_5$, R$_{10}$, n and Q in Table 34 are the same as that of Table 2.

Table 35: Wherein for formula I-1, NR$_{10}$—CO-Q is at the 4-position of benzene ring, G$_1$ and G$_3$ are N, G$_2$ is CR$_7$, X=(CHR$_5$)$_n$, R$_1$ is C$_1$, R$_2$ is CH$_3$, R$_7$ is H; R$_3$, R$_4$, R$_5$, R$_{10}$, n and Q in Table 35 are the same as that of Table 2.

Table 36: Wherein for formula I-1, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CF$_3$, R$_7$ is CH(CH$_3$)$_2$O; R$_3$, R$_4$, R$_5$, R$_{10}$, n and Q in Table 36 are the same as that of Table 2.

Table 37: Wherein for formula I-1, NR$_{10}$—CO-Q is at the 4-position of benzene ring, G$_1$ and G$_3$ are N, G$_2$ is CR$_7$, X=(CHR$_5$)$_n$, R$_1$ is H, R$_2$ is CF$_3$, R$_7$ is CH(CH$_3$)$_2$O; R$_3$, R$_4$, R$_5$, R$_{10}$, n and Q in Table 37 are the same as that of Table 2.

Table 38: Wherein for formula I-1, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CF$_3$, R$_7$ is cyclopropyl; R$_3$, R$_4$, R$_5$, R$_{10}$, n and Q in Table 38 are the same as that of Table 2.

Table 39: Wherein for formula I-1, NR$_{10}$—CO-Q is at the 4-position of benzene ring, G$_1$ and G$_3$ are N, G$_2$ is CR$_7$, X=(CHR$_5$)$_n$, R$_1$ is H, R$_2$ is CF$_3$, R$_7$ is cyclopropyl; R$_3$, R$_4$, R$_5$, R$_{10}$, n and Q in Table 39 are the same as that of Table 2.

Table 40: Wherein for formula I-1, NR$_{10}$—CO-Q is at the 2-position of benzene ring, G$_1$ and G$_3$ are N, G$_2$ is CR$_7$, X=(CHR$_5$)$_n$, R$_1$ is CH$_3$, R$_2$ is Ph, R$_7$ is CH$_3$; R$_3$, R$_4$, R$_5$, R$_{10}$, n and Q in Table 40 are the same as that of Table 2.

Table 41: Wherein for formula I-1, NR$_{10}$—CO-Q is at the 4-position of benzene ring, G$_1$ and G$_3$ are N, G$_2$ is CR$_7$, X=(CHR$_5$)$_n$, R$_1$ is CH$_3$, R$_2$ is Ph, R$_7$ is CH$_3$; R$_3$, R$_4$, R$_5$, R$_{10}$, n and Q in Table 41 are the same as that of Table 2.

Table 42: Wherein for formula I-1, NR$_{10}$—CO-Q is at the 2-position of benzene ring, G$_1$ and G$_3$ are N, G$_2$ is CR$_7$, X=(CHR$_5$)$_n$, R$_1$ is CH$_3$ R$_2$ is 4-Cl-Ph, R$_7$ is CH$_3$; R$_3$, R$_4$, R$_5$, R$_{10}$, n and Q in Table 42 are the same as that of Table 2.

Table 43: Wherein for formula I-1, NR$_{10}$—CO-Q is at the 4-position of benzene ring, G$_1$ and G$_3$ are N, G$_2$ is CR$_7$, X=(CHR$_5$)$_n$, R$_1$ is CH$_3$, R$_2$ is 4-Cl-Ph, R$_7$ is CH$_3$; R$_3$, R$_4$, R$_5$, R$_{10}$, n and Q in Table 43 are the same as that of Table 2.

Table 44: Wherein for formula I-1, NR$_{10}$—CO-Q is at the 2-position of benzene ring, G$_1$ and G$_3$ are N, G$_2$ is CR$_7$, X=(CHR$_5$)$_n$, R$_1$ is CH$_3$, G$_2$ is 4-CH$_3$O-Ph, R$_7$ is CH$_3$; R$_3$, R$_4$, R$_5$, R$_{10}$, n and Q in Table 44 are the same as that of Table 2.

Table 45: Wherein for formula I-1, NR$_{10}$—CO-Q is at the 4-position of benzene ring, G$_1$ and G$_3$ are N, G$_2$ is CR$_7$, X=(CHR$_5$)$_n$, R$_1$ is CH$_3$, R$_2$ is 4-CH$_3$O-Ph, R$_7$ is CH$_3$; R$_3$, R$_4$, R$_5$, R$_{10}$, n and Q in Table 45 are the same as that of Table 2.

Table 46: Wherein for formula I-1, NR$_{10}$—CO-Q is at the 2-position of benzene ring, G$_1$ and G$_3$ are N, G$_2$ is CR$_7$, X=(CHR$_5$)$_n$, R$_1$ and R$_7$ are H, R$_2$ is Cl; R$_3$, R$_4$, R$_5$, R$_{10}$, n and Q in Table 46 are the same as that of Table 2.

Table 47: Wherein for formula I-1, NR$_{10}$—CO-Q is at the 4-position of benzene ring, G$_1$ and G$_3$ are N, G$_2$ is CR$_7$, X=(CHR$_5$)$_n$, R$_1$ and R$_7$ are H, R$_2$ is Cl; R$_3$, R$_4$, R$_5$, R$_{10}$, n and Q in Table 47 are the same as that of Table 2.

Table 48: Wherein for formula I-1, NR$_{10}$—CO-Q is at the 2-position of benzene ring, G$_1$ and G$_3$ are N, G$_2$ is CR$_7$, X=(CHR$_5$)$_n$, R$_1$ is F, R$_2$ is C$_1$, R$_7$ is H; R$_3$, R$_4$, R$_5$, R$_{10}$, n and Q in Table 48 are the same as that of Table 2.

Table 49: Wherein for formula I-1, NR$_{10}$—CO-Q is at the 4-position of benzene ring, G$_1$ and G$_3$ are N, G$_2$ is CR$_7$, X=(CHR$_5$)$_n$, R$_1$ is F, R$_2$ is C$_1$, R$_7$ is H; R$_3$, R$_4$, R$_5$, R$_{10}$, n and Q in Table 49 are the same as that of Table 2.

Table 50: Wherein for formula I-1, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CH$_3$, R$_7$ is CH$_3$O; R$_3$, R$_4$, R$_5$, R$_{10}$, n and Q in Table 50 are the same as that of Table 2.

Table 51: Wherein for formula I-1, NR$_{10}$—CO-Q is at the 4-position of benzene ring, G$_1$ and G$_3$ are N, G$_2$ is CR$_7$, X=(CHR$_5$)$_n$, R$_1$ is H, R$_2$ is CH$_3$, R$_7$ is CH$_3$O; R$_3$, R$_4$, R$_5$, R$_{10}$, n and Q in Table 51 are the same as that of Table 2.

Table 52: Wherein for formula I-1, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CH$_3$, R$_7$ is (C$_2$H$_5$)$_2$N; R$_3$, R$_4$, R$_5$, R$_{10}$, n and Q in Table 52 are the same as that of Table 2.

Table 53: Wherein for formula I-1, NR$_{10}$—CO-Q is at the 4-position of benzene ring, G$_1$ and G$_3$ are N, G$_2$ is CR$_7$, X=(CHR$_5$)$_n$, R$_1$ is H, R$_2$ is CH$_3$, R$_7$ is (C$_2$H$_5$)$_2$N; R$_3$, R$_4$, R$_5$, R$_{10}$, n and Q in Table 53 are the same as that of Table 2.

Table 54: Wherein for formula I-1, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CF$_3$, R$_7$ is CH$_3$O; R$_3$, R$_4$, R$_5$, R$_{10}$, n and Q in Table 54 are the same as that of Table 2.

Table 55: Wherein for formula I-1, NR$_{10}$—CO-Q is at the 4-position of benzene ring, G$_1$ and G$_3$ are N, G$_2$ is CR$_7$, Table 56: Wherein for formula I-1, $NR_{10}$—CO-Q is at the 2-position of benzene ring, $G_1$ and $G_3$ are N, $G_2$ is $CR_7$, $X=(CHR_5)_n$, $R_1$ is H, $R_2$ is $CF_3$, $R_7$ is $(C_2H_5)_2N$; $R_3$, $R_4$, $R_5$, $R_{10}$, n and Q in Table 56 are the same as that of Table 2.

Table 57: Wherein for formula I-1, $NR_{10}$—CO-Q is at the 4-position of benzene ring, $G_1$ and $G_3$ are N, $G_2$ is $CR_7$, $X=(CHR_5)_n$, $R_1$ is H, $R_2$ is $CF_3$, $R_7$ is $(C_2H_5)_2N$; $R_3$, $R_4$, $R_5$, $R_{10}$, n and Q in Table 57 are the same as that of Table 2.

Table 58: Wherein for formula I-1, $NR_{10}$—CO-Q is at the 2-position of benzene ring, $G_1$ and $G_3$ are N, $G_2$ is $CR_7$, $X=(CHR_5)_n$, $R_1$ is H, $R_2$ is $CH_3$, $R_7$ is $CH_3CH_2CH_2$; $R_3$, $R_4$, $R_5$, $R_{10}$, n and Q in Table 58 are the same as that of Table 2.

Table 59: Wherein for formula I-1, $NR_{10}$—CO-Q is at the 4-position of benzene ring, $G_1$ and $G_3$ are N, $G_2$ is $CR_7$, $X=(CHR_5)_n$, $R_1$ is H, $R_2$ is $CH_3$, $R_7$ is $CH_3CH_2CH_2$; $R_3$, $R_4$, $R_5$, $R_{10}$, n and Q in Table 59 are the same as that of Table 2.

Table 60: Wherein for formula I-1, $NR_{10}$—CO-Q is at the 2-position of benzene ring, $G_1$ and $G_3$ are N, $G_2$ is $CR_7$, $X=(CHR_5)_n$, $R_1$ is $C_4H_9$, $R_2$ is $CH_3$, $R_7$ is $(C_2H_5)_2N$; $R_3$, $R_4$, $R_5$, $R_{10}$, n and Q in Table 60 are the same as that of Table 2.

Table 61: Wherein for formula I-1, $NR_{10}$—CO-Q is at the 4-position of benzene ring, $G_1$ and $G_3$ are N, $G_2$ is $CR_7$, $X=(CHR_5)_n$, $R_1$ is $C_4H_9$, $R_2$ is $CH_3$, $R_7$ is $(C_2H_5)_2N$; $R_3$, $R_4$, $R_5$, $R_{10}$, n and Q in Table 61 are the same as that of Table 2.

Table 62: Wherein for formula I-1, $NR_{10}$—CO-Q is at the 2-position of benzene ring, $G_1$ and $G_3$ are N, $G_2$ is $CR_7$, $X=(CHR_5)_n$, $R_1$ is $C_4H_9$, $R_2$ is $CH_3$, $R_7$ is $C_2H_5NH$; $R_3$, $R_4$, $R_5$, $R_{10}$, n and Q in Table 62 are the same as that of Table 2.

Table 63: Wherein for formula I-1, $NR_{10}$—CO-Q is at the 4-position of benzene ring, $G_1$ and $G_3$ are N, $G_2$ is $CR_7$, $X=(CHR_5)_n$, $R_1$ is $C_4H_9$, $R_2$ is $CH_3$, $R_7$ is $C_2H_5NH$; $R_3$, $R_4$, $R_5$, $R_{10}$, n and Q in Table 63 are the same as that of Table 2.

Table 64: Wherein for formula I-1, $NR_{10}$—CO-Q is at the 2-position of benzene ring, $G_1$ and $G_3$ are N, $G_2$ is $CR_7$, $X=(CHR_5)_n$, $R_1$ is H, $R_2$ is $CH_3$, $R_7$ is Ph-NH; $R_3$, $R_4$, $R_5$, $R_{10}$, n and Q in Table 64 are the same as that of Table 2.

Table 65: Wherein for formula I-1, $NR_{10}$—CO-Q is at the 4-position of benzene ring, $G_1$ and $G_3$ are N, $G_2$ is $CR_7$, $X=(CHR_5)_n$, $R_1$ is H, $R_2$ is $CH_3$, $R_7$ is Ph-NH; $R_3$, $R_4$, $R_5$, $R_{10}$, n and Q in Table 65 are the same as that of Table 2.

Table 66: Wherein for formula I-1, $NR_{10}$—CO-Q is at the 2-position of benzene ring, $G_1$ and $G_3$ are N, $G_2$ is $CR_7$, $X=(CHR_5)_n$, $R_1$ is H, $R_2$ is $CF_3$, $R_7$ is 4-Cl-Ph-NH; $R_3$, $R_4$, $R_5$, $R_{10}$, n and Q in Table 66 are the same as that of Table 2.

Table 67: Wherein for formula I-1, $NR_{10}$—CO-Q is at the 4-position of benzene ring. $G_1$ and $G_3$ are N, $G_2$ is $CR_7$, $X=(CHR_5)_n$, $R_1$ is H, $R_2$ is $CF_3$, $R_7$ is 4-Cl-Ph-NH; $R_3$, $R_4$, $R_5$, $R_{10}$, n and Q in Table 67 are the same as that of Table 2.

Table 68: Wherein for formula I-1, $NR_{10}$—CO-Q is at the 2-position of benzene ring, $G_1$ and $G_3$ are N, $G_2$ is $CR_7$, $X=(CHR_5)_n$, $R_1$ is H, $R_2$ is $CF_3$, $R_7$ is Ph-NH; $R_3$, $R_4$, $R_5$, $R_{10}$, n and Q in Table 68 are the same as that of Table 2.

Table 69: Wherein for formula I-1, $NR_{10}$—CO-Q is at the 4-position of benzene ring, $G_1$ and $G_3$ are N, $G_2$ is $CR_7$, $X=(CHR_5)_n$, $R_1$ is H, $R_2$ is $CF_3$, $R_7$ is Ph-NH; $R_3$, $R_4$, $R_5$, $R_{10}$, n and Q in Table 69 are the same as that of Table 2.

Table 70: Wherein for formula I-1, $NR_{10}$—CO-Q is at the 2-position of benzene ring, $G_1$ and $G_3$ are N, $Cl_2$ is $CR_7$, $X=(CHR_5)_n$, $R_1$ is H, $R_7$ is $CH_3$, $R_7$ is 4-Cl-Ph-NH; $R_3$, $R_4$, $R_5$, $R_{10}$, n and Q in Table 70 are the same as that of Table 2.

Table 71: Wherein for formula I-1, $NR_{10}$—CO-Q is at the 4-position of benzene ring, $G_1$ and $G_3$ are N, $G_2$ is $CR_7$, $X=(CHR_5)_n$, $R_1$ is $CH_3$, $R_7$ is 4-Cl-Ph-NH; $R_3$, $R_4$, $R_5$, $R_{10}$, n and Q in Table 71 are the same as that of Table 2.

Table 72: Wherein for formula I-1, $NR_{10}$—CO-Q is at the 2-position of benzene ring, $G_1$ and $G_2$ are N, $G_3$ is $CR_8$, $X=(CHR_5)_n$, $R_1$ and $R_2$ are $F_1$, $R_8$ is Cl; $R_3$, $R_4$, $R_5$, $R_{10}$, n and Q in Table 72 are the same as that of Table 2.

Table 73: Wherein for formula I-1, $NR_{10}$—CO-Q is at the 4-position of benzene ring, $G_1$ and $G_2$ are N, $G_3$ is $CR_8$, $X=(CHR_5)_n$, $R_1$ and $R_2$ are H, $R_8$ is Cl; $R_3$, $R_4$, $R_5$, $R_{10}$, n and Q in Table 73 are the same as that of Table 2.

Table 74: Wherein for formula I-1, $NR_{10}$—CO-Q is at the 2-position of benzene ring, $G_1$ and $G_2$ are N, $G_3$ is $CR_8$, $X=(CHR_5)_n$, $R_1$, $R_2$ and $R_8$ are N; $R_3$, $R_4$, $R_5$, $R_{10}$, n and Q in Table 74 are the same as that of Table 2.

Table 75: Wherein for formula I-1, $NR_{10}$—CO-Q is at the 4-position of benzene ring, $G_1$ and $07$ are N, $G_3$ is $CR_8$, $X=(CHR_5)_n$, $R_1$, $R_2$ and $R_8$ are H; $R_3$, $R_4$, $R_5$, $R_{10}$, n and Q in Table 75 are the same as that of Table 2.

Table 76: Wherein for formula I-1, $NR_{10}$—CO-Q is at the 2-position of benzene ring, $G_1$ and $G_2$ are N, $G_3$ is $CR_8$, $X=(CHR_5)_n$, $R_1$ and $R_2$ are H, $R_8$ is Ph; $R_3$, $R_4$, $R_5$, $R_{10}$, n and Q in Table 76 are the same as that of Table 2.

Table 77: Wherein for formula I-1, $NR_{10}$—CO-Q is at the 4-position of benzene ring, $G_1$ and $G_2$ are N, $G_3$ is $CR_8$, $X=(CHR_5)_n$, $R_1$ and $R_2$ are H, $R_8$ is Ph; $R_3$, $R_4$, $R_5$, $R_{10}$, n and Q in Table 77 are the same as that of Table 2.

Table 78: Wherein for formula I-1, $NR_{10}$—CO-Q is at the 2-position of benzene ring, $G_1$ is $CR_6$, $G_2$ is $CR_7$, $G_3$ is $CR_8$, $X=(CHR_5)_n$, $R_1$, $R_6$, $R_7$ and $R_8$ are H, $R_2$ is $C(CH_3)_3$; $R_3$, $R_4$, $R_5$, $R_{10}$, n and Q in Table 78 are the same as that of Table 2.

Table 79: Wherein for formula I-1, $NR_{10}$—CO-Q is at the 4-position of benzene ring, $G_1$ is $CR_6$, $G_2$ is $CR_7$, $G_3$ is $CR_8$, $X=(CHR_5)_n$, $R_1$, $R_6$, $R_7$ and $R_8$ are H, $R_2$ is $C(CH_3)_3$; $R_3$, $R_4$, $R_5$, $R_{10}$, n and Q in Table 79 are the same as that of Table 2.

Table 80: Wherein for formula I-1, $NR_{10}$—CO-Q is at the 2-position of benzene ring, $G_1$ is N, $G_2$ is $CR_7$, $G_3$ is $CR_8$, $X=(CHR_5)_n$, $R_1$ and $R_7$ are $C_1$, $R_2$ is H, $R_8$ is $CF_3$; $R_3$, $R_4$, $R_5$, $R_{10}$, n and Q in Table 80 are the same as that of Table 2.

Table 81: Wherein for formula I-1, $NR_{10}$—CO-Q is at the 4-position of benzene ring, $G_1$ is N, $G_2$ is $CR_7$, $G_3$ is $CR_8$, $X=(CHR_5)_n$, $R_1$ and $R_7$ are $C_1$, $R_2$ is H, $R_8$ is $CF_3$; $R_3$, $R_4$, $R_5$, $R_{10}$, n and Q in Table 81 are the same as that of Table 2.

Table 82: Wherein for formula I-1, $NR_{10}$—CO-Q is at the 2-position of benzene ring, $G_1$ is N, $G_2$ is $CR_7$, $G_3$ is $CR_8$, $X=(CHR_5)_n$, $R_2$ and $R_7$ are H, $R_1$ and $R_8$ are Cl; $R_3$, $R_4$, $R_5$, $R_{10}$, n and Q in Table 82 are the same as that of Table 2.

Table 83: Wherein for formula I-1, $NR_{10}$—CO-Q is at the 4-position of benzene ring, $G_1$ is N, $G_2$ is $CR_7$, $G_3$ is $CR_8$, $X=(CHR_5)_n$, $R_2$ and $R_7$ are H, $R_1$ and $R_8$ are Cl; $R_3$, $R_4$, $R_5$, $R_{10}$, n and Q in Table 83 are the same as that of Table 2.

Table 84: Wherein for formula I-1, $NR_{10}$—CO-Q is at the 2-position of benzene ring, $G_1$ is N, $G_2$ is $CR_7$, $G_3$ is $CR_8$, $X=(CHR_5)_n$, $R_2$ and $R_7$ are H, $R_1$ is Cl, $R_8$ is $CH_3$; $R_3$, $R_4$, $R_5$, $R_{10}$, n and Q in Table 84 are the same as that of Table 2.

Table 85: Wherein for formula I-1, $NR_{10}$—CO-Q is at the 4-position of benzene ring, $G_1$ is N, $G_2$ is $CR_7$, $G_3$ is $CR_8$, $X=(CHR_5)_n$, $R_2$ and $R_7$ are H, $R_1$ is Cl, $R_8$ is $CH_3$; $R_3$, $R_4$, $R_5$, $R_{10}$, n and Q in Table 85 are the same as that of Table 2.

Table 86: Wherein for formula I-13, $NR_{10}$—CO-Q is at the 4-position of benzene ring, $G_1$ is $CR_6$, $G_2$ is $CR_7$, $G_3$ is $CR_8$, $X=(CHR_5)_n$, $R_1$, $R_2$, $R_6$ and $R_7$ are H, $R_3$ is Cl; $R_3$, $R_4$, $R_5$, $R_{10}$, n and Q in Table 86 are the same as that of Table 2.

Table 87: Wherein for formula I-13, $NR_{10}$—CO-Q is at the 4-position of benzene ring, $G_1$ is $CR_6$, $G_2$ is $CR_7$, $G_3$ is $CR_8$, $X=(CHR_5)_n$, $R_1$, $R_2$, $R_6$ and $R_7$ are H, $R_8$ is Cl; $R_3$, $R_4$, $R_5$, $R_{10}$, n and Q in Table 87 are the same as that of Table 2.

Table 88: Wherein for formula I-13, $NR_{10}$—CO-Q is at the 4-position of benzene ring, $G_1$ is $CR_6$, $G_2$ is $CR_7$, $G_3$ is $CR_8$, X=(CHR$_5$)$_n$, R$_2$, R$_6$ and R$_7$ are H, R$_1$ is Cl; R$_8$ is CF$_3$, R$_3$, R$_4$, R$_5$, R$_{10}$, n and Q in Table 88 are the same as that of Table 2.

Table 89: Wherein for formula I-13, NR$_{10}$—CO-Q is at the 4-position of benzene ring, G$_1$ is CR$_6$, G$_2$ is CR$_7$, G$_3$ is CR$_8$, X=(CHR$_5$)$_n$, R$_2$, R$_6$ and R$_7$ are H, R$_1$ is NO$_2$, R$_8$ is CF$_3$; R$_3$, R$_4$, R$_5$, R$_{10}$, n and Q in Table 89 are the same as that of Table 2.

Table 90: Wherein for formula I-13, NR$_{10}$—CO-Q is at the 4-position of benzene ring, G$_1$ is CR$_6$, G$_2$ is CR$_7$, G$_3$ is CR$_8$, X=(CHR$_5$)$_n$, R$_2$ and R$_7$ are H, R$_1$, and R$_6$ are Cl, R$_8$ is CF$_3$; R$_3$, R$_4$, R$_5$, R$_{10}$, n and Q in Table 90 are the same as that of Table 2.

Table 91: Wherein for formula I-13, NR$_{10}$—CO-Q is at the 4-position of benzene ring, G$_1$ is CR$_6$, G$_2$ is CR$_7$, G$_3$ is CR$_8$, X=(CHR$_5$)$_n$, R$_2$ and R$_7$ are H, R$_1$ and R$_6$ are NO$_2$, R$_8$ is CF$_3$; R$_3$, R$_4$, R$_5$, R$_{10}$, n and Q in Table 91 are the same as that of Table 2.

Table 92: Wherein for formula I-13, NR$_{10}$—CO-Q is at the 4-position of benzene ring, G$_1$ is CR$_6$, G$_2$ is CR$_7$, G$_3$ is CR$_8$, X=(CHR$_5$)$_n$, R$_2$ and R$_7$ are H, R$_1$ and R$_6$ are Cl, R$_8$ is CN; R$_3$, R$_4$, R$_5$, R$_{10}$, n and Q in Table 92 are the same as that of Table 2.

Table 93: Wherein for formula I-13, NR$_{10}$—CO-Q is at the 4-position of benzene ring, G$_1$ is CR$_6$, G$_2$ is CR$_7$, G$_3$ is CR$_8$, X=(CHR$_5$)$_n$, R$_1$ and R$_6$ are NO$_2$, R$_2$ is C$_1$, R$_7$ is H, R$_8$ is CF$_3$; R$_3$, R$_4$, R$_5$, R$_{10}$, n and Q in Table 93 are the same as that of Table 2.

Table 94: Wherein for formula I-13, NR$_{10}$—CO-Q is at the 4-position of benzene ring, G$_1$ is N, G$_2$ is CR$_7$, G$_3$ is CR$_8$, X=(CHR$_5$)$_n$, R$_1$ is C$_1$, R$_2$, R$_7$ and R$_8$ are H; R$_3$, R$_4$, R$_5$, R$_{10}$, n and Q in Table 94 are the same as that of Table 2.

Table 95: Wherein for formula I-13, NR$_{10}$—CO-Q is at the 4-position of benzene ring, G$_1$ is N, G$_2$ is CR$_7$, G$_3$ is CR$_8$, X=(CHR$_5$)$_n$, R$_8$ is CF$_3$, R$_4$, R) and R$_7$ are H; R$_3$, R$_4$, R$_5$, R$_{10}$, n and Q in Table 95 are the same as that of Table 2.

Table 96: Wherein for formula I-13, NR$_{10}$—CO-Q is at the 4-position of benzene ring, G$_1$ is N, G$_2$ is CR$_7$, G$_3$ is CR$_8$, X=(CHR$_5$)$_n$, R$_1$ is Cl, R$_8$ is CN, R$_2$ and R$_7$ are H; R$_3$, R$_4$, R$_5$, R$_{10}$, n and Q in Table 96 are the same as that of Table 2.

Table 97: Wherein for formula I-13, NR$_{10}$—CO-Q is at the 4-position of benzene ring, G$_1$ is N, G$_2$ is CR$_7$, G$_3$ is CR$_8$, X=(CHR$_5$)$_n$, R$_1$ is Cl, R$_8$ is CN, R$_2$ and R$_7$ are H; R$_3$, R$_4$, R$_5$, R$_{10}$, n and Q in Table 97 are the same as that of Table 2.

Table 98: Wherein for formula I-13, NR$_{10}$—CO-Q is at the 4-position of benzene ring, G$_1$ is N, G$_2$ is CR$_7$, G$_3$ is CR$_8$, X=(CHR$_5$)$_n$, R$_1$ is H, R$_2$ is CF$_3$, R$_7$ is Cl, R$_8$ is CN; R$_3$, R$_4$, R$_5$, R$_{10}$, n and Q in Table 98 are the same as that of Table 2.

Table 99: Wherein for formula I-13, NR$_{10}$—CO-Q is at the 4-position of benzene ring, G$_1$ is N, G$_2$ is CR$_7$, G$_3$ is CR$_8$, X=(CHR$_5$)$_n$, R$_1$ is H, R$_2$ is CH$_3$, R$_7$ is Cl, R$_8$ is CN; R$_3$, R$_4$, R$_5$, R$_{10}$, n and Q in Table 99 are the same as that of Table 2.

Table 100: Wherein for formula I-13, NR$_{10}$—CO-Q is at the 4-position of benzene ring, G$_1$ is N, G$_2$ is CR$_7$, G$_3$ is CR$_8$, X=(CHR$_5$)$_n$, R$_1$ is CN, R$_2$ is CH$_3$, R$_7$ is CH$_3$, R$_8$ is H; R$_3$, R$_4$, R$_5$, R$_{10}$, n and Q in Table 100 are the same as that of Table 2.

Table 101: Wherein for formula I-13, NR$_{10}$—CO-Q is at the 4-position of benzene ring, G$_1$ is N, G$_2$ is CR$_7$, G$_3$ is CR$_8$, X=(CHR$_5$)$_n$, R$_1$ is C$_1$, R$_2$ is H, R$_7$ and R$_8$ are Cl; R$_3$, R$_4$, R$_5$, R$_{10}$, n and Q in Table 101 are the same as that of Table 2.

Table 102: Wherein for formula I-13, NR$_{10}$—CO-Q is at the 4-position of benzene ring, G$_1$ and G$_3$ are N, G$_2$ is CR$_7$, X=(CHR$_5$)$_n$, R$_1$ is C$_1$, R$_2$ is CH$_3$, R$_7$ is H; R$_3$, R$_4$, R$_5$, R$_{10}$, n and Q in Table 102 are the same as that of Table 2.

Table 103: Wherein for formula I-13, NR$_{10}$—CO-Q is at the 4-position of benzene ring, G$_1$ and G$_3$ are N, G$_2$ is CR$_7$, X=(CHR$_5$)$_n$, R$_1$ is H, R$_2$ is CF$_3$, R$_7$ is CH(CH$_3$)$_2$O; R$_3$, R$_4$, R$_5$, R$_{10}$, n and Q in Table 103 are the same as that of Table 2.

Table 104: Wherein for formula I-13, NR$_{10}$—CO-Q is at the 4-position of benzene ring, G$_1$ and G$_3$ are N, G$_2$ is CR$_7$, X=(CHR$_5$)$_n$, R$_1$ is H, R$_2$ is CF$_3$, R$_7$ is cyclopropyl; R$_3$, R$_4$, R$_5$, R$_{10}$, n and Q in Table 104 are the same as that of Table 2.

Table 105: Wherein for formula I-13, NR$_{10}$—CO-Q is at the 4-position of benzene ring, G$_1$ and G$_3$ are N, G$_2$ is CR$_7$, X=(CHR$_5$)$_n$, R$_1$ is CH$_3$, R$_2$ is Ph, R$_7$ is CH$_3$; R$_3$, R$_4$, R$_5$, R$_{10}$, n and Q in Table 105 are the same as that of Table 2.

Table 106: Wherein for formula I-13, NR$_{10}$—CO-Q is at the 4-position of benzene ring, G$_1$ and G$_3$ are N, G$_2$ is CR$_7$, X=(CHR$_5$)$_n$, R$_1$ is CH$_3$, R$_2$ is 4-Cl-Ph, R$_7$ is CH$_3$; R$_3$, R$_4$, R$_5$, R$_{10}$, n and Q in Table 106 are the same as that of Table 2.

Table 107: Wherein for formula I-13, NR$_{10}$—CO-Q is at the 4-position of benzene ring, G$_1$ and G$_3$ are N, G$_2$ is CR$_7$, X=(CHR$_5$)$_n$, R$_1$ is CH$_3$, R$_2$ is 4-CH$_3$O-Ph, R$_7$ is CH$_3$; R$_3$, R$_4$, R$_5$, R$_{10}$, n and Q in Table 107 are the same as that of Table 2.

Table 108: Wherein for formula I-13, NR$_{10}$—CO-Q is at the 4-position of benzene ring, G$_1$ and G$_3$ are N, G$_2$ is CR$_7$, X=(CHR$_5$)$_n$, R$_1$ and R$_7$ are H, R$_2$ is Cl; R$_3$, R$_4$, R$_5$, R$_{10}$, n and Q in Table 108 are the same as that of Table 2.

Table 109: Wherein for formula I-13, NR$_{10}$—CO-Q is at the 4-position of benzene ring, G$_1$ and G$_3$ are N, G$_2$ is CR$_7$, X=(CHR$_5$)$_n$, R$_1$ is F, R$_2$ is C$_1$, R$_7$ is H; R$_3$, R$_4$, R$_5$, R$_{10}$, n and Q in Table 109 are the same as that of Table 2.

Table 110: Wherein for formula I-13, NR$_{10}$—CO-Q is at the 4-position of benzene ring, G$_1$ and G$_3$ are N, G$_2$ is CR$_7$, X=(CHR$_5$)$_n$, R$_1$ is H, R$_2$ is CH$_3$, R$_7$ is CH$_3$O; R$_3$, R$_4$, R$_5$, R$_{10}$, n and Q in Table 110 are the same as that of Table 2.

Table 111: Wherein for formula I-13, NR$_{10}$—CO-Q is at the 4-position of benzene ring, G$_1$ and G$_3$ are N, G$_2$ is CR$_7$, X=(CHR$_5$)$_n$, R$_1$ is H, R$_2$ is CH$_3$, R$_7$ is (C$_2$H$_5$)$_2$N; R$_3$, R$_4$, R$_5$, R$_{10}$, n and Q in Table 111 are the same as that of Table 2.

Table 112: Wherein for formula I-13, NR$_{10}$—CO-Q is at the 4-position of benzene ring, G$_1$ and G$_3$ are N, G$_2$ is CR$_7$, X=(CHR$_5$)$_n$, R$_1$ is H, R$_2$ is CF$_3$, R$_7$ is CH$_3$O; R$_3$, R$_4$, R$_5$, R$_{10}$, n and Q in Table 112 are the same as that of Table 2.

Table 113: Wherein for formula I-13, NR$_{10}$—CO-Q is at the 4-position of benzene ring, G$_1$ and G$_3$ are N, G$_2$ is CR$_7$, X=(CHR$_5$)$_n$, R$_1$ is H, R$_2$ is CF$_3$, R$_7$ is (C$_2$H$_5$)$_2$N; R$_3$, R$_4$, R$_5$, R$_{10}$, n and Q in Table 113 are the same as that of Table 2.

Table 114: Wherein for formula I-13, NR$_{10}$—CO-Q is at the 4-position of benzene ring, G$_1$ and G$_3$ are N, G$_2$ is CR$_7$, X=(CHR$_5$)$_n$, R$_1$ is H, R$_2$ is CH$_3$, R$_7$ is CH$_3$CH$_2$CH$_2$; R$_3$, R$_4$, R$_5$, R$_{10}$, n and Q in Table 114 are the same as that of Table 2.

Table 115: Wherein for formula I-13, NR$_{10}$—CO-Q is at the 4-position of benzene ring, G$_1$ and G$_3$ are N, G$_2$ is CR$_7$, X=(CHR$_5$)$_n$, R$_1$ is C$_4$H$_9$, R$_2$ is CH$_3$, R$_7$ is (C$_2$H$_5$)$_2$N; R$_3$, R$_4$, R$_5$, R$_{10}$, n and Q in Table 115 are the same as that of Table 2.

Table 116: Wherein for formula I-13, NR$_{10}$—CO-Q is at the 4-position of benzene ring, G$_1$ and G$_3$ are N, G$_2$ is CR$_7$, X=(CHR$_5$)$_n$, R$_1$ is C$_4$H$_9$, R$_2$ is CH$_3$, R$_7$ is C$_2$H$_5$NH; R$_3$, R$_4$, R$_5$, R$_{10}$, n and Q in Table 116 are the same as that of Table 2.

Table 117: Wherein for formula I-13, NR$_{10}$—CO-Q is at the 4-position of benzene ring, G$_1$ and G$_3$ are N, G$_2$ is CR$_7$, X=(CHR$_5$)$_n$, R$_1$ is H, R$_2$ is CH$_3$, R$_7$ is Ph-NH; R$_3$, R$_4$, R$_5$, R$_{10}$, n and Q in Table 117 are the same as that of Table 2.

Table 118: Wherein for formula I-13, NR$_{10}$—CO-Q is at the 4-position of benzene ring, G$_1$ and G$_3$ are N, G$_2$ is CR$_7$, X=(CHR$_5$)$_n$, R$_1$ is H, R$_2$ is CF$_3$, R$_7$ is 4-Cl-Ph-NH; R$_3$, R$_4$, R$_5$, R$_{10}$, n and Q in Table 118 are the same as that of Table 2.

Table 119: Wherein for formula I-13, NR$_{10}$—CO-Q is at the 4-position of benzene ring, G$_1$ and G$_3$ are N, G$_2$ is CR$_7$, X=(CHR$_5$)$_n$, R$_1$ is H, R$_2$ is CF$_3$, R$_7$ is Ph-NH; R$_3$, R$_4$, R$_5$, R$_{10}$, n and Q in Table 119 are the same as that of Table 2.

Table 120: Wherein for formula I-13, NR$_{10}$—CO-Q is at the 4-position of benzene ring, G$_1$ and G$_3$ are N, G$_2$ is CR$_7$, X=(CHR$_5$)$_n$, R$_1$ is H, R$_2$ is CH$_3$, R$_7$ is 4-Cl-Ph-NH; R$_3$, R$_4$, R$_5$, R$_{10}$, n and Q in Table 120 are the same as that of Table 2.

Table 121: Wherein for formula I-13, NR$_{10}$—CO-Q is at the 4-position of benzene ring, G$_1$ and G$_2$ are N, G$_3$ is CR$_8$, X=(CHR$_5$)$_n$, R$_1$ and R$_7$ are H, R$_8$ is Cl; R$_3$, R$_4$, R$_5$, R$_{10}$, n and Q in Table 121 are the same as that of Table 2.

Table 122: Wherein for formula I-13, NR$_{10}$—CO-Q is at the 4-position of benzene ring, G$_1$ and G$_2$ are N, G$_3$ is CR$_8$, X=(CHR$_5$)$_n$, R$_1$, R$_2$ and R$_8$ are H; R$_3$, R$_4$, R$_5$, R$_{10}$, n and Q in Table 122 are the same as that of Table 2.

Table 123: Wherein for formula I-13, NR$_{10}$—CO-Q is at the 4-position of benzene ring, G$_1$ and G$_2$ are N, G$_3$ is CR$_8$, X=(CHR$_5$)$_n$, R$_1$ and R$_2$ are H, R$_8$ is Ph; R$_3$, R$_4$, R$_5$, R$_{10}$, n and Q in Table 123 are the same as that of Table 2.

Table 124: Wherein for formula I-13, NR$_{10}$—CO-Q is at the 4-position of benzene ring, G$_1$ is CR$_6$, G$_2$ is CR$_7$, G$_3$ is CR$_8$, X=(CHR$_5$)$_n$, R$_1$, R$_6$, R$_7$ and R$_8$ are H, R$_2$ is C(CH$_3$)$_3$; R$_3$, R$_4$, R$_5$, R$_{10}$, n and Q in Table 124 are the same as that of Table 2.

Table 125: Wherein for formula I-13, NR$_{10}$—CO-Q is at the 4-position of benzene ring, G$_1$ is N, G$_2$ is CR$_7$, G$_3$ is CR$_8$, X=(CHR$_5$)$_n$, R$_2$ and R$_7$ are H, R$_1$ is Cl, R$_8$ is CH$_3$; R$_3$, R$_4$, R$_5$, R$_{10}$, n and Q in Table 125 are the same as that of Table 2.

Table 126: Wherein for formula I-13, NR$_{10}$—CO-Q is at the 4-position of benzene ring, G$_1$ is N, G$_2$ is CR$_7$, G$_3$ is CR$_8$, X=(CHR$_5$)$_n$, R$_2$ and R$_7$ are H, R$_1$ and R$_8$ are Cl; R$_3$, R$_4$, R$_5$, R$_{10}$, n and Q in Table 126 are the same as that of Table 2.

Table 127: Wherein for formula I-13, NR$_{10}$—CO-Q is at the 4-position of benzene ring, G$_1$ is N, G$_2$ is CR$_7$, G$_3$ is CR$_8$, X=(CHR$_5$)$_n$, R$_2$ and R$_7$ are H, R$_1$ and R$_8$ are Cl; R$_3$, R$_4$, R$_5$, R$_{10}$, n and Q in Table 127 are the same as that of Table 2.

Table 128: Wherein for formula I-18, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_1$, R$_2$, R$_6$ and R$_7$ are H, R$_8$ is Cl; R$_3$, R$_4$, R$_5$, R$_{10}$, n and Q in Table 128 are the same as that of Table 2.

Table 129: Wherein for formula I-18, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_1$, R$_2$, R$_6$ and R$_7$ are H, R$_8$ is CN; R$_3$, R$_4$, R$_5$, R$_{10}$, n and Q in Table 129 are the same as that of Table 2.

Table 130: Wherein for formula I-18, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_1$, R$_2$, R$_6$ and R$_7$ are H, R$_8$ is CF$_3$; R$_3$, R$_4$, R$_5$, R$_{10}$, n and Q in Table 130 are the same as that of Table 2.

Table 131: Wherein for formula I-18, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_2$, R$_6$ and R$_7$ are H, R$_1$ is Cl, R$_8$ is CF$_3$; R$_3$, R$_4$, R$_5$, R$_{10}$, n and Q in Table 131 are the same as that of Table 2.

Table 132: Wherein for formula I-18, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_2$, R$_6$ and R$_7$ are H, R$_1$ is NO$_2$, R$_8$ is CF$_3$; R$_3$, R$_4$, R$_5$, R$_{10}$, n and Q in Table 132 are the same as that of Table 2.

Table 133: Wherein for formula I-18, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_2$ and R$_7$ are H, R$_1$ and R$_6$ are Cl, R$_8$ is CF$_3$; R$_3$, R$_4$, R$_5$, R$_{10}$, n and Q in Table 133 are the same as that of Table 2.

Table 134: Wherein for formula I-18, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_2$ and R$_7$ are 14, R$_1$ and R$_6$ are NO$_2$, R$_8$ is CF$_3$; R$_3$, R$_4$, R$_5$, R$_{10}$, n and Q in Table 134 are the same as that of Table 2.

Table 135: Wherein for formula I-18, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_2$ and R$_7$ are H, R$_1$ and R$_6$ are Cl, R$_8$ is CN; R$_3$, R$_4$, R$_5$, R$_{10}$, n and Q in Table 135 are the same as that of Table 2.

Table 136: Wherein for formula I-18, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_1$ and R$_6$ are NO$_2$, R$_2$ is C$_1$, R$_7$ is H, R$_8$ is CF$_3$; R$_3$, R$_4$, R$_5$, R$_{10}$, n and Q in Table 136 are the same as that of Table 2.

Table 137: Wherein for formula I-18, NR$_{10}$—CO-Q is at the 2-position of benzene ring, G$_1$ is N, G$_2$ is CR$_7$, G$_3$ is CR$_8$, X=(CHR$_5$)$_n$, R$_1$ is C$_1$, R$_2$, R$_7$ and R$_8$ are H; R$_3$, R$_4$, R$_5$, R$_{10}$, n and Q in Table 137 are the same as that of Table 2.

Table 138: Wherein for formula I-18, NR$_{10}$—CO-Q is at the 2-position of benzene ring, G$_1$ is N, G$_2$ is CR$_7$, G$_3$ is CR$_8$, X=(CHR$_5$)$_n$, R$_8$ is CF$_3$, R$_4$, R$_2$ and R$_7$ are H; R$_3$, R$_4$, R$_5$, R$_{10}$, n and Q in Table 138 are the same as that of Table 2.

Table 139: Wherein for formula I-18, NR$_{10}$—CO-Q is at the 2-position of benzene ring, G$_1$ is N, G$_2$ is CR$_7$, G$_3$ is CR$_8$, X=(CHR$_5$)$_n$, R$_1$ is Cl, R$_8$ is CF$_3$, R$_2$ and R$_7$ are H; R$_3$, R$_4$, R$_5$, R$_{10}$, n and Q in Table 139 are the same as that of Table 2.

Table 140: Wherein for formula I-18, NR$_{10}$—CO-Q is at the 2-position of benzene ring, G$_1$ is N, G$_2$ is CR$_7$, G$_3$ is CR$_8$, X=(CHR$_5$)$_n$, R$_1$ is Cl, R$_8$ is CN, R$_2$ and R$_7$ are H; R$_3$, R$_4$, R$_5$, R$_{10}$, n and Q in Table 140 are the same as that of Table 2.

Table 141: Wherein for formula I-18, NR$_{10}$—CO-Q is at the 2-position of benzene ring, G$_1$ is N. G$_2$ is CR$_7$, G$_3$ is CR$_8$, X=(CHR$_5$)$_n$, R$_1$ is H, R$_8$ is CF$_3$, R$_2$ and R$_7$ are H; R$_3$, R$_4$, R$_5$, R$_{10}$, n and Q in Table 141 are the same as that of Table 2.

Table 142: Wherein for formula I-18, NR$_{10}$—CO-Q is at the 2-position of benzene ring, G$_1$ is N, G$_2$ is CR$_7$, G$_3$ is CR$_8$, X=(CHR$_5$)$_n$, R$_1$ is H, R$_2$ is CH$_3$, R$_7$ is Cl, R$_8$ is CN; R$_3$, R$_4$, R$_5$, R$_{10}$, n and Q in Table 142 are the same as that of Table 2.

Table 143: Wherein for formula I-18, NR$_{10}$—CO-Q is at the 2-position of benzene ring, G$_1$ is N, G$_2$ is CR$_7$, G$_3$ is CR$_8$, X=(CHR$_5$)$_n$, R$_1$ is CN, R$_2$ is CH$_3$, R$_7$ is CH$_3$, R$_8$ is H; R$_3$, R$_4$, R$_5$, R$_{10}$, n and Q in Table 143 are the same as that of Table 2.

Table 144: Wherein for formula I-18, NR$_{10}$—CO-Q is at the 2-position of benzene ring, G$_1$ is N, G$_2$ is CR$_7$, G$_3$ is CR$_8$, X=(CHR$_5$)$_n$, R$_1$ is C$_1$, R$_2$ is H, R$_7$ and R$_8$ are Cl; R$_3$, R$_4$, R$_5$, R$_{10}$, n and Q in Table 144 are the same as that of Table 2.

Table 145: Wherein for formula I-18, NR$_{10}$—CO-Q is at the 2-position of benzene ring, G$_1$ and G$_3$ are N, G$_2$ is CR$_7$, X=(CHR$_5$)$_n$, R$_1$ is C$_1$, R$_2$ is CH$_3$, R$_7$ is H; R$_1$, R$_4$, R$_5$, R$_{10}$, n and Q in Table 145 are the same as that of Table 2.

Table 146: Wherein for formula I-18, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CF$_3$, R$_7$ is CH(CH$_3$)$_2$O; R$_3$, R$_4$, R$_5$, R$_{10}$, n and Q in Table 146 are the same as that of Table 2.

Table 147: Wherein for formula I-18, NR$_{40}$—CO-Q is at the 2-position or benzene ring, G$_1$ and G$_3$ are N, G$_2$ is CR$_7$, X=(CHR$_5$)$_n$, R$_1$ is H, R$_2$ is CF$_3$, R$_7$ is cyclopropyl; R$_3$, R$_4$, R$_5$, R$_{10}$, n and Q in Table 147 are the same as that of Table 2.

Table 148: Wherein for formula I-18, NR$_{10}$—CO-Q is at the 2-position of benzene ring, G$_1$ and G$_3$ are N, G$_2$ is CR$_7$, X=(CHR$_5$)$_n$, R$_1$ is CH$_3$, R$_2$ is Ph, R$_7$ is CH$_3$; R$_3$, R$_4$, R$_5$, R$_{10}$, n and Q in Table 148 are the same as that of Table 2.

Table 149: Wherein for formula I-18, NR$_{10}$—CO-Q is at the 2-position of benzene ring, G$_1$ and G$_3$ are N, G$_2$ is CR$_7$, X=(CHR$_5$)$_n$, R$_1$ is CH$_3$, R$_2$ is 4-Cl-Ph, R$_7$ is CH$_3$; R$_3$, R$_4$, R$_5$, R$_{10}$, n and Q in Table 149 are the same as that of Table 2.

Table 150: Wherein for formula I-18, NR$_{10}$—CO-Q is at the 2-position of benzene ring, G$_1$ and G$_3$ are N, G$_2$ is CR$_7$, X=(CHR$_5$)$_n$, R$_1$ is CH$_3$, R$_2$ is 4-CH$_3$O-Ph, R$_7$ is CH$_3$; R$_3$, R$_4$, R$_5$, R$_{10}$, n and Q in Table 150 are the same as that of Table 2.

Table 151: Wherein for formula I-18, NR$_{10}$—CO-Q is at the 2-position of benzene ring, G$_1$ and G$_3$ are N, G$_2$ is CR$_7$, X=(CHR$_5$)$_n$, R$_1$, and R$_7$ are H, R$_2$ is Cl; R$_3$, R$_4$, R$_5$, R$_{10}$, n and Q in Table 151 are the same as that of Table 2.

Table 152: Wherein for formula I-18, NR$_{10}$—CO-Q is at the 2-position of benzene ring, G$_1$ and G$_3$ are N, G$_2$ is CR$_7$, X=(CHR$_5$)$_n$, R$_1$ is F, R$_2$ is C$_1$, R$_7$ is H; R$_3$, R$_4$, R$_5$, R$_{10}$, n and Q in Table 152 are the same as that of Table 2.

Table 153: Wherein for formula I-18, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CH$_3$, R$_7$ is CH$_3$O; R$_3$, R$_4$, R$_5$, R$_{10}$, n and Q in Table 153 are the same as that of Table 2.

Table 154: Wherein for formula I-18, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CH$_3$, R$_7$ is (C$_2$H$_5$)$_2$N; R$_3$, R$_4$, R$_5$, R$_{10}$, n and Q in Table 154 are the same as that of Table 2.

Table 155: Wherein for formula I-18, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CF$_3$, R$_7$ is CH$_3$O; R$_3$, R$_4$, R$_5$, R$_{10}$, n and Q in Table 155 are the same as that of Table 2.

Table 156: Wherein for formula I-18, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CF$_3$, R$_7$ is (C$_2$H$_5$)$_2$N; R$_3$, R$_4$, R$_5$, R$_{10}$, n and Q in Table 156 are the same as that of Table 2.

Table 157: Wherein for formula I-18, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CH$_3$, R$_7$ is CH$_3$CH$_2$CH$_2$; R$_3$, R$_4$, R$_5$, R$_{10}$, n and Q in Table 157 are the same as that of Table 2.

Table 158: Wherein for formula I-18, NR$_{10}$—CO-Q is at the 2-position of benzene ring, G$_1$ and G$_3$ are N, G$_2$ is CR$_7$, X=(CHR$_5$)$_n$, R$_1$ is C$_4$H$_9$, R$_2$ is CH$_3$, R$_7$ is (C$_2$H$_5$)$_2$N; R$_3$, R$_4$, R$_5$, R$_{10}$, n and Q in Table 158 are the same as that of Table 2.

Table 159: Wherein for formula I-18, NR$_{10}$—CO-Q is at the 2-position of benzene ring, G$_1$ and G$_3$ are N, G$_2$ is CR$_7$, X=(CHR$_5$)$_n$, R$_1$ is C$_4$H$_9$, R$_2$ is CH$_3$, R$_7$ is C$_2$H$_5$NH; R$_3$, R$_4$, R$_5$, R$_{10}$, n and Q in Table 159 are the same as that of Table 2.

Table 160: Wherein for formula I-18, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CH$_3$, R$_7$ is Ph-NH; R$_3$, R$_4$, R$_5$, R$_{10}$, n and Q in Table 160 are the same as that of Table 2.

Table 161: Wherein for formula I-18, NR$_{10}$—CO-Q is at the 2-position of benzene ring, G$_1$ and G$_3$ are N, G$_2$ is CR$_7$, X=(CHR$_5$)$_n$, R$_1$ is H, R$_7$ is CF$_3$, R$_7$ is 4-Cl-Ph-NH; R$_3$, R$_4$, R$_5$, R$_{10}$, n and Q in Table 161 are the same as that of Table 2.

Table 162: Wherein for formula I-18, NR$_{10}$—CO-Q is at the 2-position of benzene ring, G and G$_3$ are N, G$_2$ is CR$_7$, X=(CHR$_5$)$_n$, R$_1$ is H, R$_2$ is CF$_3$, R$_7$ is Ph-NH; R$_3$, R$_4$, R$_5$, R$_{10}$, n and Q in Table 162 are the same as that of Table 2.

Table 163: Wherein for formula I-18, NR$_{10}$—CO-Q is at the 2-position of benzene ring, G$_1$ and G$_3$ are N, G$_2$ is CR$_7$, X=(CHR$_5$)$_n$, R$_1$ is 14, R$_2$ is CH$_3$, R$_7$ is 4-Cl-Ph-NH; R$_3$, R$_4$, R$_5$, R$_{10}$, n and Q in Table 163 are the same as that of Table 2.

Table 164: Wherein for formula I-18, NR$_{10}$—CO-Q is at the 2-position of benzene ring, G$_1$ and G$_2$ are N, G$_3$ is CR$_8$, X=(CHR$_5$)$_n$, R$_1$ and R$_2$ are H, R$_8$ is Cl; R$_3$, R$_4$, R$_5$, R$_{10}$, n and Q in Table 164 are the same as that of Table 2.

Table 165: Wherein for formula I-18, NR$_{10}$—CO-Q is at the 2-position of benzene ring, G$_1$ and G$_2$ are N, G$_3$ is CR$_8$, X=(CHR$_5$)$_n$, R$_1$, R$_2$ and R$_8$ are H; R$_3$, R$_4$, R$_5$, R$_{10}$, n and Q in Table 165 are the same as that of Table 2.

Table 166: Wherein for formula I-18, NR$_{10}$—CO-Q is at the 2-position of benzene ring, G$_1$ and G$_2$ are N, G$_3$ is CR$_8$, X=(CHR$_5$)$_n$, R$_1$ and R$_2$ are H, R$_8$ is Ph; R$_3$, R$_4$, R$_5$, R$_{10}$, n and Q in Table 166 are the same as that of Table 2.

Table 167: Wherein for formula I-18, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_1$, R$_6$, R$_7$ and R$_8$ are H, R$_2$ is C(CH$_3$)$_3$; R$_3$, R$_4$, R$_5$, R$_{10}$, n and Q in Table 167 are the same as that of Table 2.

Table 168: Wherein for formula I-18, NR$_{10}$—CO-Q is at the 2-position of benzene ring, G$_1$ is N, G$_2$ is CR$_7$, G$_3$ is CR$_8$, X=(CHR$_5$)$_n$, R$_2$ and R$_7$ are H, R$_1$ and R$_8$ are Cl; R$_3$, R$_4$, R$_5$, R$_{10}$, n and Q in Table 168 are the same as that of Table 2.

Table 169: Wherein for formula I-18, NR$_{10}$—CO-Q is at the 2-position of benzene ring, G$_1$ is N, G$_2$ is CR$_7$, G$_3$ is CR$_8$, X=(CHR$_5$)$_n$, R$_2$ and R$_7$ are H, R$_1$, is Cl, R$_8$ is CH$_3$; R$_3$, R$_4$, R$_5$, R$_{10}$, n and Q in Table 169 are the same as that of Table 2.

Table 170: Wherein for formula I-19, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_1$, R$_2$, R$_6$ and R$_7$ are H, R$_8$ is Cl; R$_3$, R$_4$, R$_5$, R$_{10}$, n and Q in Table 170 are the same as that of Table 2.

Table 171: Wherein for formula I-19, NR$_{10}$—CO-Q is at the 2-position of benzene ring, G$_1$ is CR$_6$; G$_2$ is CR$_7$, G$_3$ is CR$_8$, X=(CHR$_5$)$_n$, R$_1$, R$_2$, R$_6$ and R$_7$ are H, R$_8$ is CN; R$_3$, R$_4$, R$_5$, R$_{10}$, n and Q in Table 171 are the same as that of Table 2.

Table 172: Wherein for formula I-19, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_1$, R$_2$, R$_6$ and R$_7$ are H, R$_8$ is CF$_3$; R$_3$, R$_4$, R$_5$, R$_{10}$, n and Q in Table 172 are the same as that of Table 2.

Table 173: Wherein for formula I-19, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_2$, R$_6$ and R$_7$ are H, R$_1$ is Cl, R$_8$ is CF$_3$; R$_3$, R$_4$, R$_5$, R$_{10}$, n and Q in Table 173 are the same as that of Table 2.

Table 174: Wherein for formula I-19, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_2$, R$_6$ and R$_7$ are H, R$_1$ is NO$_2$, R$_8$ is CF$_3$; R$_3$, R$_4$, R$_5$, R$_{10}$, n and Q in Table 174 are the same as that of Table 2.

Table 175: Wherein for formula I-19, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_2$ and R$_7$ are H, R$_1$, and R$_6$ are Cl, R$_8$ is CF$_3$; R$_3$, R$_4$, R$_5$, R$_{10}$, n and Q in Table 175 are the same as that of Table 2.

Table 176: Wherein for formula I-19, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_2$ and R$_7$ are H, R$_1$, and R$_6$ are NO$_2$, R$_8$ is CF$_3$; R$_3$, R$_4$, R$_5$, R$_{10}$, n and Q in Table 176 are the same as that of Table 2.

Table 177: Wherein for formula I-19, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_2$ and R$_7$ are H, R$_1$, and R$_6$ are Cl, R$_8$ is CN; R$_3$, R$_1$, R$_5$, R$_{10}$, and Q in Table 177 are the same as that of Table 2.

Table 178: Wherein for formula I-19, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_1$, and R$_6$ are NO$_2$, R$_2$ is C$_1$, R$_7$ is H, R$_8$ is CF$_3$; R$_3$, R$_4$, R$_5$, R$_{10}$, n and Q in Table 178 are the same as that of Table 2.

Table 179: Wherein for formula I-19, NR$_{10}$—CO-Q is at the 2-position of benzene ring, G$_1$ is N, G$_2$ is CR$_7$, G$_3$ is CR$_8$, X=(CHR$_5$)$_n$, R$_1$ is C$_1$, R$_2$, R$_7$ and R$_8$ are H; R$_3$, R$_4$, R$_5$, R$_{10}$; n and Q in Table 179 are the same as that of Table 2.

Table 180: Wherein for formula I-19, NR$_{10}$—CO-Q is at the 2-position of benzene ring, G$_1$ is N, G$_2$ is CR$_7$, G$_3$ is CR$_8$, X=(CHR$_5$)$_n$, R$_8$ is R$_3$, R$_4$, R$_2$ and R$_7$ are H; R$_3$, R$_4$, R$_5$, R$_{10}$, n and Q in Table 180 are the same as that of Table 2.

Table 181: Wherein for formula I-19, NR$_{10}$—CO-Q is at the 2-position of benzene ring, G$_1$ is N, G$_2$ is CR$_7$, G$_3$ is CR$_8$, X=(CHR$_5$)$_n$, R$_1$ is Cl, R$_8$ is CF$_3$, R$_2$ and R$_7$ are H; R$_3$, R$_4$, R$_5$, R$_{10}$, n and Q in Table 181 are the same as that of Table 2.

Table 182: Wherein for formula I-19, NR$_{10}$—CO-Q is at the 2-position of benzene ring, G$_1$ is N, G$_2$ is CR$_7$, G$_3$ is CR$_8$, X=(CHR$_5$)$_n$, R$_1$ is Cl, R$_8$ is CN, R$_2$ and R$_7$ are H; R$_3$, R$_4$, R$_5$, R$_{10}$, n and Q in Table 182 are the same as that of Table 2.

Table 183: Wherein for formula I-19, $NR_{10}$—CO-Q is at the 2-position of benzene ring, $G_1$ is N, $G_2$ is $CR_7$, $G_3$ is $CR_8$, $X=(CHR_5)_n$, $R_1$ is H, $R_2$ is $CF_3$, $R_7$ is Cl, $R_8$ is CN; $R_3$, $R_4$, $R_5$, $R_{10}$, n and Q in Table 183 are the same as that of Table 2.

Table 184: Wherein for formula I-19, $NR_{10}$—CO-Q is at the 2-position of benzene ring, $G_1$ is N, $G_2$ is $CR_7$, $G_3$ is $CR_8$, $X=(CHR_5)_n$, $R_1$ is H, $R_2$ is $CH_3$, $R_7$ is Cl, $R_8$ is CN; $R_3$, $R_4$, $R_5$, $R_{10}$, n and Q in Table 184 are the same as that of Table 2.

Table 185: Wherein for formula I-19, $NR_{10}$—CO-Q is at the 2-position of benzene ring, $G_1$ is N, $G_2$ is $CR_7$, $G_3$ is $CR_8$, $X=(CHR_5)_n$, $R_1$ is CN, $R_2$ is $CH_3$, $R_7$ is $CH_3$, $R_8$ is H; $R_3$, $R_4$, $R_5$, $R_{10}$, n and Q in Table 185 are the same as that of Table 2.

Table 186: Wherein for formula I-19, $NR_{10}$—CO-Q is at the 2-position of benzene ring, $G_1$ is N, $G_2$ is $CR_7$, $G_3$ is $CR_8$, $X=(CHR_5)_n$, $R_1$ is $C_1$, $R_2$ is H, $R_7$ and $R_8$ are Cl; $R_3$, $R_4$, $R_5$, $R_{10}$, n and Q in Table 186 are the same as that of Table 2.

Table 187: Wherein for formula I-19, $NR_{10}$—CO-Q is at the 2-position of benzene ring, $G_1$ and $G_3$ are N, $G_2$ is $CR_7$, $X=(CHR_5)_n$, $R_1$ is $C_1$, $R_2$ is $CH_3$, $R_7$ is H; $R_3$, $R_4$, $R_5$, $R_{10}$, n and Q in Table 187 are the same as that of Table 2.

Table 188: Wherein for formula I-19, $NR_{10}$—CO-Q is at the 2-position of benzene ring, $G_1$ and $G_3$ are N, $G_2$ is $CR_7$, $X=(CHR_5)_n$, $R_1$ is H, $R_2$ is $CF_3$, $R_7$ is $CH(CH_3)_2O$; $R_3$, $R_4$, $R_5$, $R_{10}$, n and Q in Table 188 are the same as that of Table 2.

Table 189: Wherein for formula I-19, $NR_{10}$—CO-Q is at the 2-position of benzene ring, $G_1$ and $G_3$ are N, $G_2$ is $CR_7$, $X=(CHR_5)_n$, $R_1$ is H, $R_2$ is $CF_3$, $R_7$ is Cyclopropyl; $R_3$, $R_4$, $R_5$, $R_{10}$, n and Q in Table 189 are the same as that of Table 2.

Table 190: Wherein for formula I-19, $NR_{10}$—CO-Q is at the 2-position of benzene ring, $G_1$ and $G_3$ are N, $G_2$ is $CR_7$, $X=(CHR_5)_n$, $R_1$ is $CH_3$, $R_2$ is Ph, $R_7$ is $CH_3$; $R_3$, $R_4$, $R_5$, $R_{10}$, n and Q in Table 190 are the same as that of Table 2.

Table 191: Wherein for formula I-19, $NR_{10}$—CO-Q is at the 2-position of benzene ring, $G_1$ and $G_3$ are N, $G_2$ is $CR_7$, $X=(CHR_5)_n$, $R_1$ is $CH_3$, $R_2$ is 4-Cl-Ph, $R_7$ is $CH_3$; $R_3$, $R_4$, $R_5$, $R_{10}$, n and Q in Table 191 are the same as that of Table 2.

Table 192: Wherein for formula I-19, $NR_{10}$—CO-Q is at the 2-position of benzene ring, $G_1$ and $G_3$ are N, $G_2$ is $CR_7$, $X=(CHR_5)_n$, $R_1$ is $CH_3$, $R_2$ is 4-$CH_3$O-Ph, $R_7$ is $CH_3$; $R_3$, $R_4$, $R_5$, $R_{10}$, n and Q in Table 192 are the same as that of Table 2.

Table 193: Wherein for formula I-19, $NR_{10}$—CO-Q is at the 2-position of benzene ring, $G_1$ and $G_3$ are N, $G_2$ is $CR_7$, $X=(CHR_5)_n$, $R_1$ and $R_7$ are 1-1, $R_2$ is Cl; $R_3$, $R_4$, $R_5$, $R_{10}$, n and Q in Table 193 are the same as that of Table 2.

Table 194: Wherein for formula I-19, $NR_{10}$—CO-Q is at the 2-position of benzene ring, $G_1$ and $G_3$ are N, $G_2$ is $CR_7$, $X=(CHR_5)_n$, $R_1$ is F, $R_2$ is $C_1$, $R_7$ is H; $R_3$, $R_4$, $R_5$, $R_{10}$, n and Q in Table 194 are the same as that of Table 2.

Table 195: Wherein for formula I-19, $NR_{10}$—CO-Q is at the 2-position of benzene ring, $G_1$ and $G_3$ are N, $G_2$ is $CR_7$, $X=(CHR_5)_n$, $R_1$ is H, $R_2$ is $CH_3$, $R_7$ is $CH_3O$; $R_3$, $R_4$, $R_5$, $R_{10}$, n and Q in Table 195 are the same as that of Table 2.

Table 196: Wherein for formula I-19, $NR_{10}$—CO-Q is at the 2-position of benzene ring, $G_1$ and $G_3$ are N, $G_2$ is $CR_7$, $X=(CHR_5)$, $R_1$ is H, $R_2$ is $CH_3$, $R_7$ is $(C_2H_5)_2N$; $R_3$, $R_4$, $R_5$, $R_{10}$, n and Q in Table 196 are the same as that of Table 2.

Table 197: Wherein for formula I-19, $NR_{10}$—CO-Q is at the 2-position of benzene ring, $G_1$ and $G_3$ are N, $G_2$ is $CR_7$, $X=(CHR_5)_n$, $R_1$ is H, $R_2$ is $CF_3$, $R_7$ is $CH_3O$; $R_3$, $R_4$, $R_5$, $R_{10}$, n and Q in Table 197 are the same as that of Table 2.

Table 198: Wherein for formula I-19, $NR_{10}$—CO-Q is at the 2-position of benzene ring, $G_1$ and $G_3$ are N, $G_2$ is $CR_7$, $X=(CHR_5)_n$, $R_1$ is H, $R_2$ is $CF_3$, $R_7$ is $(C_2H_5)_2N$; $R_3$, $R_4$, $R_5$, $R_{10}$, n and Q in Table 198 are the same as that of Table 2.

Table 199: Wherein for formula I-19, $NR_{10}$—CO-Q is at the 2-position of benzene ring, $G_1$ and $G_3$ are N, $G_2$ is $CR_7$, $X=(CHR_5)_n$, $R_1$ is H, $R_2$ is $CH_3$, $R_7$ is $CH_3CH_2CH_2$; $R_3$, $R_4$, $R_5$, $R_{10}$, n and Q in Table 199 are the same as that of Table 2.

Table 200: Wherein for formula I-19, $NR_{10}$—CO-Q is at the 2-position of benzene ring, $G_1$ and $G_3$ are N, $G_2$ is $CR_7$, $X=(CHR_5)_n$, $R_1$ is $C_4H_9$, $R_2$ is $CH_3$, $R_7$ is $(C_2H_5)_2N$; $R_3$, $R_4$, $R_5$, $R_{10}$, n and Q in Table 200 are the same as that of Table 2.

Table 201: Wherein for formula I-19, $NR_{10}$—CO-Q is at the 2-position of benzene ring, $G_1$ and $G_3$ are N, $G_2$ is $CR_7$, $X=(CHR_5)_n$, $R_1$ is $C_4H_9$, $R_2$ is $CH_3$, $R_7$ is $C_2H_5NH$; $R_3$, $R_4$, $R_5$, $R_{10}$, n and Q in Table 201 are the same as that of Table 2.

Table 202: Wherein for formula I-19, $NR_{10}$—CO-Q is at the 2-position of benzene ring, $G_1$ and $G_3$ are N, $G_2$ is $CR_7$, $X=(CHR_5)_n$, $R_1$ is H, $R_2$ is $CH_3$, $R_7$ is Ph-NH, $R_3$; $R_4$, $R_5$, $R_{10}$, n and Q in Table 202 are the same as that of Table 2.

Table 203: Wherein for formula I-19, $NR_{10}$—CO-Q is at the 2-position of benzene ring, $G_1$ and $G_3$ are N, $G_2$ is $CR_7$, $X=(CHR_5)_n$, $R_1$ is H, $R_2$ is $CF_3$, $R_7$ is 4-Cl-Ph-NH; $R_3$, $R_4$, $R_5$, $R_{10}$, n and Q in Table 203 are the same as that of Table 2.

Table 204: Wherein for formula I-19, $NR_{10}$—CO-Q is at the 2-position of benzene ring, $G_1$ and $G_3$ are N, $G_2$ is $CR_7$, $X=(CHR_5)_n$, $R_1$ is H, $R_2$ is $R_7$ is Ph-NH; $R_3$, $R_4$, $R_5$, $R_{10}$, n and Q in Table 204 are the same as that of Table 2.

Table 205: Wherein for formula I-19, $NR_{10}$—CO-Q is at the 2-position of benzene ring, $G_1$ and $G_3$ are N, $G_2$ is $CR_7$, $X=(CHR_5)_n$, $R_1$ is H, $R_2$ is $CH_3$, $R_7$ is 4-Cl-Ph-NH; $R_3$, $R_4$, $R_5$, $R_{10}$, n and Q in Table 205 are the same as that of Table 2.

Table 206: Wherein for formula I-19, $NR_{10}$—CO-Q is at the 2-position of benzene ring, $G_1$ and $G_2$ are N, $G_3$ is $CR_8$, $X=(CHR_5)_n$, $R_1$ and $R_2$ are H, $R_8$ is Cl; $R_3$, $R_4$, $R_5$, $R_{10}$, n and Q in Table 206 are the same as that of Table 2.

Table 207: Wherein for formula I-19, $NR_{10}$—CO-Q is at the 2-position of benzene ring, $G_1$ and $G_2$ are N, $G_3$ is $CR_8$, $X=(CHR_5)_n$, $R_1$, $R_2$ and $R_8$ are 11; $R_3$, $R_4$, $R_5$, $R_{10}$, n and Q in Table 207 are the same as that of Table 2.

Table 208: Wherein for formula I-19, $NR_{10}$—CO-Q is at the 2-position of benzene ring, $G_1$ and $G_2$ are N, $G_3$ is $CR_8$, $X=(CHR_5)_n$, $R_1$ and $R_2$ are H, $R_8$ is Ph; $R_3$, $R_4$, $R_5$, $R_{10}$, n and Q in Table 208 are the same as that of Table 2.

Table 209: Wherein for formula I-19, $NR_{10}$—CO-Q is at the 2-position of benzene ring, $G_1$ is $CR_6$, $G_2$ is $CR_7$, $G_3$ is $CR_8$, $X=(CHR_5)_n$, $R_1$, $R_6$, $R_7$ and $R_8$ are H, $R_2$ is $C(CH_3)_3$; $R_3$, $R_4$, $R_5$, $R_{10}$, n and Q in Table 209 are the same as that of Table 2.

Table 210: Wherein for formula I-19, $NR_{10}$—CO-Q is at the 2-position of benzene ring, $G_1$ is N, $G_2$ is $CR_7$, $G_3$ is $CR_8$, $X=(CHR_5)_n$, $R_2$ and $R_7$ are Ft, $R_1$ is Cl, $R_8$ is $CH_3$; $R_3$, $R_4$, $R_5$, $R_{10}$, n and Q in Table 210 are the same as that of Table 2.

Table 211: Wherein for formula I-19, $NR_{10}$—CO-Q is at the 2-position of benzene ring, $G_1$ is N, $G_2$ is $CR_7$, $G_3$ is $CR_8$, $X=(CHR_5)_n$, $R_2$ and $R_7$ are H, $R_1$ and $R_3$ are Cl; $R_3$, $R_4$, $R_5$, $R_{10}$, n and Q in Table 211 are the same as that of Table 2.

Table 212: Wherein for formula I-22, $NR_{10}$—CO-Q is at the 2-position of benzene ring, $G_1$ is $CR_6$, $G_2$ is $CR_7$, $G_3$ is $CR_8$, $X=(CHR_5)_n$, $R_1$, $R_2$, $R_6$ and $R_7$ are H, $R_8$ is Cl; $R_3$, $R_4$, $R_5$, $R_{10}$, n and Q in Table 212 are the same as that of Table 2.

Table 213: Wherein for formula I-22, $NR_{10}$—CO-Q is at the 2-position of benzene ring, $G_1$ is $CR_6$, $G_2$ is $CR_7$, $G_3$ is $CR_8$, $X=(CHR_5)_n$, $R_1$, $R_2$, $R_6$ and $R_7$ are H, $R_8$ is CN; $R_3$, $R_4$, $R_5$, $R_{10}$, n and Q in Table 213 are the same as that of Table 2.

Table 214: Wherein for formula I-22, $NR_{10}$—CO-Q is at the 2-position of benzene ring, $G_1$ is $CR_6$, is $G_2$ is $CR_7$, $G_3$ is $CR_8$, $X=(CHR_5)_n$, $R_1$, $R_2$, $R_6$ and $R_7$ are H, $R_8$ is $CF_3$; $R_3$, $R_4$, $R_5$, $R_{10}$, n and Q in Table 214 are the same as that of Table 2.

Table 215: Wherein for formula I-22, $NR_{10}$—CO-Q is at the 2-position of benzene ring, $G_1$ is $CR_6$, $G_2$ is $CR_7$, $G_3$ is CR$_8$, X=(CHR$_5$)$_n$, R$_7$, R$_6$ and R$_7$ are H, R$_1$ is Cl, R$_8$ is CF$_3$; R$_3$, R$_4$, R$_5$, R$_{10}$, n and Q in Table 215 are the same as that of Table 2.

Table 216: Wherein for formula I-22, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_2$, R$_6$ and R$_7$ are H, R$_1$ is NO$_2$, R$_8$ is CF$_3$; R$_3$, R$_4$, R$_5$, R$_{10}$, n and Q in Table 216 are the same as that of Table 2.

Table 217: Wherein for formula I-22, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_2$ and R$_7$ are H, R$_1$ and R$_6$ are Cl, R$_8$ is CF$_3$; R$_3$, R$_4$, R$_5$, R$_{10}$, n and Q in Table 217 are the same as that of Table 2.

Table 218: Wherein for formula I-22, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_2$ and R$_7$ are 14, R$_1$ and R$_6$ are NO$_2$, R$_8$ is CF$_3$; R$_3$, R$_4$, R$_5$, R$_{10}$, n and Q in Table 218 are the same as that of Table 2.

Table 219: Wherein for formula I-22, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_2$ and R$_7$ are H, R$_1$ and R$_6$ are Cl, R$_8$ is CN; R$_3$, R$_4$, R$_5$, R$_{10}$, n and Q in Table 219 are the same as that of Table 2.

Table 220: Wherein for formula I-22, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_1$ and R$_6$ are NO$_2$, R$_2$ is C$_1$, R$_7$ is H, R$_8$ is CF$_3$; R$_3$, R$_4$, R$_5$, R$_{10}$, n and Q in Table 220 are the same as that of Table 2.

Table 221: Wherein for formula I-22, NR$_{10}$—CO-Q is at the 2-position of benzene ring, G$_1$ is N, G$_2$ is CR$_7$, G$_3$ is CR$_8$, X=(CHR$_5$)$_n$, R$_1$ is C$_1$, R$_2$, R$_7$ and R$_8$ are 11; R$_3$, R$_4$, R$_5$, R$_{10}$, n and Q in Table 221 are the same as that of Table 2.

Table 222: Wherein for formula I-22, NR$_{10}$—CO-Q is at the 2-position of benzene ring, G$_1$ is N, G$_2$ is CR$_7$, G$_3$ is CR$_8$, X=(CHR$_5$)$_n$, R$_8$ is CF$_3$, R$_4$, R$_2$ and R$_7$ are H; R$_3$, R$_4$, R$_5$, R$_{10}$, n and Q in Table 222 are the same as that of Table 2.

Table 223: Wherein for formula I-22, NR$_{10}$—CO-Q is at the 2-position of benzene ring, G$_1$ is N, G$_2$ is CR$_7$, G$_3$ is CR$_8$, X=(CHR$_5$)$_n$, R$_1$ is Cl, R$_8$ is CF$_3$, R$_1$, R$_2$ and R$_7$ are H; R$_3$, R$_4$, R$_5$, R$_{10}$, n and Q in Table 223 are the same as that of Table 2.

Table 224: Wherein for formula I-22, NR$_{10}$—CO-Q is at the 2-position of benzene ring, G$_1$ is N, G$_2$ is CR$_7$, G$_3$ is CR$_8$, X=(CHR$_5$)$_n$, R$_1$ is Cl, R$_8$ is CN, R$_2$ and R$_7$ are H; R$_3$, R$_4$, R$_5$, R$_{10}$, n and Q in Table 224 are the same as that of Table 2.

Table 225: Wherein for formula I-22, NR$_{10}$—CO-Q is at the 2-position of benzene ring, G$_1$ is N, G$_2$ is CR$_7$, G$_3$ is CR$_8$, X=(CHR$_5$)$_n$, R$_1$ is H, R$_2$ is CF$_3$, R$_7$ is Cl, R$_8$ is CN; R$_3$, R$_4$, R$_5$, R$_{10}$, n and Q in Table 225 are the same as that of Table 2.

Table 226: Wherein for formula I-22, NR$_{10}$—CO-Q is at the 2-position of benzene ring, G$_1$ is N, G$_2$ is CR$_7$, G$_3$ is CR$_8$, X=(CHR$_5$)$_n$, R$_1$ is H, R$_2$ is CH$_3$, R$_7$ is Cl, R$_8$ is CN; R$_3$, R$_4$, R$_5$, R$_{10}$, n and Q in Table 226 are the same as that of Table 2.

Table 227: Wherein for formula I-22, NR$_{10}$—CO-Q is at the 2-position of benzene ring, G$_1$ is N, G$_2$ is CR$_7$, G$_3$ is CR$_8$, X=(CHR$_5$)$_n$, R$_1$ is CN, R$_2$ is CH$_3$, R$_7$ is CH$_3$, R$_8$ is 14; R$_3$, R$_4$, R$_5$, R$_{10}$, n and Q in Table 227 are the same as that of Table 2.

Table 228: Wherein for formula I-22, NR$_{10}$—CO-Q is at the 2-position of benzene ring, G$_1$ is N, G$_2$ is CR$_7$, G$_3$ is CR$_8$, X=(CHR$_5$)$_n$, R$_1$ is C$_1$, R$_2$ is H, R$_7$ and R$_8$ are Cl; R$_3$, R$_4$, R$_5$, R$_{10}$, n and Q in Table 228 are the same as that of Table 2.

Table 229: Wherein for formula I-22, NR$_{10}$—CO-Q is at the 2-position of benzene ring, G$_1$ and G$_3$ are N, G$_2$ is CR$_7$, X=(CHR$_5$)$_n$, R$_1$ is C$_1$, R$_2$ is CH$_3$, R$_7$ is H; R$_3$, R$_4$, R$_5$, R$_{10}$, n and Q in Table 229 are the same as that of Table 2.

Table 230: Wherein for formula I-22, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CF$_3$, R$_7$ is CH(CH$_3$)$_2$O; R$_3$, R$_4$, R$_5$, R$_{10}$, n and Q in Table 230 are the same as that of Table 2.

Table 231: Wherein for formula I-22, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CF$_3$, R$_7$ is cyclopropyl; R$_3$, R$_4$, R$_5$, R$_{10}$, n and Q in Table 231 are the same as that of Table 2.

Table 232: Wherein for formula I-22, NR$_{10}$—CO-Q is at the 2-position of benzene ring, G$_1$ and G$_3$ are N, G$_2$ is CR$_7$, X=(CHR$_5$)$_n$, R$_1$ is CH$_3$, R$_2$ is Ph, R$_7$ is CH$_3$; R$_3$, R$_4$, R$_5$, R$_{10}$, n and Q in Table 232 are the same as that of Table 2.

Table 233: Wherein for formula I-22, NR$_{10}$—CO-Q is at the 2-position of benzene ring, G$_1$ and G$_3$ are N, G$_2$ is CR$_7$, X=(CHR$_5$)$_n$, R$_1$ is CH$_3$, R$_2$ is 4-Cl-Ph, R$_7$ is CH$_3$; R$_3$, R$_4$, R$_5$, R$_{10}$, n and Q in Table 233 are the same as that of Table 2.

Table 234: Wherein for formula I-22, NR$_{10}$—CO-Q is at the 2-position of benzene ring, G$_1$ and G$_3$ are N, G$_2$ is CR$_7$, X=(CHR$_5$)$_n$, R$_1$ is CH$_3$, R$_2$ is 4-CH$_3$O-Ph, R$_7$ is CH$_3$; R$_3$, R$_4$, R$_5$, R$_{10}$, n and Q in Table 234 are the same as that of Table 2.

Table 235: Wherein for formula I-22, NR$_{10}$—CO-Q is at the 2-position of benzene ring, G$_1$ and G$_3$ are N, G$_2$ is CR$_7$, X=(CHR$_5$)$_n$, R$_1$ and R$_7$ are H, R$_2$ is Cl; R$_3$, R$_4$, R$_5$, R$_{10}$, n and Q in Table 235 are the same as that of Table 2.

Table 236: Wherein for formula I-22, NR$_{10}$—CO-Q is at the 2-position of benzene ring, G$_1$ and G$_3$ are N, G$_2$ is CR$_7$, X=(CHR$_5$)$_n$, R$_1$ is F, R$_2$ is C$_1$, R$_7$ is H; R$_3$, R$_4$, R$_5$, R$_{10}$, n and Q in Table 236 are the same as that of Table 2.

Table 237: Wherein for formula I-22, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CH$_3$, R$_7$ is CH$_3$O; R$_3$, R$_4$, R$_5$, R$_{10}$, n and Q in Table 237 are the same as that of Table 2.

Table 238: Wherein for formula I-22, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CH$_3$, R$_7$ is (C$_2$H$_5$)$_2$N; R$_3$, R$_4$, R$_5$, R$_{10}$, n and Q in Table 238 are the same as that of Table 2.

Table 239: Wherein for formula I-22, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CF$_3$, R$_7$ is CH$_3$O; R$_1$, R$_4$, R$_5$, R$_{10}$, n and Q in Table 239 are the same as that of Table 2.

Table 240: Wherein for formula I-22, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CF$_3$, R$_7$ is (C$_2$H$_5$)$_2$N; R$_3$, R$_4$, R$_5$, R$_{10}$, n and Q in Table 240 are the same as that of Table 2.

Table 241: Wherein for formula I-22, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CH$_3$, R$_7$ is CH$_3$CH$_2$CH$_2$; R$_3$, R$_4$, R$_5$, R$_{10}$, n and Q in Table 241 are the same as that of Table 2.

Table 242: Wherein for formula I-22, NR$_{10}$—CO-Q is at the 2-position of benzene ring, G$_1$ and G$_3$ are N, G$_2$ is CR$_7$, X=(CHR$_5$)$_n$, R$_1$ is C$_4$H$_7$, R$_2$ is CH$_3$, R$_7$ is (C$_2$H$_5$)$_2$N; R$_3$, R$_4$, R$_5$, R$_{10}$, n and Q in Table 242 are the same as that of Table 2.

Table 243: Wherein for formula I-22, NR$_{10}$—CO-Q is at the 2-position of benzene ring, G$_1$ and G$_3$ are N, G$_2$ is CR$_7$, X=(CHR$_5$)$_n$, R$_1$ is C$_4$H$_9$, R$_2$ is CH$_3$, R$_7$ is C$_2$H$_5$NH; R$_3$, R$_4$, R$_5$, R$_{10}$, n and Q in Table 243 are the same as that of Table 2.

Table 244: Wherein for formula I-22, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CH$_3$, R$_7$ is Ph-NH; R$_3$, R$_4$, R$_5$, R$_{10}$, n and Q in Table 244 are the same as that of Table 2.

Table 245: Wherein for formula I-22, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CF$_3$, R$_7$ is 4-Cl-Ph-NH; R$_3$, R$_4$, R$_5$, R$_{10}$, n and Q in Table 245 are the same as that of Table 2.

Table 246: Wherein for formula I-22, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CF$_3$, R$_7$ is Ph-NH; R$_3$, R$_4$, R$_5$, R$_{10}$, n and Q in Table 246 are the same as that of Table 2.

Table 247: Wherein for formula I-22, $NR_{10}$—CO-Q is at the 2-position of benzene ring, $G_1$ and $G_3$ are N, $G_2$ is $CR_7$, $X=(CHR_5)_n$, $R_1$ is H, $R_2$ is $CH_3$, $R_7$ is 4-Cl-Ph-NH; $R_3$, $R_4$, $R_5$, $R_{10}$, n and Q in Table 247 are the same as that of Table 2.

Table 248: Wherein for formula I-22, $NR_{10}$—CO-Q is at the 2-position of benzene ring, $G_1$ and $G_2$ are N, $G_3$ is $CR_8$, $X=(CHR_5)_n$, $R_1$ and $R_2$, are H, $R_8$ is Cl; $R_3$, $R_4$, $R_5$, $R_{10}$, n and Q in Table 248 are the same as that of Table 2.

Table 249: Wherein for formula I-22, $NR_{10}$—CO-Q is at the 2-position of benzene ring, $G_1$ and $G_2$ are N, $G_3$ is $CR_8$, $X=(CHR_5)_n$, $R_1$, $R_2$ and $R_8$ are H; $R_3$, $R_4$, $R_5$, $R_{10}$, n and Q in Table 249 are the same as that of Table 2.

Table 250: Wherein for formula I-22, $NR_{10}$—CO-Q is at the 2-position of benzene ring, $G_1$ and $G_2$ are N, $G_3$ is $CR_8$, $X=(CHR_5)_n$, $R_1$ and $R_2$ are H, $R_8$ is Ph; $R_3$, $R_4$, $R_5$, $R_{10}$, n and Q in Table 250 are the same as that of Table 2.

Table 251: Wherein for formula I-22, $NR_{16}$—CO-Q is at the 2-position of benzene ring, $G_1$ is $CR_6$, $G_2$ is $CR_7$, $G_3$ is $CR_8$, $X=(CHR_5)_n$, $R_1$, $R_6$, $R_7$ and $R_8$ are H, $R_2$ is $C(CH_3)_3$; $R_3$, $R_4$, $R_5$, $R_{10}$, n and Q in Table 251 are the same as that of Table 2.

Table 252: Wherein for formula I-22, $NR_{10}$—CO-Q is at the 2-position of benzene ring, $G_1$ is N, $G_2$ is $CR_7$, $G_3$ is $CR_8$, $X=(CHR_5)_n$, $R_2$ and $R_7$ are H, $R_1$ is Cl, $R_8$ is $CH_3$; $R_3$, $R_4$, $R_5$, $R_{10}$, n and Q in Table 252 are the same as that of Table 2.

Table 253: Wherein for formula I-22, $NR_{10}$—CO-Q is at the 2-position of benzene ring, $G_1$ is N, $G_2$ is $CR_7$, $G_3$ is $CR_8$, $X=(CHR_5)_n$, $R_2$ and $R_7$ are H, $R_1$ and $R_8$ are Cl; $R_3$, $R_4$, $R_5$, $R_{10}$, n and Q in Table 253 are the same as that of Table 2.

Table 254: Wherein for formula I-26, $NR_{10}$—CO-Q is at the 2-position of benzene ring, $G_1$ is $CR_6$, $G_2$ is $CR_7$, $G_3$ is $CR_8$, $X=(CHR_5)_n$, $R_1$, $R_2$, $R_6$ and $R_7$ are H, $R_8$ is Cl; $R_3$, $R_4$, $R_5$, $R_{10}$, n and Q in Table 254 are the same as that of Table 2.

Table 255: Wherein for formula I-26, $NR_{10}$—CO-Q is at the 2-position of benzene ring, $G_1$ is $CR_6$, $G_2$ is $CR_7$, $G_3$ is $CR_8$, $X=(CHR_5)_n$, $R_1$, $R_2$, $R_6$ and $R_7$ are H, $R_8$ is CN; $R_3$, $R_4$, $R_5$, $R_{10}$, n and Q in Table 255 are the same as that of Table 2.

Table 256: Wherein for formula I-26, $NR_{10}$—CO-Q is at the 2-position of benzene ring, $G_1$ is $CR_6$, $G_2$ is $CR_7$, $G_3$ is $CR_8$, $X=(CHR_5)_n$, $R_1$, $R_2$, $R_6$ and $R_7$ are H, $R_8$ is $CF_3$; $R_3$, $R_4$, $R_5$, $R_{10}$, n and Q in Table 256 are the same as that of Table 2.

Table 257: Wherein for formula I-26, $NR_{10}$—CO-Q is at the 2-position of benzene ring, $G_1$ is $CR_6$, $G_2$ is $CR_7$, $G_3$ is $CR_8$, $X=(CHR_5)_n$, $R_2$, $R_6$ and $R_7$ are H, $R_1$ is Cl, $R_8$ is $CF_3$; $R_3$, $R_4$, $R_5$, $R_{10}$, n and Q in Table 257 are the same as that of Table 2.

Table 258: Wherein for formula I-26, $NR_{10}$—CO-Q is at the 2-position of benzene ring, $G_1$ is $CR_6$, $G_2$ is $CR_7$, $G_3$ is $CR_8$, $X=(CHR_5)_n$, $R_2$, $R_6$ and $R_7$ are H, $R_1$ is $NO_2$, $R_8$ is $CF_3$; $R_3$, $R_4$, $R_5$, $R_{10}$, n and Q in Table 258 are the same as that of Table 2.

Table 259: Wherein for formula I-26, $NR_{10}$—CO-Q is at the 2-position of benzene ring, $G_1$ is $CR_6$, $07$ is $CR_7$, $G_3$ is $CR_8$, $X=(CHR_5)_n$, R) and $R_7$ are 1-1, $R_1$ and $R_6$ are Cl, $R_8$ is $CF_3$; $R_3$, $R_4$, $R_5$, $R_{10}$, n and Q in Table 259 are the same as that of Table 2.

Table 260: Wherein for formula I-26, $NR_{10}$—CO-Q is at the 2-position of benzene ring, $G_1$ is $CR_6$, $07$ is $CR_7$, $G_3$ is $CR_8$, $X=(CHR_5)_n$, $R_2$ and $R_7$ are H, $R_1$ and $R_6$ are $NO_2$, $R_8$ is $CF_3$; $R_3$, $R_4$, $R_5$, $R_{10}$, n and Q in Table 260 are the same as that of Table 2.

Table 261: Wherein for formula I-26, $NR_{10}$—CO-Q is at the 2-position of benzene ring, $G_1$ is $CR_6$, $G_2$ is $CR_7$, $G_3$ is $CR_8$, $X=(CHR_5)_n$, $R_2$ and $R_7$ are H, $R_1$ and $R_6$ are Cl, $R_8$ is CN; $R_3$, $R_4$, $R_5$, $R_{10}$, n and Q in Table 261 are the same as that of Table 2.

Table 262: Wherein for formula I-26, $NR_{10}$—CO-Q is at the 2-position of benzene ring, $G_1$ is $CR_6$, $07$ is $CR_7$, $G_3$ is $CR_8$, $X=(CHR_5)_n$, $R_1$ and $R_6$ are $NO_2$, $R_2$ is $C_1$, $R_7$ is H, $R_8$ is $CF_3$; $R_3$, $R_4$, $R_5$, $R_{10}$, n and Q in Table 262 are the same as that of Table 2.

Table 263: Wherein for formula I-26, $NR_{10}$—CO-Q is at the 2-position of benzene ring, $G_1$ is N, $G_2$ is $CR_7$, $G_3$ is $CR_8$, $X=(CHR_5)_n$, $R_1$ is $C_1$, $R_2$, $R_7$ and $R_8$ are H, $R_7$ is H; $R_3$, $R_4$, $R_5$, $R_{10}$, n and Q in Table 263 are the same as that of Table 2.

Table 264: Wherein for formula I-26, $NR_{10}$—CO-Q is at the 2-position of benzene ring, $G_1$ is N, $G_2$ is $CR_7$, $G_3$ is $CR_8$, $X=(CHR_5)_n$, $R_8$ is $CF_3$, $R_4$, $R_2$ and $R_7$ are H; $R_3$, $R_4$, $R_5$, $R_{10}$, n and Q in Table 264 are the same as that of Table 2.

Table 265: Wherein for formula I-26, $NR_{10}$—CO-Q is at the 2-position of benzene ring, $G_1$ is N, $G_2$ is $CR_7$, $G_3$ is $CR_8$, $X=(CHR_5)_n$, $R_1$ is Cl, $R_8$ is $CF_3$, $R_2$ and $R_7$ are H; $R_3$, $R_4$, $R_5$, $R_{10}$, n and Q in Table 265 are the same as that of Table 2.

Table 266: Wherein for formula I-26, $NR_{10}$—CO-Q is at the 2-position of benzene ring, $G_1$ is N, $G_2$ is $CR_7$, $G_3$ is $CR_8$, $X=(CHR_5)_n$, $R_1$ is Cl, $R_8$ is CN, $R_2$ and $R_7$ are H; $R_3$, $R_4$, $R_5$, $R_{10}$, n and Q in Table 266 are the same as that of Table 2.

Table 267: Wherein for formula I-26, $NR_{10}$—CO-Q is at the 2-position of benzene ring, $G_1$ is N, $G_2$ is $CR_7$, $G_3$ is $CR_8$, $X=(CHR_5)_n$, $R_1$ is 14, $R_2$ is $CF_3$, $R_7$ is Cl, $R_8$ is CN; $R_3$, $R_4$, $R_5$, $R_{10}$, n and Q in Table 267 are the same as that of Table 2.

Table 268: Wherein for formula I-26, $NR_{10}$—CO-Q is at the 2-position of benzene ring, $G_1$, is N, $G_2$ is $CR_7$, $G_3$ is $CR_8$, $X=(CHR_5)_n$, $R_1$ is H, $R_2$ is $CH_3$, $R_7$ is Cl, $R_8$ is CN; $R_3$, $R_4$, $R_5$, $R_{10}$, n and Q in Table 268 are the same as that of Table 2.

Table 269: Wherein for formula I-26, $NR_{10}$—CO-Q is at the 2-position of benzene ring, $G_2$ is N, $G_2$ is $CR_7$, $G_3$ is $CR_8$, $X=(CHR_5)_n$, $R_1$ is CN, $R_2$ is $CH_3$, $R_7$ is $CH_3$, $R_8$ is H; $R_3$, $R_4$, $R_5$, n and Q in Table 269 are the same as that of Table 2.

Table 270: Wherein for formula I-26, $NR_{10}$—CO-Q is at the 2-position of benzene ring, $G_1$ is N, $G_2$ is $CR_7$, $G_3$ is $CR_8$, $X=(CHR_5)_n$, $R_1$ is $C_1$, $R_2$ is H, $R_7$ and $R_8$ are Cl; $R_3$, $R_4$, $R_5$, $R_{10}$, n and Q in Table 270 are the same as that of Table 2.

Table 271: Wherein for formula I-26, $NR_{10}$—CO-Q is at the 2-position of benzene ring, $G_1$ and $G_3$ are N, $G_2$ is $CR_7$, $X=(CHR_5)_n$, $R_1$ is $C_1$, $R_2$ is $CH_3$, $R_7$ is Cl; $R_3$, $R_4$, $R_5$, $R_{10}$, n and Q in Table 271 are the same as that of Table 2.

Table 272: Wherein for formula I-26, $NR_{10}$—CO-Q is at the 2-position of benzene ring, $G_1$ and $G_3$ are N, $G_2$ is $CR_7$, $X=(CHR_5)_n$, $R_1$ is H, $R_2$ is $CF_3$, $R_7$ is $CH(CH_3)_2O$; $R_3$, $R_4$, $R_5$, $R_{10}$, n and Q in Table 272 are the same as that of Table 2.

Table 273: Wherein for formula I-26, $NR_{10}$—CO-Q is at the 2-position of benzene ring, $G_1$ and $G_3$ are N, $G_2$ is $CR_7$, $X=(CHR_5)_n$, $R_1$ is H, $R_2$ is $CF_3$, $R_7$ is cyclopropyl; $R_3$, $R_4$, $R_5$, $R_{10}$, n and Q in Table 273 are the same as that of Table 2.

Table 274: Wherein for formula I-26, $NR_{10}$—CO-Q is at the 2-position of benzene ring, $G_1$ and $G_3$ are N, $G_2$ is $CR_7$, $X=(CHR_5)_n$, $R_1$ is $CH_3$, $R_2$ is Ph, $R_7$ is $CH_3$; $R_3$, $R_4$, $R_5$, $R_{10}$, n and Q in Table 274 are the same as that of Table 2.

Table 275: Wherein for formula I-26, $NR_{10}$—CO-Q is at the 2-position of benzene ring, $G_1$ and $G_3$ are N, $G_2$ is $CR_7$, $X=(CHR_5)_n$, $R_1$ is $CH_3$, $R_2$ is 4-Cl-Ph, $R_7$ is $CH_3$; $R_3$, $R_4$, $R_5$, $R_{10}$, n and Q in Table 275 are the same as that of Table 2.

Table 276: Wherein for formula I-26, $NR_{10}$—CO-Q is at the 2-position of benzene ring, $G_1$ and $G_3$ are N, $G_2$ is $CR_7$, $X=(CHR_5)_n$, $R_1$ is $CH_3$, $R_2$ is 4-$CH_3O$-Ph, $R_7$ is $CH_3$; $R_3$, $R_4$, $R_5$, $R_{10}$, n and Q in Table 276 are the same as that of Table 2.

Table 277: Wherein for formula I-26, $NR_{10}$—CO-Q is at the 2-position of benzene ring, $G_1$ and $G_3$ are N, $G_2$ is $CR_7$, $X=(CHR_5)_n$, $R_1$ and $R_7$ are H, $R_2$ is Cl; $R_3$, $R_4$, $R_5$, $R_{10}$, n and Q in Table 277 are the same as that of Table 2.

Table 278: Wherein for formula I-26, $NR_{10}$—CO-Q is at the 2-position of benzene ring, $G_1$ and $G_3$ are N, $G_2$ is $CR_7$, X=(CHR$_5$)$_n$, R$_1$ is F, R$_2$ is C$_1$, R$_7$ is H; R$_3$, R$_4$, R$_5$, R$_{10}$, n and Q in Table 278 are the same as that of Table 2.

Table 279: Wherein for formula I-26, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CH$_3$, R$_7$ is CH$_3$O; R$_3$, R$_4$, R$_5$, R$_{10}$, n and Q in Table 279 are the same as that of Table 2.

Table 280: Wherein for formula I-26, NR$_{10}$—CO-Q is at the 2-position of benzene ring, G$_1$ and G$_3$ are N, G$_2$ is CR$_7$, X=(CHR$_5$)$_n$, R$_1$ is F$_1$, R$_2$ is CH$_3$, R$_7$ is (C$_2$H$_5$)$_2$N; R$_3$, R$_4$, R$_5$, R$_{10}$, n and Q in Table 280 are the same as that of Table 2.

Table 281: Wherein for formula I-26, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CF$_3$, R$_7$ is CH$_3$O; R$_3$, R$_4$, R$_5$, R$_{10}$, n and Q in Table 281 are the same as that of Table 2.

Table 282: Wherein for formula I-26, NR$_{10}$—CO-Q is at the 2-position of benzene ring, G$_1$ and G$_3$ are N, G$_2$ is CR$_7$, X=(CHR$_5$)$_n$, R$_1$ is H, R—) is CH$_3$, R$_7$ is (C$_2$H$_5$)$_2$N; R$_3$, R$_4$, R$_5$, R$_{10}$, n and Q in Table 282 are the same as that of Table 2.

Table 283: Wherein for formula I-26, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CH$_3$, R$_7$ is CH$_3$CH$_2$CH$_2$; R$_3$, R$_4$, R$_5$, R$_{10}$, n and Q in Table 283 are the same as that of Table 2.

Table 284: Wherein for formula I-26, NR$_{10}$—CO-Q is at the 2-position of benzene ring, G$_1$ and G$_3$ are N, G$_2$ is CR$_7$, X=(CHR$_5$)$_n$, R$_1$ is C$_4$H$_9$, R$_2$ is CH$_3$, R$_7$ is (C$_2$H$_5$)$_2$N; R$_3$, R$_4$, R$_5$, R$_{10}$, n and Q in Table 284 are the same as that of Table 2.

Table 285: Wherein for formula I-26, NR$_{10}$—CO-Q is at the 2-position of benzene ring, G$_1$ and G$_3$ are N, G$_2$ is CR$_7$, X=(CHR$_5$)$_n$, R$_1$ is C$_4$H$_9$, R$_2$ is CH$_3$, R$_7$ is C$_2$H$_5$NH; R$_3$, R$_4$, R$_5$, R$_{10}$, n and Q in Table 285 are the same as that of Table 2.

Table 286: Wherein for formula I-26, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CH$_3$, R$_7$ is Ph-NH; R$_3$, R$_4$, R$_5$, R$_{10}$, n and Q in Table 286 are the same as that of Table 2.

Table 287: Wherein for formula I-26, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CF$_3$, R$_7$ is 4-Cl-Ph-NH; R$_3$, R$_4$, R$_5$, R$_{10}$, n and Q in Table 287 are the same as that of Table 2.

Table 288: Wherein for formula I-26, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CF$_3$, R$_7$ is Ph-NH; R$_3$, R$_4$, R$_5$, R$_{10}$, n and Q in Table 288 are the same as that of Table 2.

Table 289: Wherein for formula I-26, NR$_{10}$—CO-Q is at the 2-position of benzene ring, G$_1$ and G$_3$ are N, G$_2$ is CR$_7$, X=(CHR$_5$)$_n$, R$_1$ is H, R$_2$ is CH$_3$, R$_7$ is 4-Cl-Ph-NH; R$_3$, R$_4$, R$_5$, R$_{10}$, n and Q in Table 289 are the same as that of Table 2.

Table 290: Wherein for formula I-26, NR$_{10}$—CO-Q is at the 2-position of benzene ring, G$_1$ and G$_2$ are N, G$_3$ is CR$_8$, X=(CHR$_5$)$_2$, R$_1$ and R$_2$ are H, R$_8$ is Cl; R$_3$, R$_4$, R$_5$, R$_{10}$, n and Q in Table 290 are the same as that of Table 2.

Table 291: Wherein for formula I-26, NR$_{10}$—CO-Q is at the 2-position of benzene ring, G$_1$ and G$_2$ are N, G$_3$ is CR$_8$, X=(CHR$_5$)$_n$, R$_1$, R$_2$ and R$_8$ are H; R$_3$, R$_4$, R$_5$, R$_{10}$, n and Q in Table 291 are the same as that of Table 2.

Table 292: Wherein for formula I-26, NR$_{10}$—CO-Q is at the 2-position of benzene ring, G$_1$ and G$_2$ are N, G$_3$ is CR$_8$, X=(CHR$_5$)$_n$, R$_1$ and R$_2$ are H, R$_8$ is Ph; R$_3$, R$_4$, R$_5$, R$_{10}$, n and Q in Table 292 are the same as that of Table 2.

Table 293: Wherein for formula I-26, NR$_{10}$—CO-Q is at the 2-position of benzene ring, G$_1$ is CR$_6$, G$_2$ is CR$_7$, G$_3$ is CR$_8$, X=(CHR$_5$)$_n$, R$_1$, R$_6$, R$_7$ and R$_8$ are H, R$_2$ is C(CH$_3$)$_3$; R$_3$, R$_4$, R$_5$, R$_{10}$, n and Q in Table 293 are the same as that of Table 2.

Table 294: Wherein for formula I-26, NR$_{10}$—CO-Q is at the 2-position of benzene ring, G$_1$ is N, G$_2$ is CR$_7$, G$_3$ is CR$_8$, X=(CHR$_5$)$_n$, R$_2$ and R$_7$ are H, R$_1$ is Cl, R$_8$ is CH$_3$; R$_3$, R$_4$, R$_5$, R$_{10}$, n and Q in Table 294 are the same as that of Table 2.

Table 295: Wherein for formula I-26, NR$_{10}$—CO-Q is at the 2-position of benzene ring, G$_1$ is N, G$_2$ is CR$_7$, G$_3$ is CR$_8$, X=(CHR$_5$)$_n$, R$_2$ and R$_7$ are H, R$_1$ and R$_8$ are Cl; R$_3$, R$_4$, R$_5$, R$_{10}$, n and Q in Table 295 are the same as that of Table 2.

The present invention also relates to a preparation method of the compounds represented by the formula I, which can be prepared by reaction of the compounds containing amine group of the general formula IV with substituted benzoxazinone of the general formula V-A or aromatic acid chloride of the general formula V-B at the present of base:

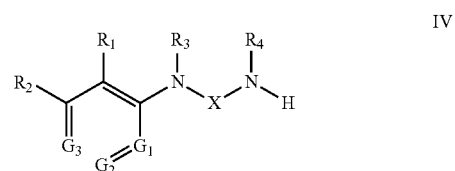

IV

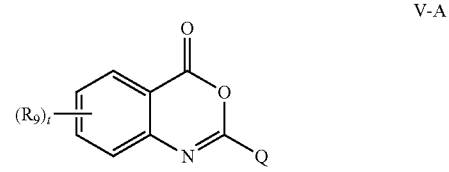

V-A

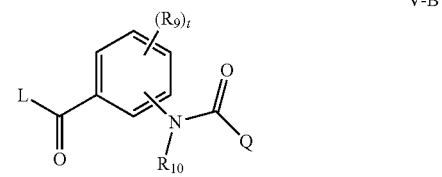

V-B

Wherein:

L is leaving group, such as Cl or Br, other groups are as defined above.

When R$_{10}$ is H and NR$_{10}$—CO-Q is at the 2-position of benzene ring, the compounds of the general formula I can be prepared by reacting (un)substituted amines of the general formula IV with substituted benzoxazinone of the general formula V-A.

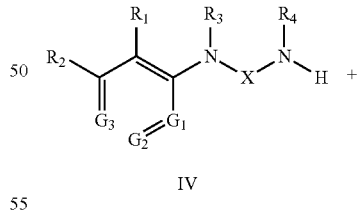

IV

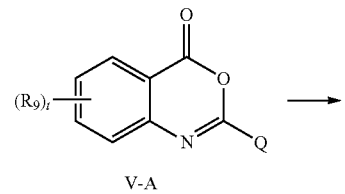

V-A

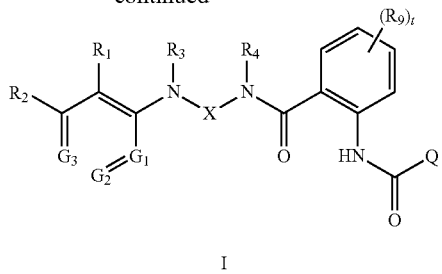

I

When $R_{10}$ is not H, and $NR_{10}$—CO-Q is at the 2-position of benzene ring or not, the compounds of the general formula I can be prepared by reacting (un)substituted amine compounds of the general formula IV with aromatic acid chloride of the general formula V-B at the present of base.

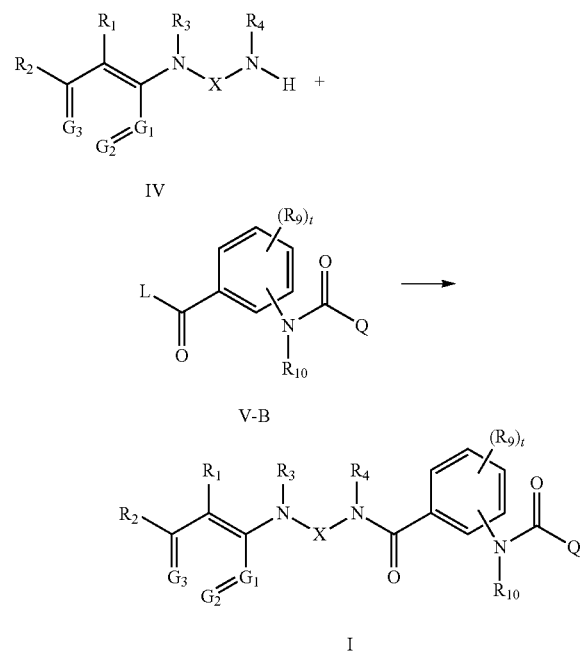

L is leaving group in general formula, such as Cl or Br, other groups are as defined above.

The general formula IV as intermediates in above reaction can be prepared by reacting aromatic halide or sulphonic acid ester compounds of the general formula II with the disubstituted or unsubstituted amine compounds of the general formula III.

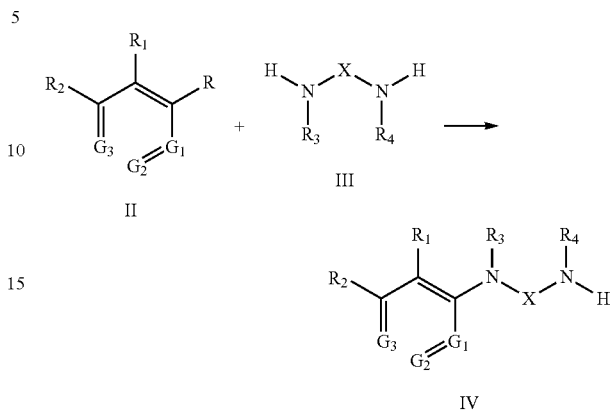

In general formula II, R is leaving group, such as Cl, Br, $OSO_2CH_3$ or $OSO_2Ph$: other groups are as defined above.

The two reactions mentioned above are similar, including react in solvent, the proper solvent may be selected from tetrahydrofuran, acetonitrile, toluene, xylene, benzene, DMF, DMSO, acetone or butanone and so on.

The proper base mentioned above may be selected from potassium hydroxide, sodium hydroxide, sodium carbonate, potassium carbonate, sodium bicarbonate, triethylamine, pyridine, sodium methoxide, sodium ethoxide, sodium hydride, potassium or sodium tert-butoxide and so on.

The proper temperature mentioned above is from room temperature to boiling point of solvent, normally the temperature is at 15 to 100° C.

The reaction may be last for 15 minutes to 20 hours, usually for 0.5 hour to 10 hours.

Aromatic halide compounds represented by the general formula II and disubstituted or unsubstituted amine compounds represented by the general formula III can be bought or prepared by conventional methods; sulphonic acid ester compounds of the general formula II can be prepared according to known methods, refer to JP56029504; benzoxazinone compounds of the general formula V-A can be prepared according to known methods, refer to WO03015519.

The general formula V-B as intermediates can be prepared from substituted amino methyl or ethyl benzoate (bought or prepared by conventional methods) by conventional methods; including amidation, alkylation, hydrolysis, chloroformylation and so on. The reaction as follows:

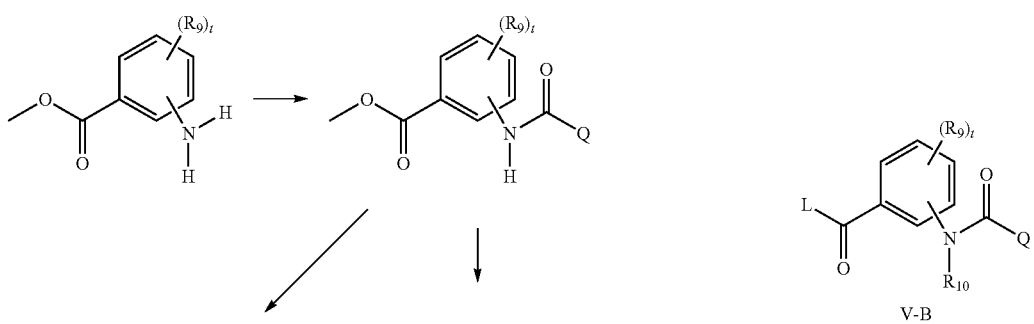

The compounds having formula I in present invention are obvious different in structures from known piperazine and amide compounds. The compounds having general formula I in the present invention have a high insecticidal activity which is exerted with respect to the adults, larvae and eggs of insects which are harmful in the agricultural, civil and zootechnical field, the compounds disclosed in the present invention also exhibit preferably fungicidal activity. A further object of the present invention therefore relates to the use of the compounds having general formula I as insecticides and/or fungicides, both in agriculture and other fields.

In particular, the compounds having general formula I are active against important species of lepidopteran, including european corn borer, sugarcane borer, codlingmoth, codling moth, gypsymoth, rice leafroller, corn borer, tobacco budworm, fruit moth, diamond back moth, cotton leafworm, especially showed good control of diamond back moth and cotton leafworm at very low doses. Additionally, some compounds in present invention also exhibit excellent fungicidal activity, which can be used to control of rice blast, tomato late blight, cucumber downy mildew, cucumber anthracnose, corn rust, wheat powdery mildew etc.

A further object of the present invention relates to insecticidal and fungicidal compositions containing compounds having general formula I as active principle and acceptable carrier in agriculture, the active component of the compositions in the weight ratio of 0.1-99%.

Compounds of the invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges that add up to 100 percent by weight

| | Weight Percent | | |
|---|---|---|---|
| | Active Ingredient | Diluent | Surfactant |
| Water-Dispersible and Water-soluble, Granules, Tablets and Powders. | 5-90 | 0-94 | 1-15 |
| Suspensions, Emulsions, Solutions (including Emulsifiable Concentrates) | 5-50 | 40-95 | 0-15 |
| Granules or Pellets | 0.01-99 | 5-99.99 | 0-15 |
| High Strength Compositions | 90-99 | 0-10 | 0-2 |

Typical solid diluents are described by Watkins, et al., in Handbook of Insecticide Dust Diluents and Carriers, 2nd Ed., Dorland Books, Caldwell, N.J. Typical liquid diluents are described by Marsden. Solvents Guide, 2nd Ed., Interscience, New York, 1950. McCutcheora's Detergents and Emulsifiers Annual, Allwed Publ. Corp., Ridgewood, N.J., as well as Sisely and Wood, Encyclopedia of Surface Active Agents, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N, N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Formulations can be prepared as following:

Dustable powders (DP) may be prepared by mixing a compound of active ingredient with one or more solid diluents and then mechanically grinding the mixture to a fine powder.

Soluble powders (SP) may be prepared by mixing a compound of active ingredient with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water solubleules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of active ingredient and one or more powdered solid diluents or carriers, or from pre-formed blank granules by absorbing a compound of active ingredient (or a solution thereof, in a suitable agent) in a porous granular material (such as pumice, attapulgite clays, fuller's earth, kieselguhr, diatomaceous earths or ground corn cobs) or by adsorbing a compound of active ingredient (or a solution thereof in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Suspension concentrates (SC) may comprise aqueous or non-aqueous suspensions of finely divided insoluble solid particles of a compound of active ingredient. SC may be prepared by ball or bead milling the solid compound of active ingredient in a suitable medium, optionally with one or more dispersing agents, to produce a fine particle suspension of the compound. One or more wetting agents may be included in the composition and a suspending agent may be included in the composition to reduce the rate at which the particles settle. Alternatively, a compound of formula (I) may be dry milled and then added to water which contains agents hereinbefore described, to produce the desired end product.

The composition to which one or more other insecticides/fungicides are added has wider spectrum activity than single compound having general formula I. In addition, other insecticides/fungicides may have synergistic effect on the insecticidal/fungicidal activity of the compound having general formula I. The compound having general formula I can also be used with other insecticides, or with another fungicide simultaneously.

DESCRIPTION OF THE INVENTION IN DETAIL

The following examples are illustrative to the present invention, but without being restricted thereby.

PREPARATION EXAMPLE

Example 1

The preparation of compound 83 in Table 181

(1) The Preparation of Intermediate IV-1

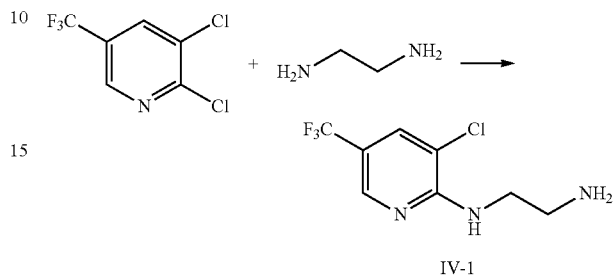

9 g (150 mmol) of 1,2-ethylenediamine and 100 ml, ethanol were added to a 250 mL flask, then 22.7 g (100 mmol) of 2,3-dichloro-5-(trifluoromethyl)pyridine was added dropwise to the solution in 30 min, stirred at room temperature for 2 h. The reaction was monitored by thin-layer chromatography (TLC), upon completion, the solvent was removed under reduced pressure, 22 g light yellow oil was obtained (91.7% yield).

(2) The Preparation of Compound 83 in Table 181

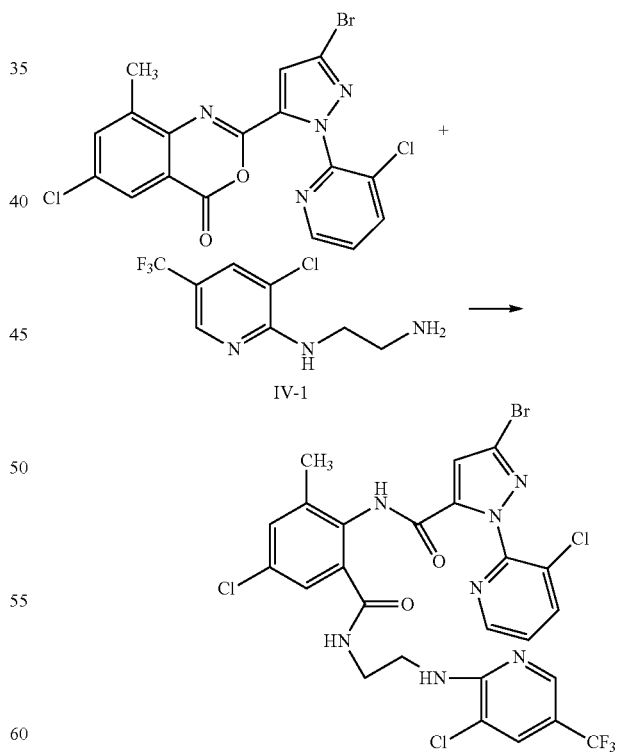

1.00 g (2.21 mmol) of 2-(3-bromo-1-(3-chloropyridin-2-yl)-1H-pyrazol-5-yl)-6-chloro-8-methyl-4H-benzo[d][1,3]oxazin-4-one (prepared according to the method disclosed in WO03015519) and 25 mL acetonitrile were added to a 50 mL flask, then 0.53 g (2.21 mmol) of IV-1 was added to the solution and stirred at 40° C. for 4 h. The reaction was monitored by TLC, upon completion, the solvent was removed under reduced pressure, then 50 mL of saturated brine was poured into the flask, extracted with 60 mL ethyl acetate for three times, the combined organic exacts were dired and concentrated. The crude product was purified through silica column (ethyl acetate:petroleum ether=1:3) and 0.65 g of target compound was obtained (42.7% yield).

Example 2

The Preparation of Compound 303 in Table 181

(1) The Preparation of Intermediate IV-2

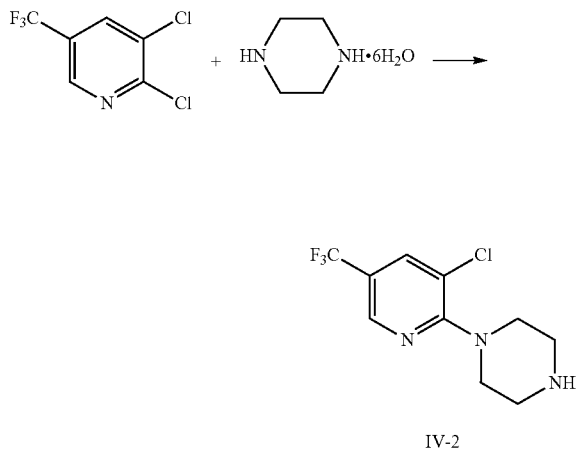

11.8 g (60 mmol) of piperazine hexahydrate was added to a 150 mL flask with 40 mL acetonitrile, heated to 40° C. 10.8 g (50 mmol) of 2,3-dichloro-5-(trifluoromethyl)pyridine was added dropwise to the solution in 15 min, then 9 mL triethylamine was added to the mixture and stirred at 40° C. for 4 h. The reaction was monitored by TLC, upon completion, filtrated and washed by a little ethanol to obtain 12 g white solid (90.2% yield).

(2) The Preparation of Compound 303 in Table 181

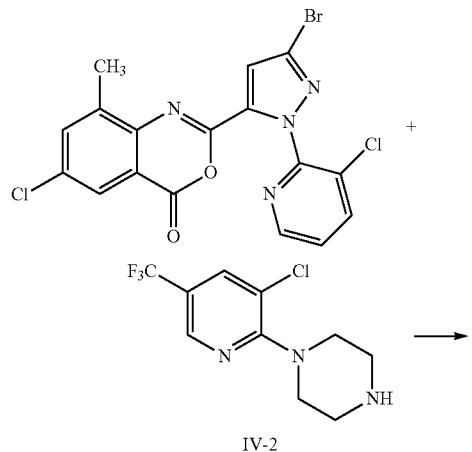

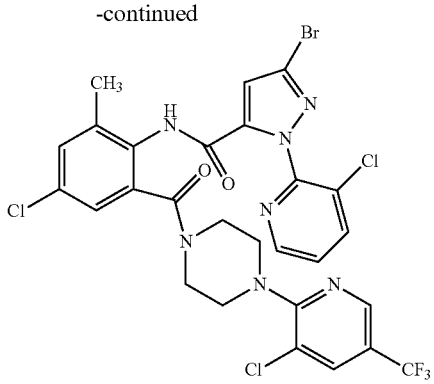

1.00 g (2.21 mmol) of 2-(3-bromo-1-(3-chloropyridin-2-yl)-1H-pyrazol-5-yl)-6-chloro-8-methyl-4H-benzo[d][1,3]oxazin-4-one (prepared according to WO03015519) and 25 mL acetonitrile were added to a 50 mL, flask, then 0.59 g (2.21 mmol) of IV-2 was added to the solution and stirred at 40 for 4 h. The reaction was monitored by TLC, upon completion, the solvent was removed under reduced pressure, and then 50 mL saturated brine was poured into the flask, extracted with 60 mL ethyl acetate for three times, the combined organic exacts were dired and concentrated. The crude product was purified through silica column (ethyl acetate:petroleum ether=1:3) and 0.58 g target compound was obtained (38.2% yield).

Example 3

The Preparation of Compound 107 in Table 96

(1) The Preparation of Intermediate V-B1

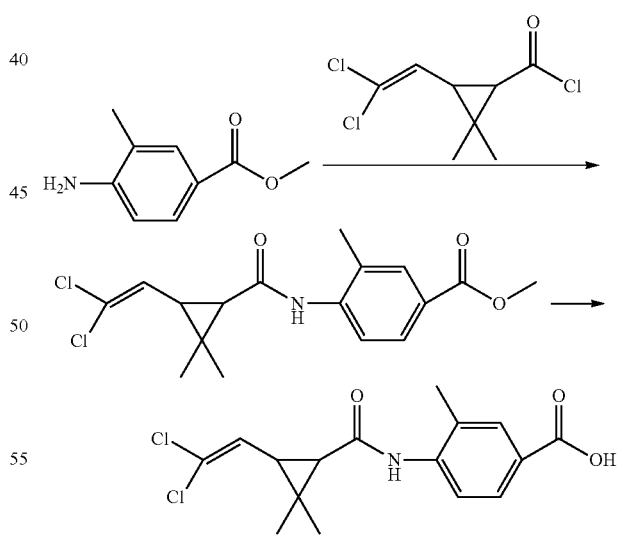

1.65 g (10 mmol) of methyl 4-amino-3-methylbenzoate and 20 mL THF were added to a 50 mL flask, and then 2.50 g (11 mmol) of acylchloride was added to the above solution and stirred at room temperature for 4 h. The reaction was monitored by TLC, upon completion, the solvent was removed under reduced pressure, then 20 mL saturated brine was poured into the flask, extracted with 60 mL ethyl acetate for three times, the combined organic exacts were washed by saturated sodium carbonate solution, dired to obtain brown solid. Then 0.8 g (20 mmol) of sodium hydroxide, 10 mL water and 20 mL ethanol were added to the flask, stirred at 50° C. for 3 h. The reaction was monitored by TLC, upon completion, the solvent was removed under reduced pressure, then 40 mL water was poured into the flask, extracted with 30 mL ethyl acetate for three times, the water layer were acidified by concentrated hydrochloric acid to weak acidity, filtrated to obtain 2.78 g white solid V-B1 (81.3% yield).

(2) The Preparation of Compound 107 in Table 96

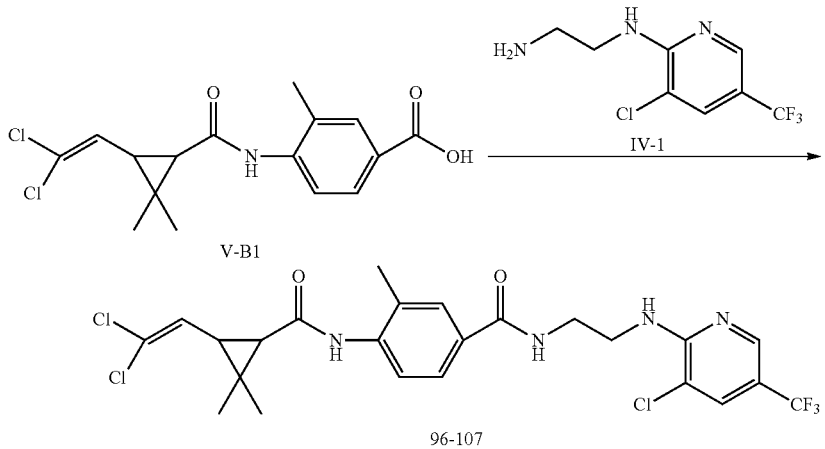

0.34 g (1 mmol) of intermediate V-B1 and 15 mL acetonitrile were added to a 50 mL flask, then 0.24 g (1 mmol) of IV-1 and 0.3 mL pyridine were added to the solution in sequence, cooled to 5° C. or less by ice bath and stirred for 10 min. Then 0.3 mL of methanesulfonyl chloride was added dropwise to the solution, removed ice bath, the reaction mixture stirred overnight at room temperature. The reaction was monitored by TLC, upon completion, the solvent was removed under reduced pressure, then 30 mL saturated brine was poured into the flask, extracted with 60 mL ethyl acetate for three times, the combined organic extacts were washed by saturated sodium carbonate solution for two times, dired and concentrated to obtain light yellow solid. The crude product was washed by a little ether, filtrated to obtain 0.27 g white solid (47.9% yield).

Other compounds of the formula I were prepared according the above examples.

Mp. and $^1$H NMR spectrum of some compounds of the formula I are as follows:

| Table No. | Compound No. | Mp. (° C.) and $^1$HNMR (300 MHz, internal standard: TMS, solvent CDCl$_3$) |
|---|---|---|
| 96 | 83 | m.p. 102-103; δppm 2.40 (3H, s), 3.81 (4H, m), 7.20 (1H, s), 7.38 (3H, m), 7.68 (2H, m), 7.86 (1H, d), 8.28 (1H, s), 8.36 (1H, m). |
| 96 | 107 | m.p. 140-142; δppm 1.34 (6H, s), 2.28 (3H, s), 3.72 (2H, s), 3.78 (2H, s), 6.12 (1H, s), 6.42 (1H, d), 7.14 (1H, s), 7.25 (1H, s), 7.51 (1H, d), 7.58 (1H, s), 7.64 (1H, s), 7.96 (1H, s), 8.26 (1H, s). |
| 96 | 303 | m.p. 158-160; δppm 2.45 (3H, s), 3.56 (4H, m), 3.94 (4H, m), 5.22 (1H, s), 7.31 (3H, m), 7.44 (1H, s), 7.81 (1H, d), 7.87 (1H, d), 8.42 (2H, m). |
| 96 | 327 | m.p. 98-99; δppm 1.28 (2H, m), 1.33 (6H, s), 2.26 (3H, s), 3.52 (8H, m), 6.41 (1H, s), 7.25 (3H, m), 7.79 (2H, m), 8.41 (1H, s). |
| 126 | 107 | m.p. 103-105; δppm 1.24 (2H, m), 1.29 (6H, m), 3.00 (3H, s), 3.68 (4H, s), 5.62 (1H, m), 7.37 (1H, s), 7.48 (2H, m), 7.60 (1H, s), 7.97 (1H, m). |
| 139 | 83 | δppm 2.27 ((3H, s), 3.30 (2H, m), 3.47 (2H, m), 7.19 (1H, s), 7.67 (1H, s), 7.89 (1H, s), 8.21 (1H, s). |

-continued

| Table No. | Compound No. | Mp. (° C.) and $^1$HNMR (300 MHz, internal standard: TMS, solvent CDCl$_3$) |
|---|---|---|
| 139 | 199 | δppm 1.89 (m, 2H), 2.26 (s, 3H), 3.49 (q, 2H), 3.68 (q, 2H), 5.82 (s, 1H), 7.06 (s, 1H), 7.39 (q, 1H), 7.52 (s, 1H), 7.61 (d, 1H), 7.69 (d, 1H), 7.72 (d, 1H), 7.84 (m, 1H), 8.18 (d, 1H), 8.44 (m, 1H), 10.78 (s, 1H). |
| 140 | 83 | δppm 2.19 (s, 3H), 3.36 (q, 2H), 3.54 (q, 2H), 7.04 (s, 1H), 7.28 (d, 1H), 7.40 (d, 1H), 7.56 (q, 1H), 7.79 (d, 1H), 8.03 (m, 1H), 8.35 (d, 1H), 8.42 (m, 1H), 10.38 (s, 1H). |
| 173 | 83 | m.p. 136-138; δppm 2.35 (3H, s), 3.30 (2H, m), 3.50 (2H, m), 6.60 (1H, s), 6.78 (1H, m), 7.11 (1H, m), 7.27 (2H, m), 7.65 (1H, m), 7.82 (1H, m), 8.00 (2H, m), 8.45 (1H, d), 10.3 (1H, s). |
| 179 | 83 | m.p. 192-194; δppm 2.17 (3H, s), 3.33 (2H, m), 3.47 (2H, m), 6.56 (1H, m). 7.34 (1H, d), 7.36 (1H, d), 7.47 (1H, d), 7.57 (2H, m), 7.97 (1H, dd), 8.12 (1H, dd), 8.45 (2H, m), 10.3 (1H, s). |
| 179 | 199 | m.p. 99-101; δppm 1.66 (2H, t), 2.17 (3H, s), 3.19 (2H, m), 3.36 (2H, m), 6.53 (1H, m), 7.37 (1H, m), 7.48 (1H, s), 7.58 (2H, m), 7.96 (1H, d), 8.12 (1H, d), 8.37 (1H, m), 8.48 (1H, d). |
| 179 | 304 | m.p. 198-200; δppm 1.19 (3H, d), 2.19 (3H, s), 3.47 (2H, m), 4.15 (2H, m), 7.09 (1H, m), 7.34 (2H, m), 7.52 (1H, m), 7.67 (1H, m), 8.02 (1H, m), 8.21 (1H, d), 8.39 (1H, m), 8.41 (1H, m), 10.25 (1H, d). |
| 180 | 303 | δppm 2.08 (3H, s), 3.15 (4H, m), 3.62 (4H, m), 6.89 (1H, d), 7.29 (1H, s), 7.35 (1H, dd), 7.40 (1H, s), 7.45 (1H, s), 7.82 (1H,, d), 7.97 (1H, d), 8.23 (1H, d0, 8.44 (1H, s), 10.4 (1H, s). |
| 181 | 83 | m.p. 200-202; δppm 2.20 (3H, s), 3.34 (2H, m), 3.52 (2H, m), 7.09 (1H, m), 7.31 (2H, m), 7.37 (1H, s), 7.50 (1H, m), 7.74 (1H, m), 8.02 (1H, d), 8.24 (1H, s), 8.41 (2H, m), 10.3 (1H, s). |
| 181 | 199 | m.p. 129-130; δppm 1.83 (2H, m), 2.17 (3H, s), 3.44 (2H, m), 3.63 (2H, m), 5.82 (1H, m), 7.13 (1H, s), 7.25 (1H, m), 7.36 (2H, m), 7.49 (1H, m), 7.66 (1H, d), 7.82 (1H, dd), 8.21 (1H, s), 10.4 (1H, s). |
| 181 | 303 | m.p. 221-222; δppm 2.26 (3H, s), 3.24 (4H, m), 3.38 (4H, m), 7.20 (1H, s), 7.40 (2H, m), 7.45 (1H, m), 8.00 (2H, m), 8.34 (1H, d), 8.53 (1H, s), 10.33 (1H, s). |
| 181 | 304 | m.p. 105-107; δppm 1.13 (3H, d), 2.16 (3H, s), 3.37 (2H, m), 4.18 (2H, m), 6.55 (1H, dd), 7.23 (1H, m), 7.36 (2H, m), 7.46 (1H, m), 7.59 (2H, m), 7.96 (1H, d), 8.13 (2H, m), 8.46 (2H, m). |
| 182 | 83 | δppm 2.20 (s, 3H), 3.34 (q, 2H), 3.51 (q, 2H), 7.06 (s, 1H), 7.32 (d, 1H), 7.36 (d, 1H), 7.51 (q, 1H), 7.85 (d, 1H), 8.01 (m, 1H), 8.31 (d, 1H), 8.40 (m, 1H,), 10.26 (s, 1H). |
| 182 | 199 | δppm 1.84 (m, 2H), 2.21 (s, 3H), 3.44 (q, 2H), 3.64 (q, 2H), 6.20 (s, 1H), 6.98 (s, 1H), 7.04 (s, 1H), 7.32 (d, 1H), 7.36 (d, 1H), 7.38 (q, 1H), 7.66 (d, 1H), 7.84 (m 1H), 8.25 (d, 1H), 8.44 (m 1H), 0.10 (s, 1H) |
| 211 | 83 | δppm 2.04 (s, 3H), 3.60 (q, 2H), 3.68 (q, 2H), 5.62 (s, 1H), 7.04 (s, 1H), 7.22 (d, 1H), 7.30 (d, 1H), 7.38 (q, 1H), 7.54 (d, 1H), 7.84 (dd, 1H), 7.95 (d, 1H), 8.10 (s, 1H), 8.44 (m, 1H), 10.38 (s, 1H). |
| 211 | 199 | δppm 1.82 (m, 2H), 2.19 (s, 3H), 3.44 (q, 2H), 3.59 (q, 2H), 5.40 (s, 1H), 7.08 (s, 1H), 7.22 (d, 1H), 7.26 (d, 1H), 7.30 (d, 1H), 7.35 (q, 1H), 7.55 (s, 1H), 7.82 (m, 1H) 7.89 (d, 1H), 8.43 (m, 1H), 10.38 (s, 1H). |

FORMULATION EXAMPLE

Base on 100% Active Ingredient(Weight/Weight %)

Example 4

60% Wettable Powders

| | |
|---|---|
| Active ingredient 304 in Table 181 | 60% |
| Sodium dodecylnaphthalenesulfate | 2% |
| Sodium lignosulfonate | 9% |
| Kaolin | make up to 100% |

All solid components are well mixed and shattered until the particle size reaches the standard in order to obtain 60% wettable powder.

Example 5

5% Dusts

| | |
|---|---|
| Active ingredient 304 in Table 179 | 5% |
| Talc | make up to 100% |

All components are well mixed and the mixture is ground in a suitable mill to obtain 5% dusts.

Example 6

10% Extruder Granules

| | |
|---|---|
| Active ingredient 83 in Table 181 | 10% |
| Sodium lignosulfonate | 2% |
| Carboxymethylcellulose | 1% |
| Kaolin | make up to 100% |

The active ingredient 83 in Table 181 is mixed with the additives, and the mixture is ground, moistened with water, extruded, granulated and dried in a stream of air.

Example 7

40% Suspension Concentrate

| | |
|---|---|
| Active ingredient 199 in Table 181 | 40% |
| Glycol | 10% |
| Nonylphenols polyethylene glycol ether | 6% |
| Sodium lignosulfonate | 10% |
| Carboxymethyl cellulose | 1% |
| 37% formaldehyde aqueous solution | 0.2% |
| 75% of silicone oil water emulsion | 0.8% |
| Water | make up to 100% |

Compound 199 in Table 181 and other components are well mixed to obtain suspension concentrate, which can be diluted with water to give suspensions of any desired concentration.

Example 6

60% Water Dispersible Granules

| | |
|---|---|
| Active ingredient 83 in Table 179 | 60% |
| Naphthalene sulfonate formaldehyde condensate | 12% |
| N-methyl-N-oil acyl-bovine sodium | 8% |
| Polyvinylpyrrolidone | 2% |
| Carboxymethyl cellulose | 2% |
| Kaolin | make up to 100% |

Compound 83 in Table 179 is well mixed with other components, kneading together with water, which was added to the granulation 10-100 mesh machine for granulation, then dried and sieved (at the scope screen).

Biological Testing

Example 9

Determination of Fungicidal Activity

Determine the fungicidal activities of the compounds of the present invention against plant diseases, carried by following procedure:

Determination of Fungicidal Activity In Vivo:

Compounds were dissolved in acetone, and diluted to required concentration with water containing 0.1% of tween 80. Plants were sprayed by a sprayer. After 24 hours, plants were innoculated and then transferred into a dew chamber for infection. After the infection period normally one week), the plants were scored for disease control.

Part of the test results are as follows:

At 400 ppm, compound 83 in Table 96, compound 304 in Table 179, compound 83 in Table 181, compound 83 in Table 211 showed 100% control of cucumber anthracnose; compound 199 in Table 139, compound 83 and 199 in Table 211 showed more than 98% control of cucumber downy mildew; compound 303 and 107 in Table 96, compound 304 in Table 179 showed more than 70% control of grey mould.

At 50 ppm, compound 304 in Table 179, Table 181-83 showed 100% control of cucumber anthracnose.

At 25 ppm, compound Table 179-304, Table 181-83 showed more than 90% control of cucumber anthracnose.

Contrast compound chlorantraniliprole (rynaxypyr, DuPont) showed no fungicidal activity at 400 ppm.

Example 10

Determination of Insecticidal and Acaricidal Activity

Determination of insecticidal and acaricidal activity of selected compounds were carried out by following procedure:

Compounds were dissolved in mixed solvent (acetone: methanol=1:1), and diluted to required concentration with water containing 0.1% of tween 80.

The armyworm (*Leucania separata*), the second stage Juvenile of diamond backmoth (*Plutella xylostella*), lesser army worm (*Spodoptera exiqua*), green peach aphids (*Myzus persicae*) and mite (*Tetranychus cinnabarinus*) were used in biological test. The test was employed either spraying by airbrush. A test solution (0.5 ml) was sprayed at the pressure of 10 psi (0.7 kg/cm$^2$). Percent mortality was determined after two to three days.

Part of Test Results:

At 600 ppm, compounds in Table 139-83, Table 139-199, Table 140-83, Table 173-83, Table 179-83, Table 179-199, Table 179-304, Table 179-303, Table 181-83, Table 181-199, Table 181-303, Table 181-304, Table 182-83, Table 182-199, Table 211-83, Table 211-199 showed 100% control of diamond backmoth and lesser armyworm.

At 10 ppm, compounds in Table 179-304, Table 181-83, Table 181-199, Table 211-199 showed 100% control of lesser armyworm; compounds in Table 139-83, Table 139-199, Table 182-83, Table 182-199, Table 211-83 showed more than 75% control of lesser armyworm.

At 1 ppm, compounds in Table 179-304, Table 181-83, Table 181-199 showed 100% control of lesser armyworm; compound Table 182-83, Table 182-199, Table 211-199 showed more than 50% control of lesser armyworm.

At 0.1 ppm, compounds in Table 181-83 showed more than 60% control of lesser armyworm.

What is claimed is:

1. An amide compounds compound having the general formula I:

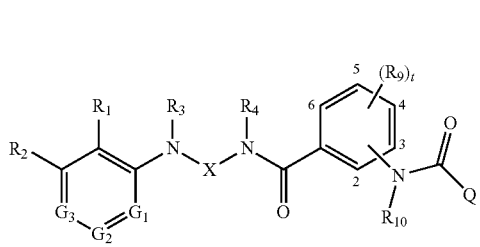

wherein:

$R_1$ and $R_2$ are each independently H, OH, halogen, CN, $NO_2$, $C_1$-$C_4$ alkyl, $C_1$-$C_4$ haloalkyl, $C_1$-$C_4$ alkoxyalkyl, $COR_{11}$, $CO_2R_{11}$, $CONR_{12}R_{11}$, $C_1$-$C_4$ alkoxy, $C_1$-$C_4$ haloalkoxy, $NR_{12}R_{11}$, $NR_{12}COR_{11}$, $NR_{12}CO_2R_{11}$, $SO_mR_{12}$, $SO_2NR_{12}R_{11}$, unsubstituted phenyl, or substituted phenyl with substituent group(s) being from 1 to 3, wherein the substituent group(s) is(are) each independently Cl, Br, F, CN, $NO_2$, $C_1$-$C_6$ alkyl, $C_1$-$C_3$ haloalkyl, $C_1$-$C_3$ haloalkoxy, or $C_1$-$C_3$ alkoxycarbonyl;

m is 0, 1 or 2;

$R_3$ and $R_4$ are each independently H, $C_1$-$C_6$ alkyl, $C_2$-$C_6$ alkenyl, $C_2$-$C_6$ alkynyl, $C_3$-$C_6$ cycloalkyl, or $C_1$-$C_4$ haloalkyl;

X is $(CHR_5)_n$; wherein n is an integer from 2 to 10; and wherein each $R_5$ is independently H, $C_1$-$C_6$ alkyl, $C_2$-$C_6$ alkenyl, $C_2$-$C_6$ alkynyl, $C_3$-$C_6$ cycloalkyl, or $C_1$-$C_6$ haloalkyl;

$G_1$ is $CR_6$ or N; $G_2$ is $CR_7$ or N; $G_3$ is $CR_8$ or N; and wherein $G_1$, $G_2$, and $G_3$ cannot be N at the same time;

$R_6$, $R_7$, and $R_8$ are each independently H, OH, halogen, CN, $NO_2$, $C_1$-$C_4$ alkyl, $C_3$-$C_6$ cycloalkyl, $CONH_2$, $CONHCH_2CN$, $C_1$-$C_3$ alkoxy, $C_1$-$C_3$ haloalkoxy, $C_1$-$C_3$ alkylthio, $C_1$-$C_3$ alkylsulfinyl, $C_1$-$C_3$ alkylsulfonyl, $C_1$-$C_3$ alkoxycarbonyl, $C_1$-$C_3$ alkylcarbonyl, $C_1$-$C_3$ alkylamino, $C_2$-$C_6$ dialkylamino, $C_3$-$C_6$ cycloalkylamino, unsubstituted phenyl, substituted phenyl with substituent group(s) being from 1 to 4, unsubstituted phenylamino, or substituted phenylamino with substituent group(s) being from 1 to 4, wherein the substituent group(s) is(are) each independently Cl, Br, F, CN, $NO_2$, $C_1$-$C_4$ alkyl, $C_1$-$C_3$ haloalkyl, $C_1$-$C_3$ alkoxy, $C_1$-$C_3$ haloalkoxy, or $C_1$-$C_3$ alkoxycarbonyl;

$R_9$ is H, OH, halogen, CN, $NO_2$, $C_1$-$C_4$ alkyl, $C_3$-$C_6$ cycloalkyl, $C_1$-$C_3$ haloalkyl, $C_1$-$C_3$ alkoxyalkyl, $C_1$-$C_3$ alkoxy, $C_1$-$C_3$ haloalkoxy, $COR_{11}$, $CO_2R_{11}$, $CONR_{11}R_{12}$, $NR_{12}R_{11}$, $NR_{12}COR_{11}$, $NR_{12}CO_2R_{11}$, $SO_mR_{12}$, $SO_2NR_{12}R_{11}$, unsubstituted phenyl, substituted phenyl, unsubstituted pyrazolyl, substituted pyrazolyl, unsubstituted pyridyl, or substituted pyridyl, wherein the substituent group(s) being from 1 to 3 is(are) each independently halogen, CN, $NO_2$, $C_1$-$C_4$ alkyl, $C_3$-$C_6$ cycloalkyl, $C_1$-$C_3$ haloalkyl, $C_1$-$C_3$ alkoxyalkyl, $C_1$-$C_3$ alkoxy, $C_1$-$C_3$ haloalkoxy, $COR_{11}$, $CO_2R_{11}$, $CONR_{11}R_{12}$, $NR_{11}R_{12}$, $NR_{12}COR_{11}$, $NR_{12}CO_2R_{11}$, $SO_mR_{12}$, or $SO_2NR_{11}R_{12}$;

t is 1, 2, 3, or 4;

$R_{10}$ and $R_{11}$ are each independently H or $C_1$-$C_4$ alkyl;

$R_{12}$ is H, $C_1$-$C_4$ alkyl, $C_1$-$C_3$ haloalkyl, unsubstituted phenyl, or substituted phenyl, wherein the substituent group is Cl, Br, F, CN, $NO_2$, $C_1$-$C_4$ alkyl, $CF_3$, $OCH_3$, $OCF_3$, or $CO_2CH_3$;

Q is unsubstituted $C_1$-$C_4$ alkyl, substituted $C_1$-$C_4$ alkyl, unsubstituted cyclopropyl, or substituted cyclopropyl, wherein the substituent group(s) being from 1 to 4 is(are) each independently Cl, Br, F, $C_1$-$C_4$ alkyl, unsubstituted phenylamino, substituted phenylamino, unsubstituted $C_2$-$C_4$ alkenyl, or substituted $C_2$-$C_4$ alkenyl, wherein the substituent group(s) being from 1 to 3 is(are) each independently Cl, Br, F, $C_1$-$C_4$ alkyl, $C_3$-$C_6$ cycloalkyl, haloalkyl, $C_1$-$C_4$ alkoxy, $C_1$-$C_4$ haloalkoxy, or $C_1$-$C_4$ alkoxycarbonyl; or unsubstituted phenyl, substituted phenyl, unsubstituted pyrazolyl, substituted pyrazolyl, unsubstituted pyridyl, or substituted pyridyl, wherein the substituent group(s) being from 1 to 4 is(are) each independently halogen, CN, $NO_2$, $C_1$-$C_4$ alkyl, $C_3$-$C_6$ cycloalkyl, $C_1$-$C_3$ haloalkyl, $C_1$-$C_3$ alkoxyalkyl, $C_1$-$C_3$ alkoxy, $C_1$-$C_3$ haloalkoxy, $COR_{11}$, $CO_2R_{11}$, $CONR_{11}R_{12}$, $NR_{11}R_{12}$, $NR_{12}COR_{11}$, $NR_{12}CO_2R_{11}$, $SO_mR_{12}$, or $SO_2NR_{11}R_{12}$.

2. The compound according to the claim 1, wherein general formula I:

$R_1$ is H, OH, Cl, Br, F, $NO_2$, CN, $CH_3$, $CH_2CH_3$, tert-butyl, $CF_3$, $CH_2CF_3$, $OCH_3$, $OCF_3$, $CONH_2$, $CONHCH_2CN$, $CO_2CH_3$, or $CO_2C_2H_5$;

$R_2$ is H, OH, Cl, Br, F, $NO_2$, CN, $CH_3$, $CH_2CH_3$, tert-butyl, cyclopropyl, $CF_3$, $CH_2CF_3$, $OCF_3$, $OCH_2CF_3$, $CO_2CH_3$, $CO_2C_2H_5$, unsubstituted phenyl, or substituted phenyl, wherein the substituent group(s) being from 1 to 3 is(are) each independently Cl, Br, F, CN, $NO_2$, $CH_3$, $CH_2CH_3$, tert-butyl, $CF_3$, $CH_2CF_3$, $OCH_3$, $OCF_3$, $CO_2CH_3$, or $CO_2C_2H_5$;

$R_3$ and $R_4$ are each independently H or $C_1$-$C_3$ alkyl;

X is $(CHR_5)_6$; wherein n is an integer selected from 2 to 10; and wherein each $R_5$ is independently H, $C_1$-$C_3$ alkyl, or $C_1$-$C_3$ haloalkyl;

$G_1$ is $CR_6$ or N; $G_2$ is $CR_7$ or N; $G_3$ is $CR_8$ or N; and wherein $G_1$, $G_2$, and $G_3$ cannot be N at the same time;

$R_6$, $R_7$, and $R_8$ are each independently H, OH, Cl, Br, F, CN, $NO_2$, $CH_3$, $CH_2CH_3$, tert-butyl, cyclopropyl, $CF_3$, $CH_2CF_3$, $OCF_3$, $OCH_2CF_3$, $CO_2CH_3$, $CONH_2$, $CONHCH_2CN$, $C_1$-$C_3$ alkylamino, $C_2$-$C_4$ dialkylamino, $C_3$-$C_6$ cycloalkylamino, unsubstituted phenyl, substituted phenyl with substituent group(s) being from 1 to 3, or unsubstituted phenylamino or substituted phenylamino with substituent group(s) being from 1 to 3, wherein the substituent group(s) is(are) each independently Cl, Br, I, CN, $NO_2$, $CH_3$, $CH_2CH_3$, tert-butyl, $CHF_2$, $CF_3$, $CH_2CF_3$, $OCH_3$, $OCHF_2$, $OCF_3$, $CO_2CH_3$, or $CO_2C_2H_5$;

$R_9$ is H, Cl, Br, F, CN, $NO_2$, $CH_3$, tert-butyl, $CHF_2$, $CF_3$, $OCH_3$, $OCHF_2$, $OCF_3$, $OCH_2CF_3$, $SO_2CH_3$, $C_1$-$C_3$ alkylamino, or $C_2$-$C_4$ dialkylamino;

t is 1, 2, 3, or 4;

$R_{10}$ is H, $CH_3$, or $C_2H_5$;

$NR_{10}$—CO-Q is at the 2, 3, or 4-position of benzene ring;

Q is selected from one of the following groups:

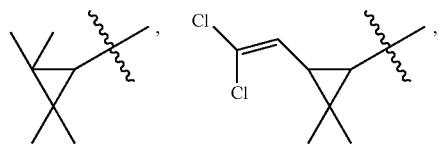

-continued

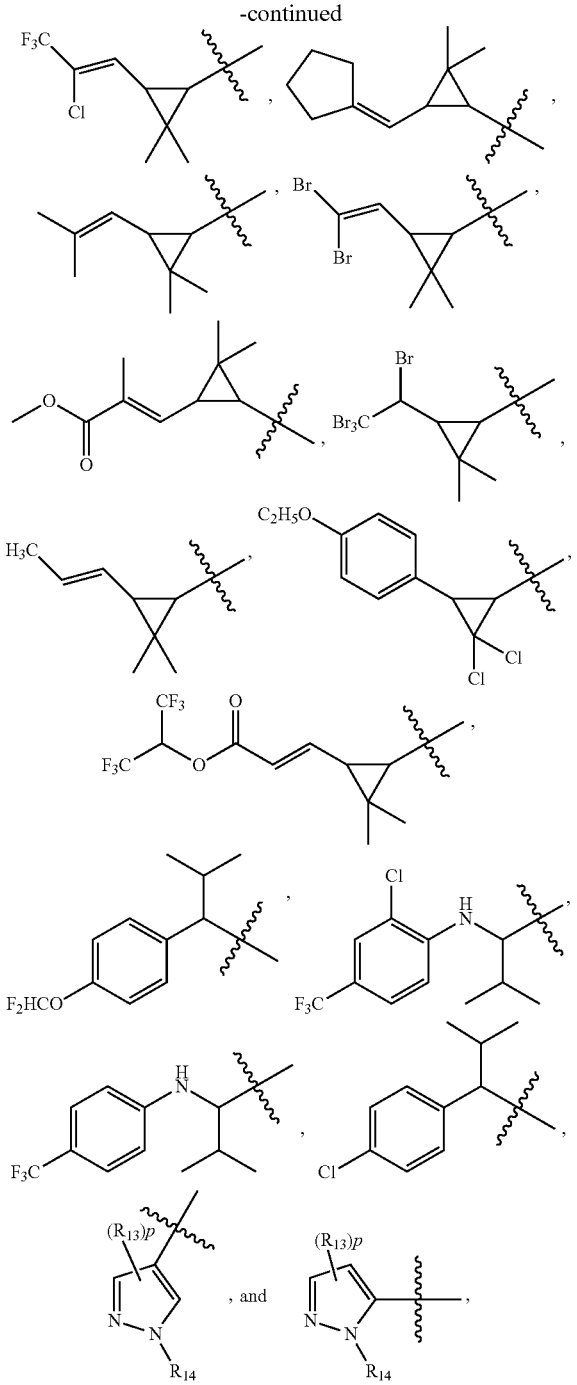

wherein:

$R_{13}$ is H, Cl, Br, F, CN, $NO_2$, $NH_2$, $CH_3$, $CH_2CH_3$, tert-butyl, cyclopropyl, $CF_3$, $CH_2CF_3$, $OCH_3$, $OCF_3$, $OCH_2CF_3$, $SO_2CH_3$, $CO_2CH_3$, $C_1$-$C_3$ alkylaminocarbonyl, $C_2$-$C_4$ dialkylaminocarbonyl, unsubstituted phenyl, substituted phenyl with substituent group(s) being from 1 to 3, unsubstituted pyridyl, or substituted pyridyl with substituent group(s) being from 1 to 3, wherein the substituent group(s) is(are) each independently H, Cl, Br, F, CN, $NO_2$, $CH_3$, $CH_2CH_3$, tert-butyl, cyclopropyl, $CHF_2$, $CF_3$, $CH_2CF_3$, $OCH_3$, $OCHF_2$, $OCF_3$, $OCH_2CF_3$, or $SO_2CH_3$;

$R_{14}$ is H, $CH_3$, $CH_2CH_3$, tert-butyl, $CF_3$, $CH_2CF_3$, unsubstituted phenyl, substituted phenyl with substituent group(s) being from 1 to 3, unsubstituted pyridyl, or substituted pyridyl with substituent group(s) being from 1 to 3, the substituent group(s) is(are) each independently Cl, Br, F, CN, $NO_2$, $CH_3$, $CH_2CH_3$, tert-butyl, cyclopropyl, $CHF_2$, $CF_3$, $CH_2CF_3$, $OCH_3$, $OCHF_2$, $OCF_3$, $OCH_2CF_3$, or $SO_2CH_3$;

p is 1 or 2.

3. The compound according to the claim 2, wherein general formula I:

$R_1$ is H, Cl, Br, F, $NO_2$, CN, $CH_3$, $CH_2CH_3$, tert-butyl, $CF_3$, $CH_2CF_3$, $OCH_3$, $OCF_3$, $CO_2CH_3$, or $CO_2C_2H_5$;

$R_2$ is H, Cl, Br, F, $NO_2$, CN, $CH_3$, $CH_2CH_3$, tert-butyl, cyclopropyl, $CF_3$, $CH_2CF_3$, $OCF_3$, $OCH_2CF_3$, $CO_2CH_3$, $CO_2C_2H_5$, unsubstituted phenyl, or substituted phenyl with the substituent group(s) being from 1 to 3 is(are) each independently Cl, Br, F, CN, $NO_2$, $CH_3$, $CH_2CH_3$, tert-butyl, $CF_3$, $CH_2CF_3$, $OCH_3$, $OCF_3$, $CO_2CH_3$, or $CO_2C_2H_5$;

$R_3$ and $R_4$ are each independently H, or $C_1$-$C_3$ alkyl;

X is $(CHR_5)_n$; wherein n is an integer selected from 2 to 10; and wherein each $R_5$ is independently H, $C_1$-$C_3$ alkyl, or $C_1$-$C_3$ haloalkyl;

$G_1$ is $CR_6$ or N; $G_2$ is $CR_7$ or N; $G_3$ is $CR_8$ or N; and wherein $G_1$, $G_2$, and $G_3$ cannot be N at the same time;

$R_6$, $R_7$, and $R_8$ are each independently H, Cl, Br, F, CN, $NO_2$, $CH_3$, $CH_2CH_3$, tert-butyl, cyclopropyl, $CF_3$, $CH_2CF_3$, $OCF_3$, $OCH_2CF_3$, $CO_2CH_3$, $C_1$-$C_3$ alkylamino, $C_2$-$C_4$ dialkylamino, cyclopropylamino, unsubstituted phenyl, substituted phenyl with substituent group(s) being from 1 to 3, unsubstituted phenylamino, or substituted phenylamino with substituent group(s) being from 1 to 3, the substituent group(s) is(are) each independently Cl, Br, I, CN, $NO_2$, $CH_3$, $CH_2CH_3$, tert-butyl, $CHF_2$, $CF_3$, $CH_2CF_3$, $OCH_3$, $OCHF_2$, $OCF_3$, $CO_2CH_3$, or $CO_2C_2H_5$;

$R_9$ is H, Cl, Br, F, CN, $NO_2$, $CH_3$, $CHF_2$, $CF_3$, $OCH_3$, $OCHF_2$, $OCF_3$, $OCH_2CF_3$, or $SO_2CH_3$;

t is 1, 2, 3, or 4;

$R_{10}$ is H, $CH_3$, or $C_2H_5$;

$NR_{10}$—CO-Q is at the 2, 3, or 4-position of benzene ring;

Q is selected from one of the following groups:

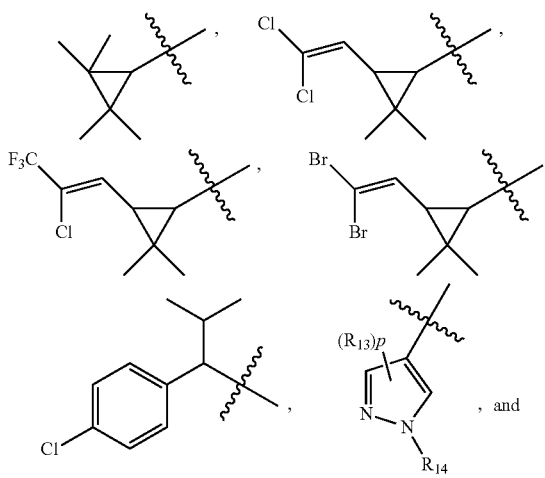

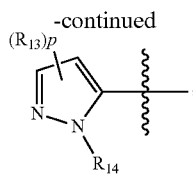

wherein:
R$_{13}$ is H, Cl, Br, F, CN, NO$_2$, CH$_3$, CH$_2$CH$_3$, tert-butyl, cyclopropyl, CF$_3$, CH$_2$CF$_3$, OCH$_3$, OCF$_3$, OCH$_2$CF$_3$, SO$_2$CH$_3$, CO$_2$CH$_3$, unsubstituted phenyl, substituted phenyl with substituent group(s) being from 1 to 3, unsubstituted pyridyl, or substituted pyridyl with substituent group(s) being from 1 to 3, the substituent group(s) is(are) each independently H, Cl, Br, F, CN, NO$_2$, CH$_3$, CH$_2$CH$_3$, tert-butyl, cyclopropyl, CHF$_2$, CF$_3$, CH$_2$CF$_3$, OCH$_3$, OCHF$_2$, OCF$_3$, OCH$_2$CF$_3$, or SO$_2$CH$_3$;

R$_{14}$ is H, CH$_3$, CH$_2$CH$_3$, tert-butyl, CF$_3$, CH$_2$CF$_3$, unsubstituted phenyl, substituted phenyl with substituent group(s) being from 1 to 3, unsubstituted pyridyl, or substituted pyridyl with substituent group(s) being from 1 to 3 the substituent group(s) is(are) each independently Cl, Br, F, CN, NO$_2$, CH$_3$, CH$_2$CH$_3$, tert-butyl, cyclopropyl, CHF$_2$, CF$_3$, CH$_2$CF$_3$, OCH$_3$, OCHF$_2$, OCF$_3$, OCH$_2$CF$_3$, or SO$_2$CH$_3$;

p is 1 or 2.

4. The compound according to the claim 3, wherein general formula I:
R$_1$ is H, Cl, Br, F, NO$_2$, CN, CH$_3$, tert-butyl, CF$_3$, OCH$_3$, or OCF$_3$;
R$_2$ is H, Cl, Br, F, NO$_2$, CN, CH$_3$, tert-butyl, cyclopropyl, CF$_3$, OCF$_3$, CO$_2$CH$_3$, or CO$_2$C$_2$H$_5$;
R$_3$ and R$_4$ are each independently H or C$_1$-C$_3$ alkyl;
X is —CH$_2$CH$_2$—, —CH$_2$CH$_2$CH$_2$—, —CH(CH$_3$)CH$_2$—, —CH(C$_2$H$_5$)CH$_2$—, —CH$_2$(CH$_2$)$_2$CH$_2$—, —CH$_2$(CH$_2$)$_3$CH$_2$—, —CH$_2$(CH$_2$)$_4$CH$_2$—, —CH$_2$(CH$_2$)$_5$CH$_2$—, —CH$_2$(CH$_2$)$_6$CH$_2$—, —CH$_2$(CH$_2$)$_7$CH$_2$—, or —CH$_2$(CH$_2$)$_8$CH$_2$—;
G$_1$ is CR$_6$ or N; G$_2$ is CR$_7$ or N; G$_3$ is CR$_8$ or N; and wherein G$_1$, G$_2$, and G$_3$ cannot be N at the same time;
R$_6$, R$_7$, and R$_8$ are each independently H, Cl, Br, F, CN, NO$_2$, CH$_3$, CH$_2$CH$_3$, tert-butyl, cyclopropyl, CF$_3$, CH$_2$CF$_3$, OCF$_3$, OCH$_2$CF$_3$ or CO$_2$CH$_3$;
R$_9$ is H, Cl, Br, F, CN, NO$_2$, CH$_3$, CHF$_2$, CF$_3$, OCH$_3$, OCHF$_2$, OCF$_3$, OCH$_2$CF$_3$, or SO$_2$CH$_3$;
t is 1, 2, 3, or 4;
R$_{10}$ is H;
NR$_{10}$—CO-Q is at the 2, 3, or 4-position of benzene ring;
Q is selected from one of the following groups:

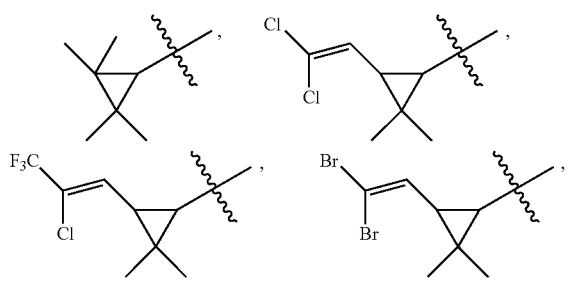

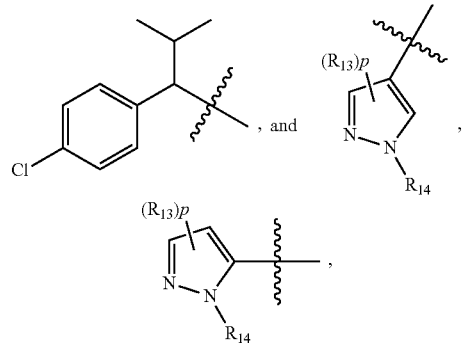

wherein:
R$_{14}$ is H, CH$_3$, unsubstituted phenyl, substituted phenyl with substituent group(s) being from 1 to 3, unsubstituted pyridyl, or substituted pyridyl with substituent group(s) being from 1 to 3, wherein the substituent group(s) is(are) each independently Cl, Br, F, CN, NO$_2$, CH$_3$, CH$_2$CH$_3$, tert-butyl, CF$_3$, OCH$_3$, or OCF$_3$;
when R$_{14}$ is H or CH$_3$, R$_{13}$ is H, Cl, Br, F, CN, CH$_3$, CH$_2$CH$_3$, tert-butyl, cyclopropyl, CF$_3$, OCH$_3$, OCF$_3$, OCH$_2$CF$_3$, SO$_2$CH$_3$, unsubstituted phenyl, or substituted phenyl, the substituent group is H, Cl, Br, F, CN, NO$_2$, CH$_3$, CH$_2$CH$_3$, tert-butyl, CHF$_2$, CF$_3$, OCH$_3$, OCHF$_2$, OCF$_3$, OCH$_2$CF$_3$, or SO$_2$CH$_3$;
when R$_{14}$ is (un)substituted phenyl or pyridyl, R$_{13}$ is H, Cl, Br, F, CN, CH$_3$, CH$_2$CH$_3$, tert-butyl, cyclopropyl, CF$_3$, OCH$_3$, OCF$_3$, OCH$_2$CF$_3$, or SO$_2$CH$_3$; and
p is 1 or 2.

5. The compound according to the claim 4, wherein general formula I:
R$_1$ is H, Cl, Br, F, NO$_2$, CN, CH$_3$, or CF$_3$;
R$_2$ is H, Cl, Br, F, NO$_2$, CN, CH$_3$, tert-butyl, cyclopropyl, CF$_3$, OCF$_3$, CO$_2$CH$_3$, or CO$_2$C$_2$H$_5$;
R$_3$ and R$_4$ are each independently H;
X is —CH$_2$CH$_2$—, —CH$_2$CH$_2$CH$_2$—, —CH(CH$_3$)CH$_2$—, —CH(C$_2$H$_5$)CH$_2$—, —CH$_2$(CH$_2$)$_2$CH$_2$—, —CH$_2$(CH$_2$)$_3$CH$_2$—, —CH$_2$(CH$_2$)$_4$CH$_2$—, —CH$_2$(CH$_2$)$_5$CH$_2$—, —CH$_2$(CH$_2$)$_6$CH$_2$—, —CH$_2$(CH$_2$)$_7$CH$_2$—, or —CH$_2$(CH$_2$)$_8$CH$_2$—;
G$_1$ is CR$_6$ or N; G$_2$ is CR$_7$ or N; G$_3$ is CR$_8$ or N; and wherein G$_1$, G$_2$, and G$_3$ cannot be N at the same time;
R$_6$, R$_7$, and R$_8$ are each independently H, Cl, Br, F, CN, NO$_2$, CH$_3$, CH$_2$CH$_3$, tert-butyl, cyclopropyl, CF$_3$, OCH$_3$, or CO$_2$CH$_3$;
R$_9$ is H, Cl, Br, F, CN, NO$_2$, CH$_3$, CHF$_2$, CF$_3$, OCH$_3$, OCHF$_2$, OCF$_3$, OCH$_2$CF$_3$, or SO$_2$CH$_3$;
t is 1 or 2;
R$_{10}$ is H;
NR$_{10}$—CO-Q is at the 2 or 4-position of benzene ring;
Q is the following pyrazolyl group:

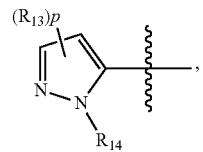

wherein:
R$_{14}$ is H, CH$_3$, unsubstituted phenyl, substituted phenyl with substituent group(s) being from 1 to 3, unsubstituted pyridyl, or substituted pyridyl both with substituent group(s) being from 1 to 3, the substituent group(s) is(are) each independently Cl, Br, F, CN, NO$_2$, CH$_3$, CH$_2$CH$_3$, tert-butyl, CF$_3$, OCH$_3$, or OCF$_3$;

when R$_{14}$ is H or CH$_3$, R$_{13}$ is H, Cl, Br, F, CN, CH$_3$, CH$_2$CH$_3$, tert-butyl, CF$_3$, OCH$_3$, OCF$_3$, SO$_2$CH$_3$, unsubstituted phenyl, or substituted phenyl with substituent group, the substituent group is H, Cl, Br, F, CN, NO$_2$, CH$_3$, CH$_2$CH$_3$, tert-butyl, CHF$_2$, CF$_3$, OCH$_3$, OCHF$_2$, OCF$_3$, or SO$_2$CH$_3$;

when R$_{14}$ is (un)substituted phenyl or pyridyl, R$_{13}$ is H, Cl, Br, F, CN, CH$_3$, CH$_2$CH$_3$, tert-butyl, CF$_3$, OCH$_3$, OCF$_3$, or SO$_2$CH$_3$;

p is 1 or 2.

6. A process for preparing the compound having general formula I according to claim 1, which comprises reacting an amine group compound having general formula IV with substituted benzoxazinone having general formula V-A or aromatic acid chloride having general formula V-B in the presence of base:

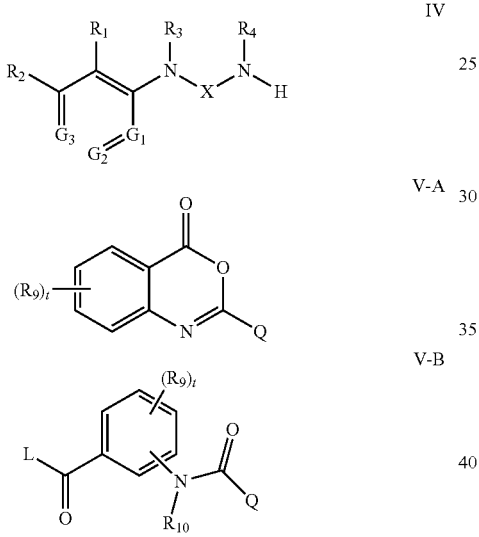

wherein:

L is leaving group, which is Cl or Br;

R$_1$ and R$_2$ are each independently H, OH, halogen, CN, NO$_2$, C$_1$-C$_4$ alkyl, C$_1$-C$_4$ haloalkyl, alkoxyalkyl, COR$_{11}$, CO$_2$R$_{11}$, CONR$_{12}$R$_{11}$, alkoxy, C$_1$-C$_4$ haloalkoxy, NR$_{12}$R$_{11}$, NR$_{12}$COR$_{11}$, NR$_{12}$CO$_2$R$_{11}$, SO$_m$R$_{12}$, SO$_2$NR$_{12}$R$_{11}$, unsubstituted phenyl, or substituted phenyl, wherein the substituent group is Cl, Br, F, CN, NO$_2$, C$_1$-C$_6$ alkyl, C$_1$-C$_3$ haloalkyl, C$_1$-C$_3$ haloalkoxy, or C$_1$-C$_3$ alkoxycarbonyl;

m is 0, 1, or 2;

R$_3$ and R$_4$ are each independently H, C$_1$-C$_6$ alkyl, C$_2$-C$_6$ alkenyl, C$_2$-C$_6$ alkynyl, C$_3$-C$_6$ cycloalkyl, or C$_1$-C$_4$ haloalkyl;

X is (CHR$_5$)$_n$; wherein n is an integer selected from 2 to 10; and wherein each R$_5$ is independently H, C$_1$-C$_6$ alkyl, C$_2$-C$_6$ alkenyl, C$_2$-C$_6$ alkynyl, C$_3$-C$_6$ cycloalkyl or C$_1$-C$_6$ haloalkyl;

G$_1$ is CR$_6$ or N; G$_2$ is CR$_7$ or N; G$_3$ is CR$_8$ or N; and wherein G$_1$, G$_2$, and G$_3$ cannot be N at the same time;

R$_6$, R$_7$, and R$_8$ are each independently H, OH, halogen, CN, NO$_2$, C$_1$-C$_4$ alkyl, C$_3$-C$_6$ cycloalkyl, CONH$_2$, CONHCH$_2$CN, C$_1$-C$_3$ alkoxy, C$_1$-C$_3$ haloalkoxy, C$_1$-C$_3$ alkylthio, C$_1$-C$_3$ alkylsulfinyl, C$_1$-C$_3$ alkylsulfonyl, C$_1$-C$_3$ alkoxycarbonyl, C$_1$-C$_3$ alkylcarbonyl, C$_1$-C$_3$ alkylamino, C$_2$-C$_6$ dialkylamino, C$_3$-C$_6$ cycloalkylamino, unsubstituted phenyl, substituted phenyl with substituent group(s) being from 1 to 4, unsubstituted phenylamino, or substituted phenylamino with substituent group(s) being from 1 to 4, the substituent group(s) is(are) each independently Cl, Br, F, CN, NO$_2$, C$_1$-C$_4$ alkyl, C$_1$-C$_3$ haloalkyl, C$_1$-C$_3$ alkoxy, C$_1$-C$_3$ haloalkoxy, or C$_1$-C$_3$ alkoxycarbonyl;

R$_9$ is H, OH, halogen, CN, NO$_2$, C$_1$-C$_4$ alkyl, C$_3$-C$_6$ cycloalkyl, C$_1$-C$_3$ haloalkyl, C$_1$-C$_3$ alkoxyalkyl, C$_1$-C$_3$ alkoxy, C$_1$-C$_3$ haloalkoxy, COR$_{11}$, CO$_2$R$_{11}$, CONR$_{11}$R$_{12}$, NR$_{12}$R$_{11}$, NR$_{12}$COR$_{11}$, NR$_{12}$CO$_2$R$_{11}$, SO$_2$NR$_{12}$R$_{11}$, unsubstituted phenyl, substituted phenyl with substituent group(s) being from 1 to 3, unsubstituted pyrazolyl, substituted pyrazolyl with substituent group(s) being from 1 to 3, unsubstituted pyridyl, or substituted pyridyl with substituent group(s) being from 1 to 3, wherein the substituent group(s) is(are) each independently halogen, CN, NO$_2$, C$_1$-C$_4$ alkyl, C$_3$-C$_6$ cycloalkyl, C$_1$-C$_3$ haloalkyl, C$_1$-C$_3$ alkoxyalkyl, C$_1$-C$_3$ alkoxy, C$_1$-C$_3$ haloalkoxy, COR$_{11}$, CO$_2$R$_{11}$, CONR$_{11}$R$_{12}$, NR$_{11}$R$_{12}$, NR$_{12}$COR$_{11}$, NR$_{12}$CO$_2$R$_{11}$, SO$_m$R$_{12}$, or SO$_2$NR$_{11}$R$_{12}$;

t is 1, 2, 3 or 4;

R$_{10}$ and R$_{11}$ are each independently H or C$_1$-C$_4$ alkyl;

R$_{12}$ is H, C$_1$-C$_4$ alkyl, C$_1$-C$_3$ haloalkyl, unsubstituted phenyl, or substituted phenyl, wherein the substituent group is Cl, Br, F, CN, NO$_2$, C$_1$-C$_4$ alkyl, CF$_3$, OCH$_3$, OCF$_3$, or CO$_2$CH$_3$;

Q is unsubstituted C$_1$-C$_4$ alkyl, substituted C$_1$-C$_4$ alkyl with substituent group(s) being from 1 to 4, unsubstituted cyclopropyl, or substituted cyclopropyl with substituent group(s) being from 1 to 4, wherein the substituent group(s) is(are) each independently Cl, Br, F, C$_1$-C$_4$ alkyl, unsubstituted phenylamino, substituted phenylamino with substituent group(s) being from 1 to 3, unsubstituted C$_2$-C$_4$ alkenyl, or substituted C$_2$-C$_4$ alkenyl with substituent group(s) being from 1 to 3, wherein the substituent group(s) is(are) each independently Cl, Br, F, C$_1$-C$_4$ alkyl, C$_3$-C$_6$ cycloalkyl, C$_1$-C$_4$ haloalkyl, C$_1$-C$_4$ alkoxy, C$_1$-C$_4$ haloalkoxy, or C$_1$-C$_4$ alkoxycarbonyl; unsubstituted phenyl, substituted phenyl with substituent group(s) being from 1 to 3, unsubstituted pyrazolyl, substituted pyrazolyl with substituent group(s) being from 1 to 3, unsubstituted pyridyl, or substituted pyridyl with substituent group(s) being from 1 to 3, in which wherein the substituent group(s) is(are) each independently halogen, CN, NO$_2$, C$_1$-C$_4$ alkyl, C$_3$-C$_6$ cycloalkyl, C$_1$-C$_3$ haloalkyl, C$_1$-C$_3$ alkoxyalkyl, C$_1$-C$_3$ alkoxy, C$_1$-C$_3$ haloalkoxy, COR$_{11}$, CO$_2$R$_{11}$, CONR$_{11}$R$_{12}$, NR$_{11}$R$_{12}$, NR$_{12}$COR$_{11}$, NR$_{12}$CO$_2$R$_{11}$, SO$_m$R$_{12}$, or SO$_2$NR$_{11}$R$_{12}$.

7. A method of controlling fungi which comprises applying the compound having general formula I according to claim 1 to agricultural and other fields.

8. A method of controlling insects which comprises applying the compound having general formula I according to claim 1 to agricultural and other fields.

9. An insecticidal or fungicidal composition comprising the compound having general formula I according to the claim 1 as an active ingredient, wherein the weight percentage of the active ingredient in the composition is in the range of 0.1-99%.

* * * * *